United States Patent
Han et al.

(10) Patent No.: US 10,683,299 B2
(45) Date of Patent: Jun. 16, 2020

(54) PYRAZOLOPYRAZINE AND TRIAZOLOPYRAZINE COMPOUNDS FOR THE TREATMENT OF INFECTIOUS DISEASES

(71) Applicant: Hoffmann-La Roche Inc., Little Falls, NJ (US)

(72) Inventors: Xingchun Han, Shanghai (CN); Xianfeng Lin, Shanghai (CN); Hong Shen, Shanghai (CN); Taishan Hu, Shanghai (CN); Zhisen Zhang, Shanghai (CN)

(73) Assignee: HOFFMANN LA ROCHE INC., Little Falls, NJ (US)

( * ) Notice: Subject to any disclaimer, the term of this patent is extended or adjusted under 35 U.S.C. 154(b) by 0 days.

(21) Appl. No.: 16/247,170

(22) Filed: Jan. 14, 2019

(65) Prior Publication Data
US 2019/0248792 A1 Aug. 15, 2019

Related U.S. Application Data

(63) Continuation of application No. PCT/EP2017/067322, filed on Jul. 11, 2017.

(51) Int. Cl.
| C07D 487/04 | (2006.01) |
| C07D 513/04 | (2006.01) |
| A61P 31/20 | (2006.01) |
| C07D 519/00 | (2006.01) |

(52) U.S. Cl.
CPC ............ *C07D 487/04* (2013.01); *A61P 31/20* (2018.01); *C07D 513/04* (2013.01); *C07D 519/00* (2013.01)

(58) Field of Classification Search
CPC .......................... C07D 487/04; C07D 513/04; A61K 31/4985; A61K 31/5383; A61K 31/541; A61K 31/542
USPC ........ 544/8, 10, 105, 350; 514/222.5, 222.8, 514/230.5, 249
See application file for complete search history.

(56) References Cited

U.S. PATENT DOCUMENTS 9,890,167 B2 * 2/2018 Hu .................. C07D 519/00

FOREIGN PATENT DOCUMENTS

| WO | 2009/085983 A1 | 7/2009 |
| WO | 2013/096744 A1 | 6/2013 |
| WO | 2014/033167 A1 | 3/2014 |
| WO | 2014/033170 A1 | 3/2014 |
| WO | 2014/111871 A1 | 7/2014 |
| WO | 2014/152725 A1 | 9/2014 |
| WO | 2016/109689 A2 | 7/2016 |
| WO | 2016/109689 A3 | 7/2016 |
| WO | 2016/113273 A1 | 7/2016 |
| WO | WO 2016/113273 A1 * | 7/2016 |
| WO | 2017/198744 A1 | 11/2017 |

OTHER PUBLICATIONS

ISR for PCT/EP2017/067322 (dated Sep. 27, 2017).
Barsanti et al., "Structure-Based Drug Design of Novel Potent and Selective Tetrahydropyrazolo[1,5-a]pyrazines as ATR Inhibitors" ACS Medicinal Chemistry Letters 6(1):37-41 (2014).

* cited by examiner

*Primary Examiner* — Deepak R Rao
(74) *Attorney, Agent, or Firm* — Genentech, Inc.; Richard G. A. Bone

(57) ABSTRACT

The present invention relates to compounds of the formula (I),

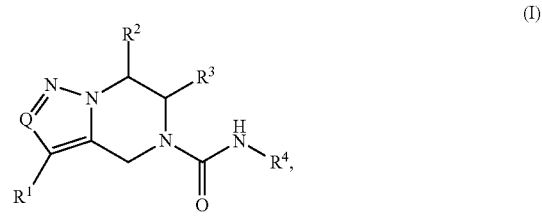

or pharmaceutically acceptable salts, enantiomer or diastereomer thereof, wherein $R^1$ to $R^4$ and Q are as described above. The compounds may be useful for the treatment or prophylaxis of hepatitis B virus infection.

12 Claims, No Drawings

PYRAZOLOPYRAZINE AND TRIAZOLOPYRAZINE COMPOUNDS FOR THE TREATMENT OF INFECTIOUS DISEASES

RELATED APPLICATIONS

This application is a continuation of International Application No. PCT/EP2017/067322, filed Jul. 11, 2017, which claims priority to Application No. PCT/CN2016/090038, filed Jul. 14, 2016, each of which are incorporated herein by reference in its entirety.

The present invention relates to organic compounds useful for therapy and/or prophylaxis in a mammal, and in particular for treating hepatitis B virus infection, and their pharmaceutical activity, manufacture, pharmaceutical compositions containing them and their potential use as medicaments.

FIELD OF THE INVENTION

The present invention relates to compounds of the formula (I),

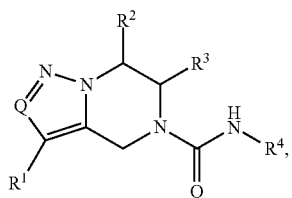

or pharmaceutically acceptable salts, enantiomer or diastereomer thereof, wherein $R^1$ to $R^4$ and Q are as described below. The compounds of this invention are useful for the treatment or prophylaxis of hepatitis B virus infection.

Hepatitis B virus (HBV) infection is a major public health problem worldwide, roughly 30% of the world's population show serological evidence of current or past infection. Despite the introduction of a safe and effective prophylactic vaccine against the virus in the early 1980s, it is estimated that there are still more than 240 million chronic HBV carriers worldwide, a high percentage of whom will eventually develop liver cirrhosis or hepatocellular carcinoma (HCC) (WHO Hepatitis B. Fact Sheet No 204). In the 2010 Global Burden of Disease study (R Lozano, et al. Lancet, 380 (2012), 2095-2128), HBV infection ranked in the top health priorities in the world, and was the tenth leading cause of death (780,000 deaths per year). Recent studies have shown that progression to liver cirrhosis and HCC in patients with chronic HBV infection is significantly associated with circulating HBV DNA levels. Thus, antiviral therapy against HBV is critical to prevent the progression to cirrhosis or development of HCC.

HBV is a small, enveloped virus that belongs to the Hepadnaviridae family. It contains a partly double-stranded DNA genome with approximately 3200 base pairs. HBV have a strong preference for infecting human hepatocytes. The life cycle begins when HBV attaches to the host cell membrane via its envelope proteins. The precise mechanism of viral entry has not been fully elucidated. The viral relaxed circular DNA (rcDNA) containing nucleocapsids are released into the cytoplasm and transported to the nucleus. In the nucleus, the rcDNA is repaired by both viral and cellular enzymes to form covalently closed circular DNA (cccDNA). There is evidence that each infected cell contains 1-50 cccDNA molecules as unique episomal minichromosomes. Both subgenomic RNA (sgRNA) and pregenomic RNA (pgRNA) are transcribed from the cccDNA using the cellular transcriptional machinery. After nuclear export, the pgRNA is translated into the core protein and the viral polymerase. The sgRNA is translated into the regulatory X protein and the three envelope proteins. Self-assembly of the RNA-containing viral nucleocapsid takes place via complex formation of the pgRNA with the core protein and the polymerase. Inside the nucleocapsid, the pgRNA is reverse transcribed into negative-strand DNA. rcDNA is then generated by plus-strand synthesis from the negative-strand DNA. The nucleocapsids are either re-imported to the nucleus for cccDNA amplification or enveloped and released via the endoplasmic reticulum (ER). The reverse transcriptase lacks proofreading activity; thus, mutations of the viral genome are frequent and result in the coexistence of genetically distinct viral species in infected individuals (quasispecies).

Currently, seven treatments are approved for chronic hepatitis B (CHB), including two formulations of interferon (IFN) (conventional IFN and PEG-IFN) and five nucleos(t)ide analogues (NUCs: lamivudine, adefovir dipivoxil, entecavir, telbivudine, and tenofovir disoproxil). The main difference between immunomodulatory agents and NUCs is that PEG-IFN has the advantage of a finite duration of use, whereas the use of NUCs is indefinite. The major drawback of PEG-IFN is its high frequency of adverse events. Some viral genotypes do not show good responses to interferon therapy. Long-term use of NUCs, on the other hand, poses the risk of drug resistance. The ultimate goal of antiviral therapy for CHB is to prevent progression to cirrhosis or HCC via eradication of HBV or persistent viral suppression. The majority of currently treated patients fail to achieve this goal. As indicated above, nucleocapsid assembly is a critical step for HBV genome replication. As the synthesis of viral DNA takes place exclusively within the nucleocapsid, the assembly and disassembly of nucleocapsid must be precisely regulated to ensure correct packaging and release of the viral genome. Nucleocapsid assembly is an evolutionary constraint process that limits the diversity of HBV, and it is highly sensitive to even subtle molecular disturbances. Both assembly and disassembly of nucleocapsid make the process an attractive therapeutic target for the development of new antiviral therapies against various HBV genotypes and drug resistance isolates. A few capsid related anti-HBV compounds have been reported. For example, heteroaryldihydropyrimidines (HAP), including compounds named Bay 41-4109, Bay 38-7690 and Bay 39-5493 (Deres K. et al. Science 2003, 893), and phenylpropenamide derivatives such as AT-61 and AT-130 (Feld J. et al. Antiviral Research 2007, 168-177). Capsid has become a promising drug target with several molecules under clinical stage. There is still a need to develop new treatments for the prophylaxis and treatment of hepatitis B virus infection.

SUMMARY OF THE INVENTION

The present invention relates to novel compounds of formula (I),

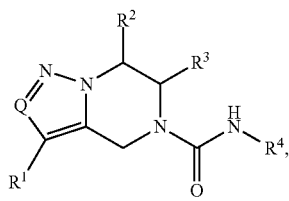

(I)

wherein

R[1] is dioxooxathiazinanyl, dioxotetrahydro[1,2,5]thiadiazolo[3,2-c][1,4]oxazinyl, dioxothiadiazinanyl, dioxothiadiazolidinyl, dioxothiazetidinyl, dioxothiazolidinyl, oxothiazolidinyl, or trioxotetrahydropyrrolo[2,1-d][1,2,5]thiadiazinyl, said dioxooxathiazinanyl, dioxotetrahydro[1,2,5]thiadiazolo[3,2-c][1,4]oxazinyl, dioxothiadiazinanyl, dioxothiadiazolidinyl, dioxothiazetidinyl, dioxothiazolidinyl, oxothiazolidinyl and trioxotetrahydropyrrolo[2,1-d][1,2,5]thiadiazinyl being unsubstituted or substituted once, twice or three times by substituents independently selected from hydroxy, $C_{1-6}$alkyl, $C_{1-6}$alkoxy, $C_{1-6}$alkylcarbonyl, benzyloxycarbonyl, carboxyphenyl, carboxypyrrolidinyl and pyrimidinyloxy;

R[2] is H or $C_{1-6}$alkyl;

R[3] is $C_{1-6}$alkyl;

R[4] is benzothiazolyl, phenyl$C_{1-6}$alkyl, phenyl, pyridinyl, thienyl or thienyl$C_{1-6}$alkyl said benzothiazolyl, phenyl$C_{1-6}$alkyl, phenyl, pyridinyl, thienyl and thienyl$C_{1-6}$alky being unsubstituted or once, twice or three times substituted by substituents independently selected from halogen, cyano, $C_{1-6}$alkyl and halo$C_{1-6}$alkyl;

Q is CH or N;

or pharmaceutically acceptable salt, enantiomer or diastereomer thereof.

Objects of the present invention are novel compounds of formula (I), their manufacture, medicaments based on a compound in accordance with the invention and their production as well as the use of compounds of formula (I) as HBV inhibitors and for the treatment or prophylaxis of HBV infection.

DETAILED DESCRIPTION OF THE INVENTION

Definitions

The term "$C_{1-6}$alkyl" denotes a monovalent linear or branched saturated hydrocarbon group of 1 to 6 carbon atoms. In particular embodiments, $C_{1-6}$alkyl has 1 to 6 carbon atoms, and in more particular embodiments 1 to 4 carbon atoms. Examples of $C_{1-6}$alkyl include methyl, ethyl, propyl, isopropyl, n-butyl, iso-butyl, sec-butyl or tert-butyl.

The term "$C_{1-6}$alkoxy" denotes $C_{1-6}$alkyl-O—.

The term "pyrimidinyloxy" denotes pyrimidinyl-O—.

The term "halo" or "halogen" are used interchangeably herein and denote fluoro, chloro, bromo or iodo.

The term "halo$C_{1-6}$alkyl" denotes a $C_{1-6}$alkyl group wherein at least one of the hydrogen atoms of the $C_{1-6}$alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 2-fluoroethyl, trifluoroethyl, fluoromethyl, difluoromethyl, difluoroethyl or trifluoromethyl.

The term "oxo" denotes a divalent oxygen atom =O.

The term "heterocyclyl" denotes a monovalent saturated or partly unsaturated mono or bicyclic ring system of 3 to 10 ring atoms, comprising 1 to 5 ring heteroatoms selected from N, O and S, the remaining ring atoms being carbon. In particular embodiments, heterocyclyl is a monovalent monocyclic ring system of 4 to 7 ring atoms, comprising 1, 2, or 3 ring heteroatoms selected from N, O and S, the remaining ring atoms being carbon. Examples for monocyclic heterocyclyl are aziridinyl, oxiranyl, azetidinyl, oxetanyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, dioxooxathiazinanyl, dioxotetrahydro[1,2,5]thiadiazolo[3,2-c][1,4]oxazinyl, dioxothiadiazinanyl, dioxothiadiazolidinyl, dioxothiazetidinyl, dioxothiazolidinyl, oxothiazolidinyl or trioxotetrahydropyrrolo[2,1-d][1,2,5]thiadiazinyl; monocyclic saturated heterocyclyl can be further substituted by benzyl, cyano, hydroxy, $C_{1-6}$alkyl, halogen, halo$C_{1-6}$alkyl, $C_{1-6}$alkylcarbonyl, benzyloxycarbonyl, $C_{1-6}$alkoxy, carboxyphenyl, carboxypyrrolidinyl or pyrimidinyloxy. Examples for substituted monocyclic heterocyclyl include, but not limited to, hydroxydioxothiadiazinanyl, acetyldioxothiadiazinanyl, benzyloxycarbonyldioxothiadiazinanyl, methyldioxothiadiazolidinyl, dimehtyldioxothiadiazolidinyl, methyldioxothiazetidinyl, hydroxydioxothiazolidinyl, hydroxy(methyl)dioxothiazolidinyl, methoxy(methyl)dioxothiazolidinyl, methyldioxothiazolidinyl, carboxyphenyldioxothiazolidinyl, carboxypyrrolidinyldioxothiazolidinyl and pyrimidinyloxy(methyl)dioxothiazolidinyl.

The term "diastereomer" denotes a stereoisomer with two or more centers of chirality and whose molecules are not mirror images of one another. Diastereomers have different physical properties, e.g. melting points, boiling points, spectral properties, activities and reactivities.

The term "enantiomers" denotes two stereoisomers of a compound which are non-superimposable mirror images of one another.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBV

The present invention provides (i) novel compounds having the general formula (I),

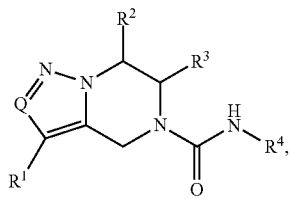

wherein $R^1$ is dioxooxathiazinanyl, dioxotetrahydro[1,2,5]thiadiazolo[3,2-c][1,4]oxazinyl, dioxothiadiazinanyl, dioxothiadiazolidinyl, dioxothiazetidinyl, dioxothiazolidinyl, oxothiazolidinyl or trioxotetrahydropyrrolo[2,1-d][1,2,5]thiadiazinyl, said dioxooxathiazinanyl, dioxotetrahydro[1,2,5]thiadiazolo[3,2-c][1,4]oxazinyl, dioxothiadiazinanyl, dioxothiadiazolidinyl, dioxothiazetidinyl, dioxothiazolidinyl, oxothiazolidinyl and trioxotetrahydropyrrolo[2,1-d][1,2,5]thiadiazinyl being unsubstituted or substituted once, twice or three times by substituents independently selected from hydroxy, $C_{1-6}$alkyl, $C_{1-6}$alkoxy, $C_{1-6}$alkylcarbonyl, benzyloxycarbonyl, carboxyphenyl, carboxypyrrolidinyl and pyrimidinyloxy;

$R^2$ is H or $C_{1-6}$alkyl;

$R^3$ is $C_{1-6}$alkyl;

$R^4$ is benzothiazolyl, phenyl$C_{1-6}$alkyl, phenyl, pyridinyl, thienyl or thienyl$C_{1-6}$alkyl said benzothiazolyl, phenyl$C_{1-6}$alkyl, phenyl, pyridinyl, thienyl and thienyl$C_{1-6}$alky being unsubstituted or once, twice or three times substituted by substituents independently selected from halogen, cyano, $C_{1-6}$alkyl and halo$C_{1-6}$alkyl;

Q is CH or N;

or pharmaceutically acceptable salt, enantiomer or diastereomer thereof.

A further embodiment of the present invention is (ii) a compound of formula (I), wherein $R^1$ is dioxooxathiazinanyl;
dioxotetrahydro[1,2,5]thiadiazolo[3,2-c][1,4]oxazinyl;
dioxothiadiazinanyl, said dioxothiadiazinanyl being unsubstituted or substituted by hydroxy, $C_{1-6}$alkylcarbonyl or benzyloxycarbonyl;
dioxothiadiazolidinyl, said dioxothiadiazolidinyl being unsubstituted or substituted once or twice by $C_{1-6}$alkyl;
dioxothiazetidinyl, said dioxothiazetidinyl being unsubstituted or substituted by $C_{1-6}$alkyl;
dioxothiazolidinyl, said dioxothiadiazolidinyl being unsubstituted or substituted once or twice by substituents independently selected from hydroxy, $C_{1-6}$alkyl, $C_{1-6}$alkoxy, carboxyphenyl, carboxypyrrolidinyl and pyrimidinyloxy;
oxothiazolidinyl; or
trioxotetrahydropyrrolo[2,1-d][1,2,5]thiadiazinyl;

$R^2$ is H;

$R^3$ is $C_{1-6}$alkyl;

$R^4$ is benzothiazolyl;
phenyl$C_{1-6}$alkyl;
phenyl, said phenyl being once, twice or three times substituted by substituents independently selected from halogen, cyano, $C_{1-6}$alkyl and halo$C_{1-6}$alkyl;
pyridinyl, said pyridinyl being substituted by halogen or halo$C_{1-6}$alkyl;
thienyl; or
thienyl$C_{1-6}$alkyl;

Q is CH or N;

or pharmaceutically acceptable salt, enantiomer or diastereomer thereof.

A further embodiment of the present invention is (iii) a compound of formula (I), wherein $R^1$ is dioxooxathiazinanyl, dioxotetrahydro[1,2,5]thiadiazolo[3,2-c][1,4]oxazinyl, dioxothiadiazinanyl, hydroxydioxothiadiazinanyl, acetyldioxothiadiazinanyl, benzyloxycarbonyldioxothiadiazinanyl, dioxothiadiazolidinyl, methyldioxothiadiazolidinyl, dimehtyldioxothiadiazolidinyl, dioxothiazetidinyl, methyldioxothiazetidinyl, dioxothiazolidinyl, hydroxydioxothiazolidinyl, hydroxy(methyl)dioxothiazolidinyl, methoxy(methyl)dioxothiazolidinyl, methyldioxothiazolidinyl, carboxyphenyldioxothiazolidinyl, carboxypyrrolidinyldioxothiazolidinyl, pyrimidinyloxy(methyl)dioxothiazolidinyl, oxothiazolidinyl or 1,1-dioxo-3a,4,6,7-tetrahydro-3H-[1,2,5]thiadiazolo[3,2-c][1,4]oxazin-2-yl;

$R^2$ is H;

$R^3$ is methyl;

$R^4$ is benzothiazolyl, benzyl, fluorophenyl, fluorochlorophenyl, fluorocyanophenyl, fluoro(methyl)phenyl, fluoro(trifluoromethyl)phenyl, trifluorophenyl, chloropyridinyl, difluoromethylpyridinyl, thienyl or thienylmethyl;

Q is CH or N;

or pharmaceutically acceptable salt, enantiomer or diastereomer thereof.

A further embodiment of the present invention is (iv) a compound of formula (I), wherein Q is CH.

A further embodiment of the present invention is (v) a compound of formula (I), wherein $R^1$ is dioxothiazolidinyl, said dioxothiadiazolidinyl being unsubstituted or substituted once or twice by substituents independently selected from hydroxy, $C_{1-6}$alkyl, $C_{1-6}$alkoxy, carboxyphenyl, carboxypyrrolidinyl and pyrimidinyloxy.

A further embodiment of the present invention is (vi) a compound of formula (I), wherein $R^1$ is dioxothiazolidinyl, hydroxydioxothiazolidinyl, hydroxy(methyl)dioxothiazolidinyl, methoxy(methyl)dioxothiazolidinyl, methyldioxothiazolidinyl, carboxyphenyldioxothiazolidinyl, carboxypyrrolidinyldioxothiazolidinyl or pyrimidinyloxy(methyl)dioxothiazolidinyl.

In another embodiment of the present invention, particular compounds of the present invention are (vii) selected from:

(6S)-3-(1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;

(6S)—N-(2-chloro-4-pyridyl)-3-(1,1-dioxo-1,2-thiazolidin-2-yl)-6-methyl-6,7-dihydro-4H-pyrazolo[1,5-a]pyrazine-5-carboxamide;

(6S)—N-(4-chloro-3-fluoro-phenyl)-3-(1,1-dioxo-1,2-thiazolidin-2-yl)-6-methyl-6,7-dihydro-4H-pyrazolo[1,5-a]pyrazine-5-carboxamide;

(6S)-3-(1,1-dioxo-1,2-thiazolidin-2-yl)-N-(4-fluoro-3-methyl-phenyl)-6-methyl-6,7-dihydro-4H-pyrazolo[1,5-a]pyrazine-5-carboxamide;

(6S)—N-(3-cyano-4-fluoro-phenyl)-3-(1,1-dioxo-1,2-thiazolidin-2-yl)-6-methyl-6,7-dihydro-4H-pyrazolo[1,5-a]pyrazine-5-carboxamide;

(6S)—N-[2-(difluoromethyl)-4-pyridyl]-3-(1,1-dioxo-1,2-thiazolidin-2-yl)-6-methyl-6,7-dihydro-4H-pyrazolo[1,5-a]pyrazine-5-carboxamide;

(6S)-3-(1,1-dioxo-1,2-thiazolidin-2-yl)-N-[4-fluoro-3-(trifluoromethyl)phenyl]-6-methyl-6,7-dihydro-4H-pyrazolo[1,5-a]pyrazine-5-carboxamide;

(6S)-3-(1,1-dioxo-1,2-thiazolidin-2-yl)-N-(2-fluorophenyl)-6-methyl-6,7-dihydro-4H-pyrazolo[1,5-a]pyrazine-5-carboxamide;

(6S)—N-(1,3-benzothiazol-6-yl)-3-(1,1-dioxo-1,2-thiazolidin-2-yl)-6-methyl-6,7-dihydro-4H-pyrazolo[1,5-a]pyrazine-5-carboxamide;

(6S)-3-(1,1-dioxo-1,2-thiazolidin-2-yl)-6-methyl-N-(3-thienyl)-6,7-dihydro-4H-pyrazolo[1,5-a]pyrazine-5-carboxamide;

6S)—N-benzyl-3-(1,1-dioxo-1,2-thiazolidin-2-yl)-6-methyl-6,7-dihydro-4H-pyrazolo[1,5-a]pyrazine-5-carboxamide;

(6S)-3-(1,1-dioxo-3a,4,6,7-tetrahydro-3H-[1,2,5]thiadiazolo[3,2-c][1,4]oxazin-2-yl)-6-methyl-N-(3,4,5-trifluorophenyl)-6,7-dihydro-4H-pyrazolo[1,5-a]pyrazine-5-carboxamide;

Benzyl 2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2,5-thiadiazinane-5-carboxylate;

(6S)-6-methyl-N-(3,4,5-trifluorophenyl)-3-(3,3,6-trioxo-4,7,8,8a-tetrahydro-1H-pyrrolo[2,1-d][1,2,5]thiadiazin-2-yl)-6,7-dihydro-4H-pyrazolo[1,5-a]pyrazine-5-carboxamide;

(6S)-3-(5-acetyl-1,1-dioxo-1,2,5-thiadiazinan-2-yl)-6-methyl-N-(3,4,5-trifluorophenyl)-6,7-dihydro-4H-pyrazolo[1,5-a]pyrazine-5-carboxamide;

(6S)-6-methyl-3-(3-methyl-1,1-dioxo-1,2-thiazolidin-2-yl)-N-(3,4,5-trifluorophenyl)-6,7-dihydro-4H-pyrazolo[1,5-a]pyrazine-5-carboxamide;

(6S)-6-methyl-3-(1-oxo-1,2-thiazolidin-2-yl)-N-(3,4,5-trifluorophenyl)-6,7-dihydro-4H-pyrazolo[1,5-a]pyrazine-5-carboxamide;

(6S)-3-(4-hydroxy-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;

(6S)-3-(1,1-dioxo-1,2,5-thiadiazolidin-2-yl)-6-methyl-N-(3,4,5-trifluorophenyl)-6,7-dihydro-4H-pyrazolo[1,5-a]pyrazine-5-carboxamide;

(6S)-6-methyl-3-(5-methyl-1,1-dioxo-1,2,5-thiadiazolidin-2-yl)-N-(3,4,5-trifluorophenyl)-6,7-dihydro-4H-pyrazolo[1,5-a]pyrazine-5-carboxamide;

(6S)-6-methyl-3-[(3S)-3-methyl-1,1-dioxo-thiazetidin-2-yl]-N-(3,4,5-trifluorophenyl)-6,7-dihydro-4H-pyrazolo[1,5-a]pyrazine-5-carboxamide;

(6S)-6-methyl-3-[(3S)-3-methyl-1,1-dioxo-1,2,5-thiadiazolidin-2-yl]-N-(3,4,5-trifluorophenyl)-6,7-dihydro-4H-pyrazolo[1,5-a]pyrazine-5-carboxamide;

(6S)-3-[(3S)-3,4-dimethyl-1,1-dioxo-1,2,5-thiadiazolidin-2-yl]-6-methyl-N-(3,4,5-trifluorophenyl)-6,7-dihydro-4H-pyrazolo[1,5-a]pyrazine-5-carboxamide;

(6S)-3-(3,3-dioxo-1,3,4-oxathiazinan-4-yl)-6-methyl-N-(3,4,5-trifluorophenyl)-6,7-dihydro-4H-pyrazolo[1,5-a]pyrazine-5-carboxamide;

(6S)-3-(1,1-dioxothiazetidin-2-yl)-6-methyl-N-(3,4,5-trifluorophenyl)-6,7-dihydro-4H-pyrazolo[1,5-a]pyrazine-5-carboxamide;

(6S)-3-(4-hydroxy-1,1-dioxo-1,2,6-thiadiazinan-2-yl)-6-methyl-N-(3,4,5-trifluorophenyl)-6,7-dihydro-4H-pyrazolo[1,5-a]pyrazine-5-carboxamide;

(6S)-3-(1,1-dioxo-1,2,6-thiadiazinan-2-yl)-6-methyl-N-(3,4,5-trifluorophenyl)-6,7-dihydro-4H-pyrazolo[1,5-a]pyrazine-5-carboxamide;

(6S)-3-(4-hydroxy-3-methyl-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;

(6S)-3-(4-hydroxy-3-methyl-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;

(6S)—N-[2-(difluoromethyl)-4-pyridyl]-3-(4-hydroxy-3-methyl-1,1-dioxo-1,2-thiazolidin-2-yl)-6-methyl-6,7-dihydro-4H-pyrazolo[1,5-a]pyrazine-5-carboxamide;

(6S)-6-methyl-3-(3-methyl-1,1-dioxo-4-pyrimidin-2-yloxy-1,2-thiazolidin-2-yl)-N-(3,4,5-trifluorophenyl)-6,7-dihydro-4H-pyrazolo[1,5-a]pyrazine-5-carboxamide;

(6S)-3-(4-methoxy-3-methyl-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;

(6S)—N-[2-(difluoromethyl)-4-pyridyl]-3-(4-methoxy-3-methyl-1,1-dioxo-1,2-thiazolidin-2-yl)-6-methyl-6,7-dihydro-4H-pyrazolo[1,5-a]pyrazine-5-carboxamide;

(6S)—N-[2-(difluoromethyl)-4-pyridyl]-3-(4-methoxy-3-methyl-1,1-dioxo-1,2-thiazolidin-2-yl)-6-methyl-6,7-dihydro-4H-pyrazolo[1,5-a]pyrazine-5-carboxamide;

3-(1,1-dioxo-1,2-thiazolidin-2-yl)-6-methyl-N-(3,4,5-trifluorophenyl)-6,7-dihydro-4H-triazolo[1,5-a]pyrazine-5-carboxamide;

3-(1,1-dioxo-1,2-thiazolidin-2-yl)-6-methyl-N-(3,4,5-trifluorophenyl)-6,7-dihydro-4H-triazolo[1,5-a]pyrazine-5-carboxamide;

(6S)-3-(1,1-dioxo-1,2-thiazolidin-2-yl)-6-methyl-N-(3-thienylmethyl)-6,7-dihydro-4H-pyrazolo[1,5-a]pyrazine-5-carboxamide;

(2S)-1-[2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2-thiazolidin-4-yl]pyrrolidine-2-carboxylic acid; and 2-[2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2-thiazolidin-4-yl]benzoic acid.

In another embodiment of the present invention, particular compounds of the present invention are (viii) selected from:

(6S)-3-(1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;

(6S)-3-(1,1-dioxo-1,2-thiazolidin-2-yl)-N-(4-fluoro-3-methyl-phenyl)-6-methyl-6,7-dihydro-4H-pyrazolo[1,5-a]pyrazine-5-carboxamide;

(6S)-6-methyl-3-(3-methyl-1,1-dioxo-1,2-thiazolidin-2-yl)-N-(3,4,5-trifluorophenyl)-6,7-dihydro-4H-pyrazolo[1,5-a]pyrazine-5-carboxamide;

(6S)-3-(4-hydroxy-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;

(6S)-3-(1,1-dioxo-1,2,5-thiadiazolidin-2-yl)-6-methyl-N-(3,4,5-trifluorophenyl)-6,7-dihydro-4H-pyrazolo[1,5-a]pyrazine-5-carboxamide;

(6S)-3-(3,3-dioxo-1,3,4-oxathiazinan-4-yl)-6-methyl-N-(3,4,5-trifluorophenyl)-6,7-dihydro-4H-pyrazolo[1,5-a]pyrazine-5-carboxamide;

(6S)-6-methyl-3-(3-methyl-1,1-dioxo-4-pyrimidin-2-yloxy-1,2-thiazolidin-2-yl)-N-(3,4,5-trifluorophenyl)-6,7-dihydro-4H-pyrazolo[1,5-a]pyrazine-5-carboxamide;

(6S)-3-(4-methoxy-3-methyl-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide; and (2S)-1-[2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2-thiazolidin-4-yl]pyrrolidine-2-carboxylic acid.

Synthesis

The compounds of the present invention can be prepared by any conventional means. Suitable processes for synthesizing these compounds as well as their starting materials are provided in the schemes below and in the examples. All substituents, in particular, $R^1$ to $R^4$ and Q are as defined above unless otherwise indicated. Furthermore, and unless explicitly otherwise stated, all reactions, reaction conditions, abbreviations and symbols have the meanings well known to a person of ordinary skill in organic chemistry.

Scheme 1: General synthetic route for compounds of this invention

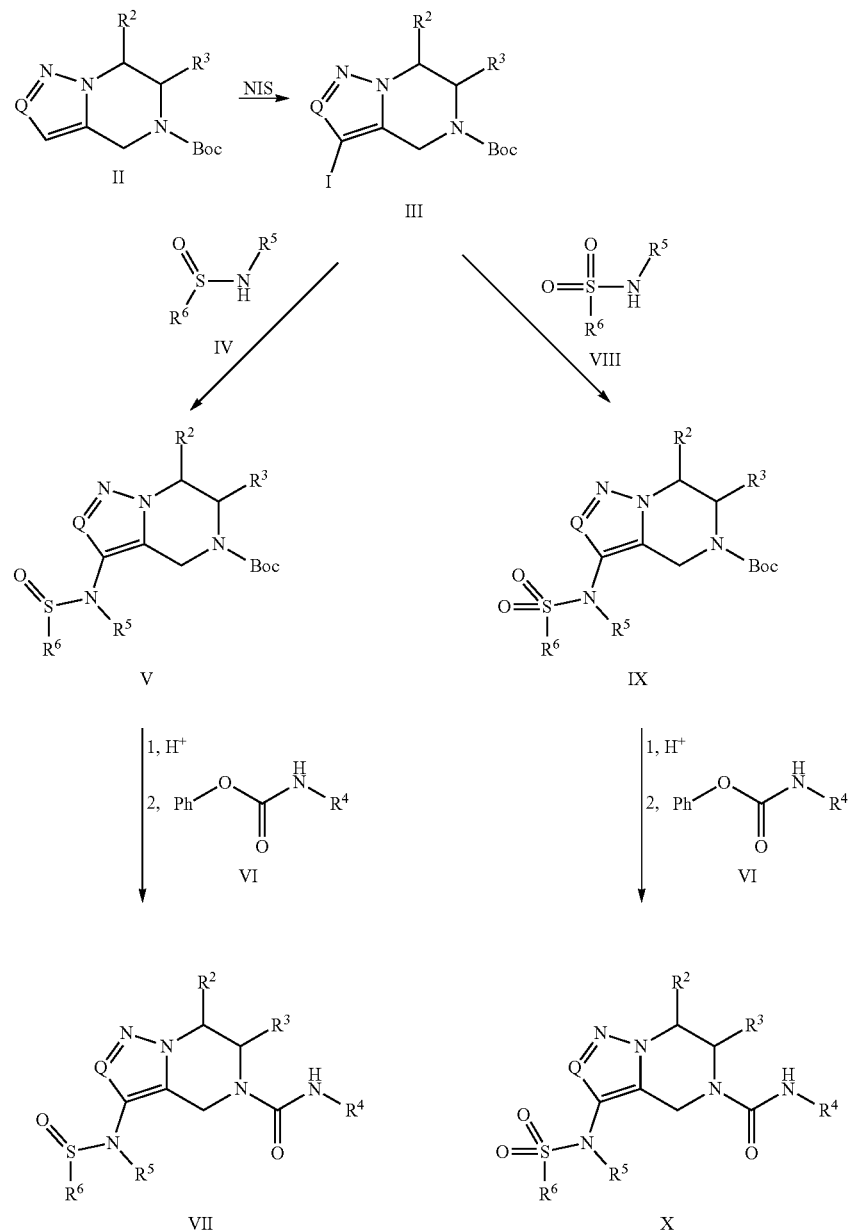

$R^5$ and $R^6$ together with the nitrogen and sulfur atoms they are attached to form a 4-10 membered heterocyclyl.

The compound of formula (VII) and (X) can be prepared according to Scheme 1. Bicycle (II) is treated with iodinating reagents, such as N-iodosuccinimide, to give iodide (III), which undergoes copper catalyzed coupling reaction with sulfinamide (IV) in the presence of a copper catalyst, such as CuI, affords compound of formula (V). Deprotection of intermediate (V) in acidic condition, such as HC in EtOAc and TFA in DCM, followed by reaction with phenyl carbamate (VI) affords final compound of formula (VII). On the other hand, copper catalyzed coupling reaction between iodide (III) and sulfonamide (VIII) affords compound of formula (IX), which undergoes deprotection in acidic condition, such as HCl in EtOAc and TFA in DCM, followed by reaction with phenyl carbamate (VI) to afford final compound of formula (X).

This invention also relates to a process for the preparation of a compound of formula (I), (VII) or (X) comprising any one of the following steps:
(a) the reaction of compound of formula (V),

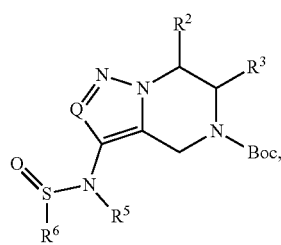

(V)

with acid followed by reaction with phenyl carbamate (VI);
(b) the reaction of compound of formula (IX),

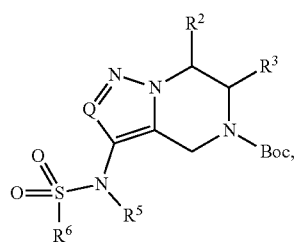

(IX)

with acid followed by reaction with phenyl carbamate (VI);
In step (a) and (b), the acid can be, for example, HCl in EtOAc or TFA in DCM.

A compound of formula (I), (VII) or (X) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to the suppression of serum HBV DNA levels, or HBeAg seroconversion to HBeAb, or HBsAg loss, or normalization of alanine aminotransferase levels and improvement in liver histology. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 mg to 1000 mg of the compound of the invention compounded with about 30 mg to 90 mg anhydrous lactose, about 5 mg to 40 mg sodium croscarmellose, about 5 mg to 30 mg polyvinylpyrrolidone (PVP) K30, and about 1 mg to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I), or a stereoisomer or pharmaceutically acceptable salt thereof. In a further embodiment includes a pharmaceutical composition comprising a compound of formula (I), or a stereoisomer or pharmaceutically acceptable salt thereof, together with a pharmaceutically acceptable carrier or excipient.

Indications and Methods of Treatment

The compounds of the invention can inhibit HBV's DNA synthesis and reduce HBV DNA levels. Accordingly, the compounds of the invention are useful for the treatment or prophylaxis of HBV infection.

The invention relates to the use of a compound of formula (I) for the treatment or prophylaxis of HBV infection.

The use of a compound of formula (I) for the preparation of medicaments useful in the treatment or prophylaxis diseases that are related to HBV infection is an object of the invention.

The invention relates in particular to the use of a compound of formula (I) for the preparation of a medicament for the treatment or prophylaxis of HBV infection.

Another embodiment includes a method for the treatment or prophylaxis of HBV infection which method comprises administering an effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations used herein are as follows:
DCE: 1,2-dichloroethylene or
DIPEA: N,N-diisopropylethylamine
EA or EtOAc: ethyl acetate
$EC_{50}$: half maximal effective concentration
HATU: 1-[Bis(dimethylamino)methylene]-1H-1,2,3-triazolo[4,5-b]pyridinium 3-oxid hexafluorophosphate
HPLC: high performance liquid chromatography
LCMS liquid chromatography-mass spectrometry
min(s): minute(s)
MS: mass spectrometry
MsCl: methanesulfonyl chloride
NIS: N-iodosuccinimide
NMP 1-methylpyrrolidin-2-one
MeMgBr methylmagnesium bromide
obsd. observed
Pd(dppf)Cl$_2$ [1,1'-bis(diphenylphosphino)ferrocene]dichloropalladium(II)
PE: petroleum ether
prep-HPLC: preparative high performance liquid chromatography
prep-TLC: preparative thin layer chromatography
psi: pounds per square inch
SFC: supercritical fluid chromatography
TEA: trimethylamine
Tf$_2$O trifluoromethanesulfonic anhydride
pgRNA: pre-genomic RNA
qPCR: quantitative polymerase chain reaction
v/v volume ratio General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 µm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C$_{18}$ (5 µm, OBD™ 30×100 mm) column or SunFire™ Prep-C18 (5 µm, OBD™ 30×100 mm) column. Waters AutoP purification System (Column: XBridge™ Prep-C18, 30×100 mm, Sample Manager 2767, Pump 2525, Detector: Micromass ZQ and UV 2487, solvent system: acetonitrile and 0.1% ammonium hydroxide in water). LC/MS spectra of compounds were obtained using a LC/MS (Waters™ Alliance 2795-Micromass ZQ), LC/MS conditions were as follows (running time 6 mins):

Acidic condition: A: 0.1% formic acid in H$_2$O; B: 0.1% formic acid in acetonitrile;

Basic condition: A: 0.1% NH$_3$.H$_2$O in H$_2$O; B: acetonitrile;

Neutral condition: A: H$_2$O; B: acetonitrile.

Mass spectra (MS): generally only ions which indicate the parent mass are reported, and unless otherwise stated the mass ion quoted is the positive mass ion (MH)$^+$.

NMR Spectra were obtained using Bruker Avance 400 MHz.

The microwave assisted reactions were carried out in a Biotage Initiator Sixty microwave synthesizer.

All reactions involving air-sensitive reagents were performed under an argon or nitrogen atmosphere. Reagents were used as received from commercial suppliers without further purification unless otherwise noted.

The following examples are intended to illustrate the meaning of the present invention but should by no means represent a limitation within the meaning of the present invention:

Preparative Examples

The invention will be more fully understood by reference to the following examples. They should not, however, be construed as limiting the scope of the invention.

Intermediate I-1 tert-Butyl (6S)-3-iodo-6-methyl-6,7-dihydro-4H-pyrazolo[1,5-a]pyrazine-5-carboxylate

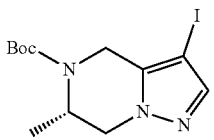 [SMILES: C[C@H]1Cn2ncc(I)c2CN1C(=O)OC(C)(C)C]

Intermediate I-1 was prepared according to the following scheme:

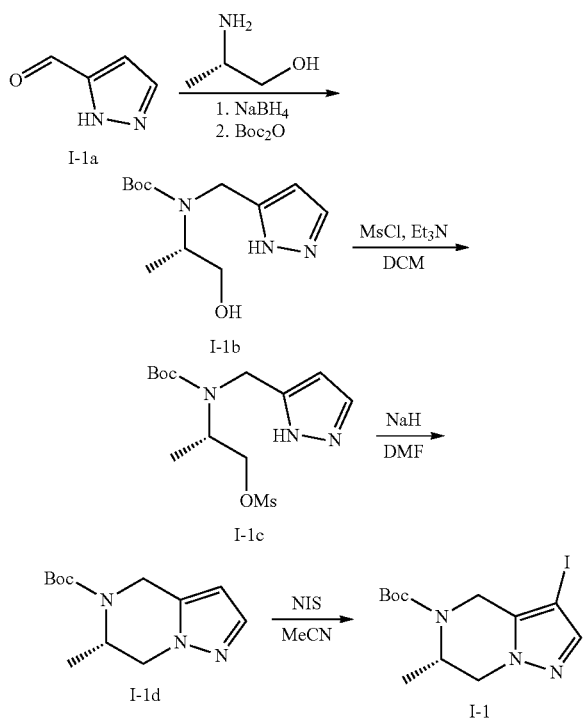

Step 1: Preparation of tert-butyl N-[(1S)-2-hydroxy-1-methyl-ethyl]-N-(1H-pyrazol-5-ylmethyl)carbamate (Compound I-1b)

To a solution of 1H-pyrazole-5-carbaldehyde (compound I-1a, 54.0 g, 562.5 mmol) in MeOH (300 mL) was added (2S)-2-aminopropan-1-ol (41.2 g, 675 mmol). The reaction mixture was stirred at 25° C. for 1 hour. NaBH$_4$ (25.9 g, 675 mmol) was added at 0° C. and the reaction mixture was stirred for another hour followed by the addition of H$_2$O (300 mL) and Boc$_2$O (147.1 g, 675 mmol). The resulting mixture was stirred at room temperature for 12 hours, and extracted with EtOAc (600 mL). The organic layer was dried over anhydrous Na$_2$SO$_4$, filtered and concentrated. The residue was purified by column chromatography (eluting with 0%~5% MeOH in DCM) to afford compound I-1b (80 g) as a colorless oil. MS obsd. (ESI$^+$) [(M+H)$^+$]: 334.

Step 2: Preparation of [(2S)-2-[tert-butoxycarbonyl(1H-pyrazol-5-ylmethyl)amino]propyl]methanesulfonate (Compound I-1c)

To a mixture of tert-butyl N-[(1S)-2-hydroxy-1-methyl-ethyl]-N-(1H-pyrazol-5-ylmethyl)carbamate (compound I-1b, 80 g, 117.2 mmol) and Et$_3$N (100.5 g, 995.6 mmol) in DCM (800 mL) was added MsCl (57.3 g, 497.8 mmol) slowly at 0° C. The resulting mixture was stirred at room temperature for 2 hours, then washed with water (500 mL), brine (500 mL), and dried over anhydrous Na$_2$SO$_4$. The organic layer was concentrated to afford compound I-1c (100 g, crude), which was used directly in next step.

Step 3: Preparation of tert-butyl (6S)-6-methyl-6,7-dihydro-4H-pyrazolo[1,5-a]pyrazine-5-carboxylate (Compound I-1d)

To a solution of [(2S)-2-[tert-butoxycarbonyl(1H-pyrazol-5-ylmethyl)amino]propyl]methanesulfonate (compound I-1c, 100 g, 313.4 mmol) in DMF (1000 mL) was added NaH (15 g, 376.2 mmol) in portions at 0° C. The reaction mixture was then stirred at room temperature for 12 hours, poured into water (2000 mL) and extracted with EtOAc (1000 mL) twice. The combined organic layer was concentrated and the residue was purified by column chromatography (eluting with 10%~80% EtOAc in petroleum ether) to afford compound I-1d (18 g) as a colorless oil. MS obsd. (ESI$^+$) [(M+H)$^+$]: 238.

Step 4: Preparation of tert-butyl (6S)-3-iodo-6-methyl-6,7-dihydro-4H-pyrazolo[1,5-a]pyrazine-5-carboxylate (Intermediate I-1)

To a solution of tert-butyl 6-methyl-6,7-dihydro-4H-pyrazolo[1,5-a]pyrazine-5-carboxylate (compound I-1d, 3.3 g, 14.8 mmol) in CH$_3$CN (40 mL) was added NIS (5.0 g, 22.1 mmol) slowly. The reaction mixture was stirred at room temperature for 16 hours and then extracted with EtOAc (50 mL), washed with brine (50 mL). The organic layer was dried over Na$_2$SO$_4$ and concentrated, and the residue was purified by column chromatography (eluting with 10%~80% EtOAc in petroleum ether) to afford intermediate I-1 (4.8 g) as a white solid.

Intermediate I-2

Phenyl N-(3,4,5-trifluorophenyl)carbamate

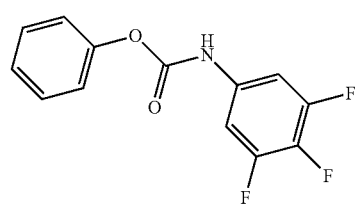 [SMILES: O=C(Nc1cc(F)c(F)c(F)c1)Oc1ccccc1]

Intermediate I-2 was prepared according to the following scheme:

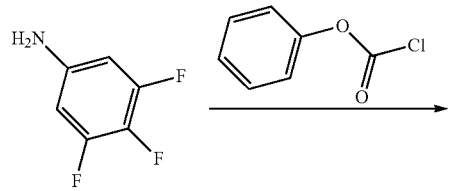

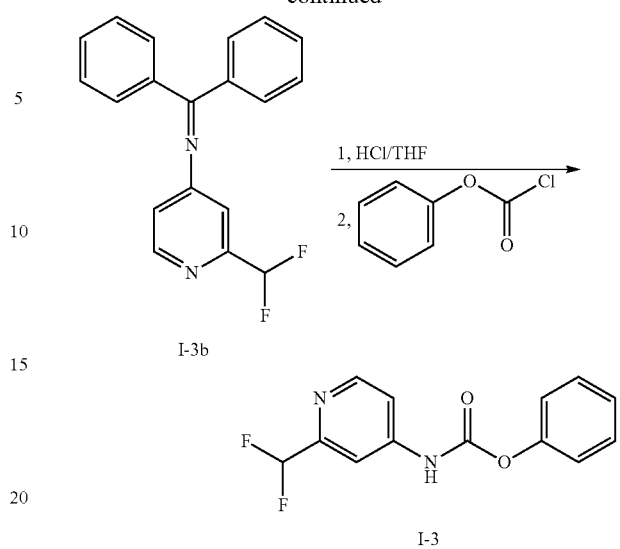

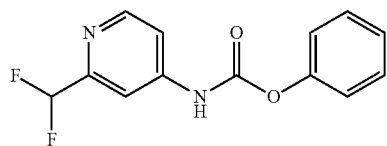 [SMILES: O=C(Nc1ccnc(C(F)F)c1)Oc1ccccc1]

I-2

To a solution of 3,4,5-trifluoroaniline (1.47 g, 10 mmol) in DCM (30 mL) was added DIPEA (2 mL, 12 mmol), followed by adding phenyl chloroformate (1.4 mL, 11 mmol) dropwise at 0° C. After addition the reaction mixture was warmed to room temperature and stirred overnight. The reaction mixture was diluted with DCM, washed with water. The organic phase was separated, dried over anhydrous Na$_2$SO$_4$ and concentrated. The residue was purified by column to give intermediate I-2 (1.87 g) as a white solid. MS obsd. (ESI$^+$) [(M+H)$^+$]: 268.

Intermediate I-3

Phenyl N-[2-(difluoromethyl)-4-pyridyl]carbamate

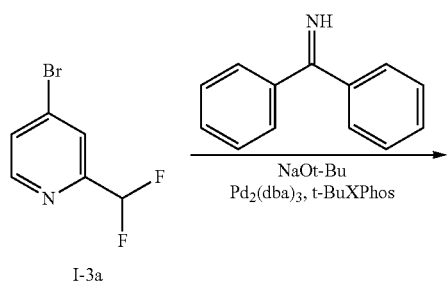

Intermediate I-3 was prepared according to the following scheme:

To a mixture of 4-bromo-2-(difluoromethyl)pyridine (compound I-3a, 416 mg, 2.0 mmol) and diphenylmethanimine (725 mg, 4.0 mmol) in toluene (15 mL) were added Pd$_2$(dba)$_3$ (92 mg, 0.1 mmol), t-BuXPhos (85 mg, 0.2 mmol) and NaOt-Bu (577 mg, 6 mmol). The reaction mixture was heated at 100° C. for 2 hours. The reaction mixture was cooled down, diluted with EtOAc (30 mL), and washed with water. The organic layer was separated and concentrated to give crude compound I-3b (617 mg). MS obsd. (ESI$^+$) [(M+H)$^+$]: 309. Compound I-3b (617 mg, 2 mmol) was dissolved in THF (10 mL) and hydrochloride acid (2 mL, 12 M). The resulting mixture was stirred at room temperature for 2 hours, and then concentrated. The residue was dissolved in DCM (5 mL), followed by addition of DIPEA (1 mL, 5.8 mmol) and phenyl carbonochloridate (251 μL, 2.0 mmol) at 0° C. The resulting mixture was stirred at room temperature for 2 hours, and then poured into water (20 mL), and extracted with EtOAc (20 mL) twice. The organic layers were combined and concentrated, and the residue was purified by column chromatography (eluting with 0%~20% EtOAc in petroleum ether) to afford intermediate I-3 (264 mg) as a white solid. MS obsd. (ESI$^+$) [(M+H)$^+$]: 265.

Intermediate I-4

Phenyl N-(2-chloro-4-pyridyl)carbamate

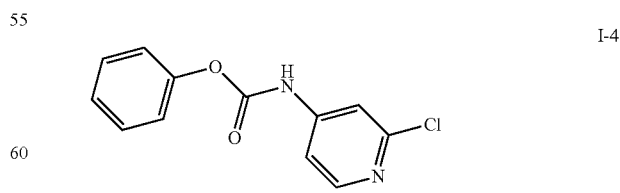

Intermediate I-4 was prepared in analogy to intermediate I-2 by using 2-chloropyridin-4-amine instead of 3,4,5-trifluoroaniline. Intermediate I-4 (1.74 g) was obtained as a white solid. MS obsd. (ESI$^+$) [(M+H)$^+$]: 249.

Intermediate I-5

Phenyl N-(4-chloro-3-fluoro-phenyl)carbamate

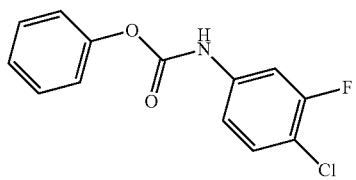 [SMILES: O=C(Nc1ccc(Cl)c(F)c1)Oc1ccccc1]

Intermediate I-5 was prepared according to the following scheme:

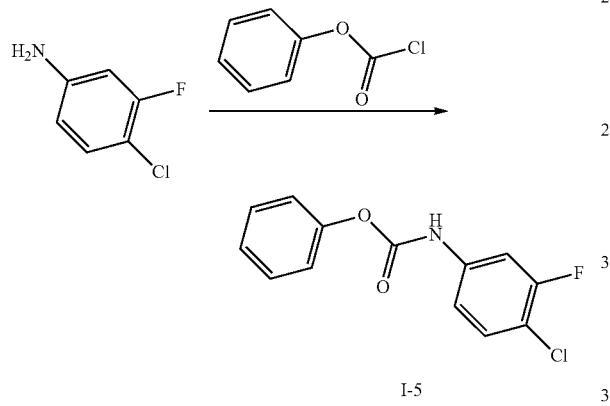

To a mixture of 4-chloro-3-fluoroaniline (1.0 g, 6.87 mmol) and phenyl chloroformate (1.0 g, 6.87 mmol) in DCM (64 mL) was added Et$_3$N (1.4 g, 13.74 mmol). The mixture was stirred at 20° C. for 4 hours, and then concentrated under reduced pressure. The residue was partitioned between EtOAc (50 mL) and water (50 mL). The organic layer was washed with brine, dried over anhydrous Na$_2$SO$_4$ and concentrated under reduced pressure. The residue was purified by chromatography on silica gel to give phenyl N-(4-chloro-3-fluoro-phenyl)carbamate (intermediate I-5, 550 mg) as a white solid. MS obsd. (ESI$^+$) [(M+H)$^+$]: 266.

Intermediate I-6

Phenyl N-(4-fluoro-3-methyl-phenyl)carbamate

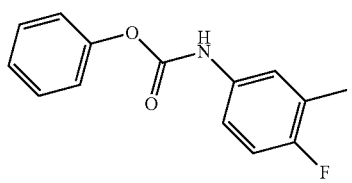 [SMILES: Cc1cc(NC(=O)Oc2ccccc2)ccc1F]

Intermediate I-6 was prepared according to the following scheme:

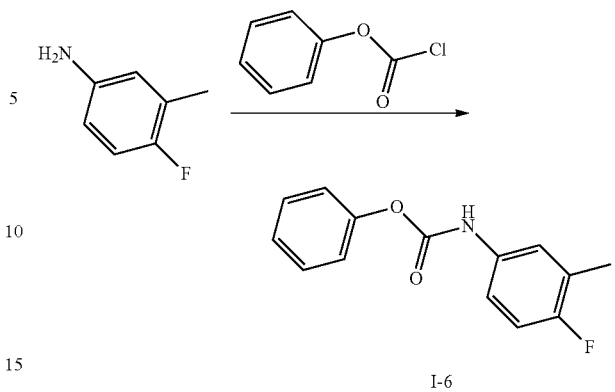

To a mixture of 4-fluoro-3-methylaniline (1.0 g, 8.0 mmol) and phenyl chloroformate (1.25 g, 8.0 mmol) in DCM (70 mL) was added Et$_3$N (1.6 g, 16 mmol). The mixture was stirred at 20° C. for 16 hours, and then concentrated under reduced pressure. The residue was dissolved in EtOAc (20 mL), followed by addition of PE (20 mL). The resulting suspension was stirred for 5 mins, and then filtered. The filtrate was concentrated under reduced pressure and the residue was recrystallized with EtOAc and PE to give phenyl N-(4-fluoro-3-methyl-phenyl)carbamate (intermediate I-6, 730 mg) as a white solid. MS obsd. (ESI$^+$) [(M+H)$^+$]: 246.

Intermediate I-7

Phenyl N-(3-cyano-4-fluoro-phenyl)carbamate

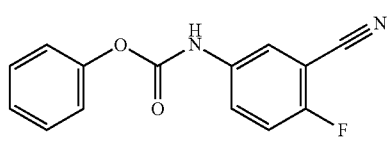 [SMILES: N#Cc1cc(NC(=O)Oc2ccccc2)ccc1F]

Intermediate I-7 was prepared in analogy to intermediate I-6 by using 5-amino-2-fluoro-benzonitrile instead of 4-fluoro-3-methylaniline. Intermediate I-7 (200 mg) was obtained as a white solid. MS obsd. (ESI$^+$) [(M+H)$^+$]: 257.

Intermediate I-8

Phenyl N-[4-fluoro-3-(trifluoromethyl)phenyl]carbamate

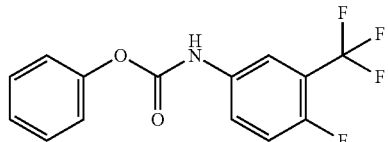

Intermediate I-8 was prepared in analogy to compound I-5 by using 4-fluoro-3-(trifluoromethyl) aniline instead of 4-chloro-3-fluoroaniline. Intermediate I-8 (100 mg) was obtained as a white solid. MS obsd. (ESI$^+$) [(M+H)$^+$]: 300.

Intermediate I-9

Phenyl N-(2-fluorophenyl)carbamate

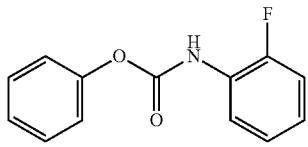 [SMILES: O=C(Nc1ccccc1F)Oc1ccccc1]

Intermediate I-9 was prepared in analogy to compound I-5 by using 2-fluoroaniline instead of 4-chloro-3-fluoroaniline. Intermediate I-9 (100 mg) was obtained as a white solid. MS obsd. (ESI$^+$) [(M+H)$^+$]: 232.

Intermediate I-10

Phenyl N-(1,3-benzothiazol-6-yl)carbamate

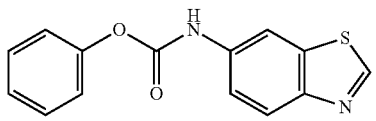 [SMILES: O=C(Nc1ccc2ncsc2c1)Oc1ccccc1]

Intermediate I-10 was prepared in analogy to compound I-5 by using 1,3-benzothiazol-6-amine instead of 4-chloro-3-fluoroaniline. Intermediate I-10 (50 mg) was obtained as a white solid. MS obsd. (ESI$^+$) [(M+H)$^+$]: 271.

Intermediate I-11

Phenyl N-(3-thienyl)carbamate

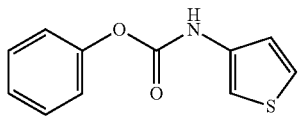 [SMILES: O=C(Nc1ccsc1)Oc1ccccc1]

Intermediate I-11 was prepared in analogy to compound I-5 by using thiophen-3-amine instead of 4-chloro-3-fluoroaniline. Intermediate I-11 (150 mg) was obtained as a white solid. MS obsd. (ESI$^+$) [(M+H)$^+$]: 220.

Intermediate I-12

Phenyl N-benzylcarbamate

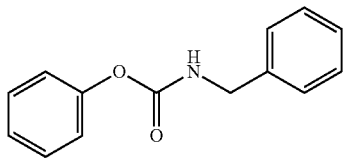 [SMILES: O=C(NCc1ccccc1)Oc1ccccc1]

Intermediate I-12 was prepared in analogy to compound I-6 by using phenylmethanamine instead of 4-fluoro-3-methylaniline. Intermediate I-12 (900 mg) was obtained as a white solid. MS obsd. (ESI$^+$) [(M+H)$^+$]: 228.

Intermediate I-13

3-Methyl-1,2-thiazolidine 1,1-dioxide

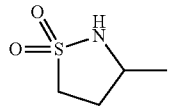

Intermediate I-13 was prepared according to the following scheme:

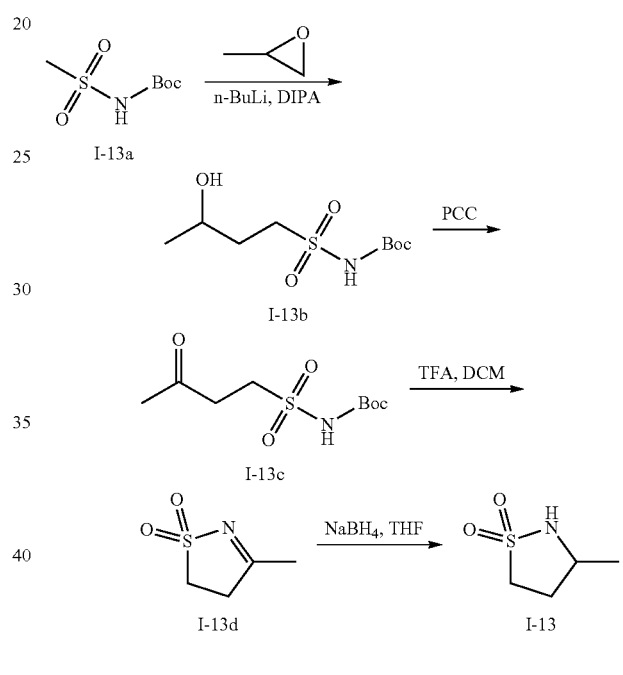

Step 1: Preparation of tert-butyl N-(3-hydroxybutylsulfonyl)carbamate (Compound I-13b)

To a solution of diisopropylamine (15.54 g, 163.66 mmol) in THF (150 mL) was added n-BuLi (61.5 mL, 153.75 mmol, 2.5 M in hexane) at −78° C. The mixture was stirred at −78° C. for 20 mins. Then a solution of tert-butyl methylsulfonylcarbamate (compound I-13a, 15.0 g, 76.8 mmol) in THF (150 mL) was added to the above mixture drop-wise over a period of 20 mins. The mixture was stirred at −50° C. for 30 mins, followed by addition of a solution of propylene oxide (5.58 g, 96.03 mmol, 6.72 mL) in THF (90 mL) over 30 mins at −78° C. The mixture was allowed to warm up to rt and stirred for 15 hrs. The mixture was poured into aqueous NH$_4$Cl solution (210 mL). The resulting precipitate was collected and dissolved with water, followed by acidification with 2 M HCl to pH=3. The resulting aqueous mixture was extracted with DCM (100 mL) for 5 times. The combined organic layer was washed with brine, dried over anhydrous Na$_2$SO$_4$ and concentrated under reduced pressure. The residue was purified by column chromatography to give compound I-13b (17 g) as a colorless oil. MS obsd. (ESI⁺) [(M+H)⁺]: 254

Step 2: Preparation of tert-butyl N-(3-oxobutylsulfonyl)carbamate (Compound I-13c)

A mixture of tert-butyl N-(3-hydroxybutylsulfonyl)carbamate (compound I-13b, 17.0 g, 67.1 mmol) and pyridinium chlorochromate (30.4 g, 140.9 mmol) in DCM (500 mL) was stirred at 15° C. for 16 hours. The reaction mixture was filtered through Celite. The filtrate was concentrated under reduced pressure and the residue was purified by column chromatography to give crude compound I-13c (15 g) as a black solid. MS obsd. (ESI⁺) [(M+H)⁺]: 252

Step 3: Preparation of 3-methyl-4,5-dihydroisothiazole 1,1-dioxide (Compound I-13d)

A mixture of tert-butyl N-(3-oxobutylsulfonyl)carbamate ((compound I-13c, 10.0 g, 39.8 mmol) and TFA (15.4 g, 159.2 mmol) in DCM (375 mL) was refluxed for 48 hrs. The mixture was concentrated under reduced pressure and the residue was dissolved in EtOH (50 mL). The solution was concentrated under reduced pressure to leave a 25 mL mixture, which was cooled to −20° C. The mixture was filtered. The filter cake was washed with cold EtOH (25 mL, −20° C.) and dried under reduced pressure to give compound I-13d (3.7 g) as a white solid. MS obsd. (ESI⁺) [(M+H)⁺]: 134

Step 4: Preparation of 3-methyl-1,2-thiazolidine 1,1-dioxide (Intermediate I-13)

To a solution of 3-methyl-4,5-dihydroisothiazole 1,1-dioxide (3.7 g. 27.7 mmol) in THF (90 mL) was added NaBH₄ (1.2 g, 30.5 mmol) portion wise at −20° C. The mixture was stirred at −20° C. for 20 mins under N₂ atmosphere, and then poured into saturated NaHCO₃ solution (500 mL). The resulting mixture was extracted with EtOAc (400 mL) for 5 times. The combined organic layers were washed with brine, dried over anhydrous Na₂SO₄ and concentrated under reduced pressure. The residue was purified by column chromatography to give 3-methyl-1,2-thiazolidine 1,1-dioxide (intermediate I-13, 2.5 g) as a colorless oil. MS obsd. (ESI⁺) [(M+H)⁺]:

Intermediate I-14

1,2-Thiazolidine 1-oxide

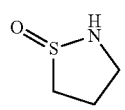

Intermediate I-14 was prepared according to the following scheme:

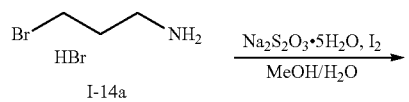

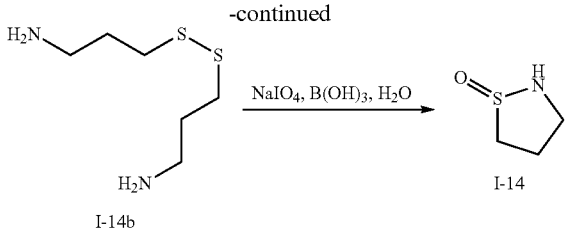

Step 1: Preparation of 3-(3-aminopropyldisulfanyl)propan-1-amine (Compound I-14b)

A solution of 3-bromopropan-1-amine hydrobromide (30 g, 137 mmol) and Na₂S₂O₃.5H₂O (37.4 g, 151 mmol) in MeOH/H₂O (200 mL, V/V=1:1) was heated at 90° C. with stirring for 12 hrs. Iodine (19.1 g, 75.4 mmol) in MeOH (200 mL) was slowly added to the refluxing solution through a dropping funnel over 10 hrs. The mixture was concentrated under reduced pressure. The residue was dissolved in 6 N aqueous NaOH (100 mL) and the resulting solution was extracted with DCM (500) twice. The combined organic layer was concentrated under reduced pressure. The residue was treated with a solution of HCl in EA (100 mL, 4 N) and then filtered. The filter cake was dissolved in 6 N aqueous NaOH (100 mL) and the solution was extracted with DCM (500 mL) twice. The combined organic layer was dried over anhydrous Na₂SO₄ and concentrated under reduced pressure to give compound I-14b (10.6 g) as a yellow oil. MS obsd. (ESI⁺) [(M+H)⁺]: 181

Step 2: Preparation of 1,2-thiazolidine 1-oxide (Intermediate I-14)

To a solution of 3-(3-aminopropyldisulfanyl)propan-1-amine (3.0 g, 16.6 mmol) and NaIO₄ (16 g, 75 mmol) in H₂O (500 mL) was added B(OH)₃/H₂O (0.2 M) to pH=8. The mixture was stirred at 25° C. for 3 days, and then filtered. The filtrate was extracted with DCM (100 mL) for three times. The combined organic layer was dried over anhydrous Na₂SO₄ and concentrated under reduced pressure. The residue was purified by column chromatography to give 1,2-thiazolidine 1-oxide (intermediate I-14, 60 mg) as a yellow oil. MS obsd. (ESI⁺) [(M+H)⁺]: 106.

Intermediate I-15

1,1-Dioxo-1,2-thiazolidin-4-ol

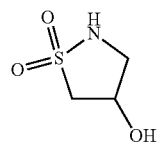

Intermediate I-15 was prepared according to the following scheme:

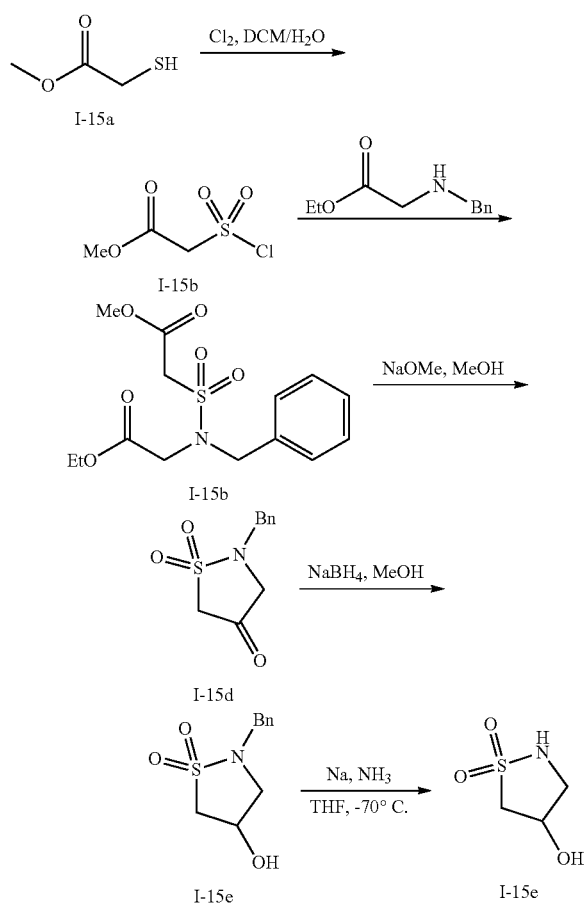

Step 1: Preparation of methyl 2-chlorosulfonylacetate (Compound I-15b)

To a solution of methyl 2-mercaptoacetate (compound I-15a, 34 g, 320 mmol) in DCM (50 mL) was added H₂O (150 mL). Chlorine gas was bubbled gently through the solution, maintaining the temperature below 5° C. until the solution maintained a slight green coloration over 4 hours. The solution was extracted with DCM (100 mL) twice. The combined organic layer was dried over anhydrous Na₂SO₄ and concentrated to give compound I-15b (56.6 g, crude) as a yellow oil, which was used in next step directly without further purification.

Step 2: Preparation of ethyl 2-[benzyl-(2-methoxy-2-oxo-ethyl)sulfonyl-amino]acetate (Compound I-15c)

A mixture of ethyl 2-(benzylamino)acetate (30.9 g, 159.9 mmol), methyl 2-chlorosulfonylacetate (compound I-15b, 27.6 g, 159.9 mmol) and triethylamine (32.4 g, 319.8 mmol) in DCM (300 mL) was stirred at 18° C. for 12 hours. The mixture was diluted with DCM (500 mL), and washed with 1 N hydrochloric acid (200 mL) twice. The organic layer was dried over anhydrous Na₂SO₄, and concentrated under reduced pressure. The residue was purified by chromatography on silica gel to give compound I-15c (25.1 g) as a yellow oil. MS obsd. (ESI⁺) [(M+H)⁺]: 330.

Step 3: Preparation of 2-benzyl-1,1-dioxo-1,2-thiazolidin-4-one (Compound I-15d)

To a solution of Na (7.0 g, 303.6 mmol) in MeOH (400 mL) was added a solution of ethyl 2-[benzyl-(2-methoxy-2-oxo-ethyl)sulfonyl-amino]acetate (compound I-15c, 20 g, 60.7 mmol) in MeOH (100 mL) slowly. The reaction mixture was stirred at 18° C. for 4 hours, and then quenched by adding H₂O (50 mL). The resulting mixture was acidified with concentrated HCl to pH=3, and then stirred at 18° C. for 4 hours. The mixture was concentrated under reduced pressure, and the residue was purified by chromatography on silica gel to give compound I-15d (1.8 g) as a yellow solid. MS obsd. (ESI⁺) [(M+H)⁺]: 226.

Step 4: Preparation of 2-benzyl-1,1-dioxo-1,2-thiazolidin-4-ol (Compound I-15e)

To a mixture of 2-benzyl-1,1-dioxo-1,2-thiazolidin-4-one (compound I-15d, 200 mg, 0.89 mmol) in anhydrous MeOH (3 mL) was added NaBH₄ (169 mg, 4.4 mmol). The reaction mixture was stirred at 15° C. for 1 hour, and then quenched with H₂O (2 mL). The resulting mixture was purified by prep-HPLC to give compound I-15e (170 mg) as a yellow oil.

Step 5: Preparation of 1,1-dioxo-1,2-thiazolidin-4-ol (Intermediate I-15)

Na (14 mg, 3.5 mmol) was added to Liquid NH₃ (5 mL) at −70° C. The mixture was stirred at −70° C. for 10 mins, followed by addition of a solution of 2-benzyl-1,1-dioxo-1,2-thiazolidin-4-ol (compound I-15e, 80 mg, 0.35 mmol) in THF (1 mL). The reaction mixture was stirred at −70° C. for 3 hours, then quenched by adding an aqueous NH₄Cl solution (5 mL). The mixture was warmed up to 15° C., and then concentrated, followed by addition of THF (30 mL). The resulting mixture was stirred for 20 mins, and filtered. The filtrate was concentrated under reduced pressure to give crude intermediate I-15 (50 mg), which was used without further purification. MS obsd. (ESI⁺) [(M+H)⁺]: 138.

Intermediate I-16

2-Benzyl-1,2,5-thiadiazolidine 1,1-dioxide

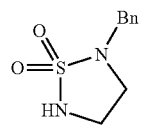

Intermediate I-16 was prepared according to the following scheme:

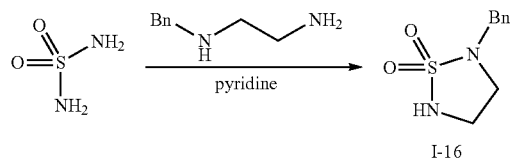

To a refluxing solution of sulfamide (2.0 g, 20.8 mmol) in anhydrous pyridine (60 mL) was added drop-wise N-benzylethane-1,2-diamine (3.1 g, 20.8 mmol) over 2 hours. The resulting mixture was refluxed for further 10 hours. The mixture was concentrated under reduced pressure, and the residue was purified by chromatography on silica gel to give intermediate I-16 (2.2 g) as a yellow oil. MS obsd. (ESI+) [(M+H)+]: 213.

Intermediate I-17

2-Methyl-1,2,5-thiadiazolidine 1,1-dioxide

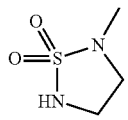

Intermediate I-17 was prepared according to the following scheme:

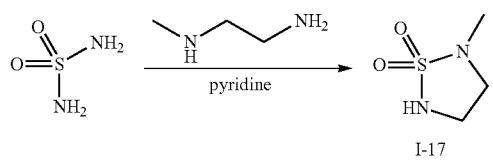

To a mixture of sulfamide (5 g, 52.1 mmol) in pyridine (120 mL) was added a solution of n-methylethylenediamine (3.85 g, 52.1 mmol) in pyridine (30 mL) at 100° C. The mixture was stirred at 100° C. for 16 hours, and then concentrated under reduced pressure. The residue was purified by column chromatography to give intermediate I-17 (2.7 g) as a colorless oil. $^1$H NMR (400 MHz, CDCl$_3$) δ 4.37 (brs, 1H), 4.45-4.58 (m, 2H), 3.34-3.42 (m, 2H), 2.76 (s, 3H).

Intermediate I-18

(3S)-3-Methylthiazetidine 1,1-dioxide

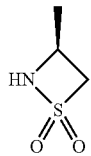

Intermediate I-18 was prepared according to the following scheme:

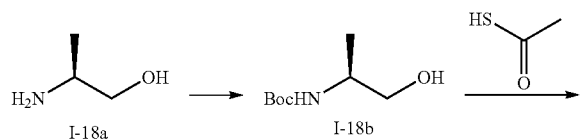

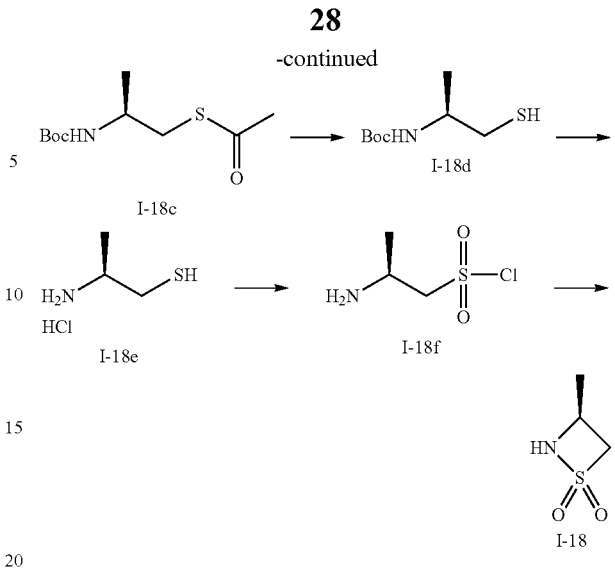

Step 1: Preparation of tert-butyl N-[(1S)-2-hydroxy-1-methyl-ethyl]carbamate (Compound I-18b)

A mixture of (2S)-2-aminopropan-1-ol (compound I-18a, 10 g, 133 mmol) in dioxane (100 mL) and saturated aqueous NaHCO$_3$ solution (100 mL) was added Boc$_2$O (29.1 g, 133 mmol) at 20° C. The mixture was stirred at 20° C. for 3 hours, then extracted with EtOAc (100 mL) for 3 times. The combined organic layer was dried over anhydrous Na$_2$SO$_4$, filtered and concentrated to give compound I-18b (18.5 g) as a yellow oil.

Step 2: Preparation of S-[(2S)-2-(tert-butoxycarbonylamino)propyl]ethanethioate (Compound I-18c)

The mixture of tert-butyl N-[(1 S)-2-hydroxy-1-methyl-ethyl]carbamate (compound I-18b, 10 g, 57.1 mmol) and TEA (6.4 g, 62.8 mmol) in DCM (100 mL) was added MsCl (7.2 g, 62.8 mmol) at 0° C. After addition, the mixture was stirred at 20° C. for 1 hour, then quenched with saturated aqueous NaHCO$_3$. The organic layer was separated and the aqueous layer was extracted with EtOAc (30 mL) for three times. The combined organic layer was dried over anhydrous Na$_2$SO$_4$, filtered and concentrated. The residue (11 g) was dissolved in DMF (100 mL), followed by addition of ethanethioic S-acid (5 g, 65 mmol) and Cs$_2$CO$_3$ (21.2 g, 65.1 mmol). The mixture was stirred at 20° C. for 16 hours, then filtered and the filtrate was concentrated. The residue was purified by column chromatography to give compound I-18c (7.5 g) as a yellow oil. $^1$H NMR (400 MHz, CHLOROFORM-d) δ 4.56 (br s, 1H), 3.87 (br s, 1H), 3.04 (q, 2H), 2.37 (s, 3H), 1.45 (s, 8H), 1.60-1.37 (m, 1H), 1.18 (d, 3H).

Step 3: Preparation of tert-butyl N-[(1S)-1-methyl-2-sulfanyl-ethyl]carbamate (Compound I-18d)

To the mixture of S-[(2S)-2-(tert-butoxycarbonylamino)propyl]ethanethioate (compound I-18c, 7.5 g, 32 mmol) in MeOH (100 mL) was added NaOH (4 g, 100 mmol). The mixture was stirred at 20° C. for 16 hours, then concentrated under reduce pressure. The residue was dissolved with H$_2$O, and adjusted to pH=7. The resulting mixture was extracted with EtOAc (20 mL) for 3 times. The combined organic layer was dried over anhydrous Na$_2$SO$_4$, filtered and concentrated. The residue was purified by column chromatography to give compound I-18d (5.3 g) as yellow oil. $^1$H NMR (400 MHz, CHLOROFORM-d) δ 4.69 (br s, 1H), 3.87 (br s, 1H), 2.67 (br dd, 2H), 1.46 (s, 9H), 1.35-1.28 (m, 1H), 1.20 (d, 3H).

Step 4: Preparation of (2S)-2-aminopropane-1-thiol hydrochloride (Compound I-18e)

A mixture of tert-butyl N-[(1S)-1-methyl-2-sulfanyl-ethyl]carbamate (compound I-18d, 0.52 g, 2.7 mmol) in HCl/EtOAc (5.0 mL) was stirred at 25° C. for 2 hours, then concentrated under reduced pressure to afford compound I-18e (0.5 g, crude) as a white solid. MS obsd. (ESI$^+$) [(M+H)$^+$]: 92.

Step 5: Preparation of (2S)-2-aminopropane-1-sulfonyl chloride hydrochloride (Compound I-18f)

To a mixture of (2S)-2-aminopropane-1-thiol hydrochloride (compound I-18e, 340 mg, 2.7 mmol) in methanol (25 mL) was blown chlorine gas for 30 minutes at 0° C. The reaction mixture was stirred at 15° C. for 2 hours, then purged with nitrogen. The mixture was concentrated to afford compound I-18f (0.5 g, crude), which was used for next step without purification. MS obsd. (ESI$^+$) [(M+H)$^+$]: 158.

Step 6: Preparation of (3S)-3-methylthiazetidine 1,1-dioxide (Intermediate I-18)

To a solution of (2S)-2-aminopropane-1-sulfonyl chloride hydrochloride (compound I-18f, 0.4 g, 2.1 mmol) in DCM (25 mL) was added TEA (0.64 g, 6.3 mmol). The mixture was stirred at 15° C. for 15 hours, then concentrated. The residue was triturated in EtOAc (30 mL), then filtered. The filtrated was concentrated to afford intermediate I-18 (0.25 g) as a yellow oil. MS obsd. (ESI$^+$) [(M+H)$^+$]: 122.

Intermediate I-19

(4S)-2-[(4-methoxyphenyl)methyl]-4-methyl-1,2,5-thiadiazolidine 1,1-dioxide

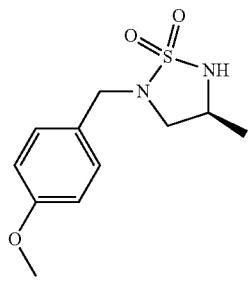 [SMILES: COc1ccc(CN2C[C@H](C)NS2(=O)=O)cc1]

Intermediate I-19 was prepared according to the following scheme:

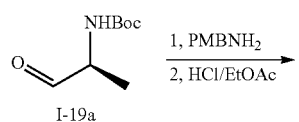

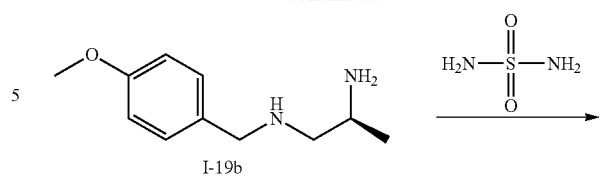

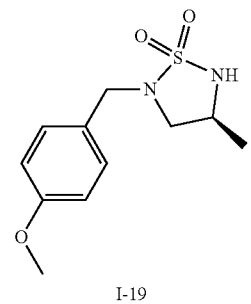

Step 1: Preparation of (2S)—N1-[(4-methoxyphenyl)methyl]propane-1,2-diamine (Compound I-19b)

To a solution of tert-butyl N-[(1S)-1-methyl-2-oxo-ethyl] carbamate (compound I-19a, 3 g, 17.3 mmol) in MeOH (30 mL) was added (4-methoxyphenyl)methanamine (4.8 g, 34.6 mmol) at 20° C. The mixture was stirred at 20° C. for 1 hour, then NaBH(AcO)$_3$ (5.5 g, 26 mmol) was added. The reaction mixture was stirred at 20° C. for 1 hour, then quenched by saturated aqueous NaHCO$_3$ (20 mL) and extracted with EtOAc (20 mL) for 3 times. The combined organic layer was concentrated, and the residue was purified by column chromatography to give a yellow oil, which was dissolved in EtOAc (20 mL), followed by addition of HCl/EtOAc (40 mL). The resulting mixture was stirred at 20° C. for 2 hours, then concentrated to give (2S)—N1-[(4-methoxyphenyl)methyl]propane-1,2-diamine (compound I-19b, 3.65 g, crude) as a yellow solid, which would be used in the next step directly without further purification.

Step 2: Preparation of (4S)-2-[(4-methoxyphenyl) methyl]-4-methyl-1,2,5-thiadiazolidine 1,1-dioxide (Intermediate I-19)

To a solution of sulfamide (1.1 g, 11.5 mmol) in pyridine (20 mL) was added (2S)—N1-[(4-methoxyphenyl)methyl] propane-1,2-diamine (compound I-19b, 2.65 g, 11.5 mmol) at 120° C. The reaction mixture was stirred at 120° C. for 16 hours, then cooled to room temperature and concentrated. The residue was partitioned between H$_2$O (10 mL) and EtOAc (10 mL). The aqueous layer was extracted with EtOAc twice. The combined organic layer was dried over anhydrous Na$_2$SO$_4$ and concentrated. The residue was purified by column chromatography to give (4S)-2-[(4-methoxyphenyl)methyl]-4-methyl-1,2,5-thiadiazolidine 1,1-dioxide (intermediate I-19, 400 mg) as a yellow oil. MS obsd. (ESI$^+$) [(M+H)$^+$]: 279.

Intermediate I-20

(4S)-2-[(4-methoxyphenyl)methyl]-3,4-dimethyl-1,2,5-thiadiazolidine 1,1-dioxide

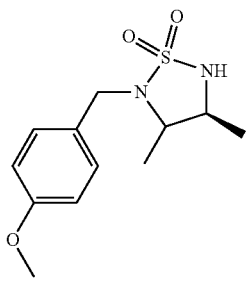 [SMILES: COc1ccc(CN2C(C)[C@H](C)NS2(=O)=O)cc1]

Intermediate I-20 was prepared according to the following scheme:

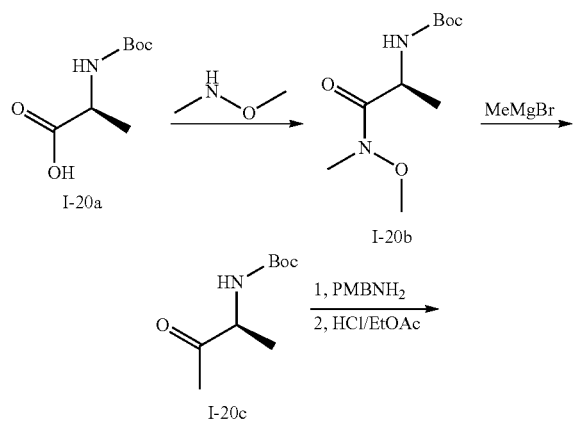

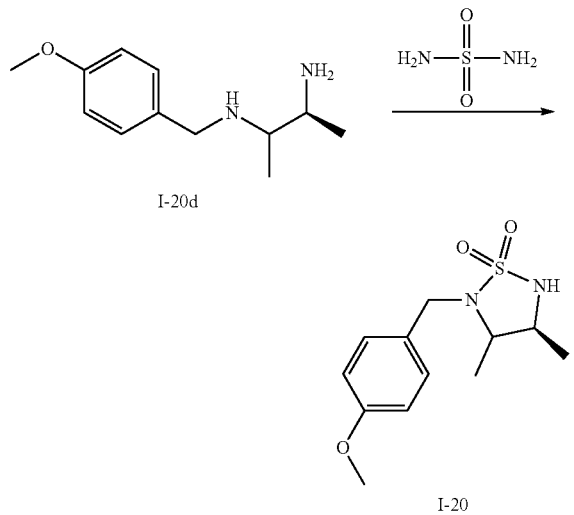

Step 1: Preparation of tert-butyl N-[(1S)-2-[methoxy(methyl)amino]-1-methyl-2-oxo-ethyl]carbamate (Compound I-20b)

To a solution of (2S)-2-(tert-butoxycarbonylamino)propanoic acid (compound I-20a, 10 g, 52.85 mmol) in THF (200 mL) was added HATU (30.1 g, 79 mmol), TEA (13.4 g, 132 mmol) and N-methoxymethanamine hydrochloride (7.7 g, 79 mmol) at 0° C. The reaction mixture was stirred under nitrogen atmosphere at 20° C. for 15 hours, then extracted with EtOAc (200 mL) for 3 times. The combined organic layer was washed with brine, dried over anhydrous Na$_2$SO$_4$, filtered and concentrated. The residue was purified by column chromatography to give compound I-20b (11.5 g) as a white solid. MS obsd. (ESI$^+$) [(M+H)$^+$]: 233.

Step 2: Preparation of tert-butyl N-[(1S)-1-methyl-2-oxo-propyl]carbamate (Compound I-20c)

To a solution of tert-butyl N-[(1S)-2-[methoxy(methyl)amino]-1-methyl-2-oxo-ethyl]carbamate (compound I-20b, 11.5 g, 49.5 mmol) in THF (200 mL) was added MeMgBr (35 mL, 104 mmol) at 0° C. The reaction mixture was stirred at 20° C. for 18 hours, then quenched by adding NH$_4$Cl aqueous solution (100 mL) and extracted by EtOAc (100 mL) for 3 times. The combined organic layer was washed by brine, dried over anhydrous Na$_2$SO$_4$, filtered and concentrated. The residue was purified by column chromatography to give compound I-20c (6.8 g) as a yellow oil. MS obsd. (ESI$^+$) [(M+H)$^+$]: 188.

Step 3-4: Preparation of (4S)-2-[(4-methoxyphenyl)methyl]-3,4-dimethyl-1,2,5-thiadiazolidine 1,1-dioxide (Intermediate I-20)

Intermediate I-20 was prepared in analogy to compound I-19 by tert-butyl N-[(1S)-1-methyl-2-oxo-propyl]carbamate (compound I-20c) instead of tert-butyl N-[(1S)-1-methyl-2-oxo-ethyl]carbamate (compound I-19a). Intermediate I-20 (3.8 g) was obtained as a colorless oil. MS obsd. (ESI$^+$) [(M+H)$^+$]: 271.

Intermediate I-21

1,3,4-Oxathiazinane 3,3-dioxide

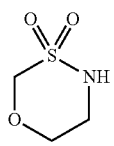

Intermediate I-21 was prepared according to the following scheme:

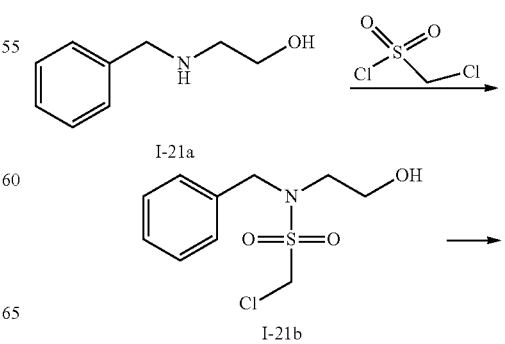

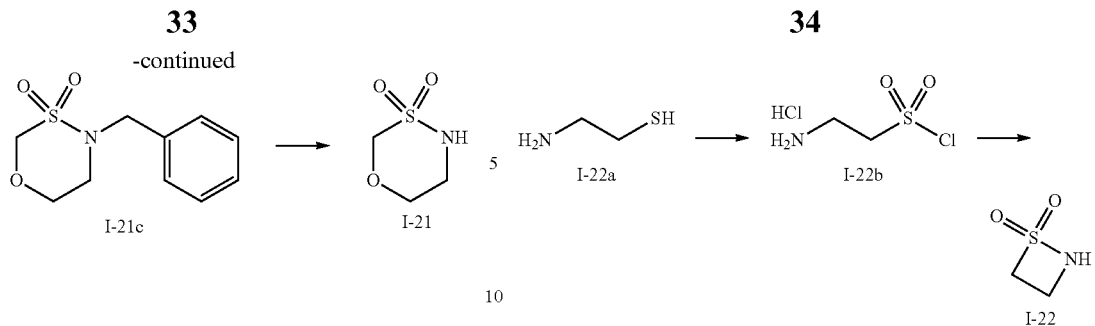

Step 1: Preparation of N-benzyl-1-chloro-N-(2-hydroxyethyl)methanesulfonamide (Compound I-21b)

To a solution of 2-(benzylamino)ethanol (1 g, 6.6 mmol) and DIPEA (1.7 g, 13 mmol) in THF (20 mL) was added chloromethanesulfonyl chloride (1.1 g, 7.3 mmol) dropwise at 0° C. The mixture was stirred at 15° C. for 15 hours, then concentrated under reduced pressure. The residue was partitioned between ethyl acetate (30 mL) and water (20 mL). The organic layer was washed with water and brine, dried over anhydrous $Na_2SO_4$ and concentrated to afford compound I-21b (1.7 g, crude) as a yellow oil. MS obsd. ($ESI^+$) [$(M+H)^+$]: 263.

Step 2: Preparation of 4-benzyl-1,3,4-oxathiazinane 3,3-dioxide (Compound I-21c)

To a solution of N-benzyl-1-chloro-N-(2-hydroxyethyl) methanesulfonamide (compound I-21b, 1.7 g, 6.5 mmol) in DMF (20 mL) was added $Cs_2CO_3$ (4.2 g, 13 mmol). The mixture was stirred at 80° C. for 15 hours, then concentrated under reduced pressure. The residue was partitioned between ethyl acetate (30 mL) and water (20 mL). The organic layer was washed with water and brine, dried over anhydrous $Na_2SO_4$ and concentrated. The residue was purified by column chromatography to afford compound I-21c (1.1 g) as a yellow oil. MS obsd. ($ESI^+$) [$(M+H)^+$]: 228.

Step 3: Preparation of 1,3,4-oxathiazinane 3,3-dioxide (Intermediate I-21)

To a solution of 4-benzyl-1,3,4-oxathiazinane 3,3-dioxide (compound I-21c, 0.45 g, 2.0 mmol) in THF (30.0 mL) and EtOH (30.0 mL) was added Pd/C (0.1 g) and concentrated aqueous HCl solution (1.0 mL). The mixture was stirred under $H_2$ (50 psi) at 45° C. for 24 hours, then filtered. The filtrated was concentrated to afford intermediate I-21 (0.5 g, crude) as yellow solid. MS obsd. ($ESI^+$) [$(M+H)^+$]: 138.

Intermediate I-22

Thiazetidine 1,1-dioxide

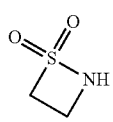

Intermediate I-22 was prepared according to the following scheme:

Step 1: Preparation of 2-aminoethanesulfonyl chloride hydrochloride (Compound I-22b)

Chlorine was blown into a mixture of 2-aminoethanethiol (compound I-22a, 2.5 g, 32.5 mmol) in methanol (25 mL) and water (1.75 g, 97.4 mmol) at 0° C. for 30 minutes. The resulting mixture was stirred for 2 hours at 15° C., then purged with nitrogen, followed by addition of tert-butyl methyl ether (80 mL). The precipitated solid was collected, washed with diethyl ether, dried under reduced pressure to give compound I-22b (0.8 g). MS obsd. ($ESI^+$) [$(M+H)^+$]: 144.

Step 1: Preparation of thiazetidine 1,1-dioxide (Intermediate I-22)

To a solution of 2-aminoethanesulfonyl chloride hydrochloride (compound I-22b, 0.8 g, 4.5 mmol) in DCM (25 mL) was added TEA (1.36 g, 13.5 mmol). The mixture was stirred at 15° C. for 5 hours, then concentrated. The residue was triturated in EtOAc (30.0 mL), then filtered. The filtrated was concentrated to afford intermediate I-22 (0.3 g) as a white solid. $^1$H NMR (400 MHz, DMSO-$d_6$) δ 4.29 (t, 2H), 3.19-3.11 (m, 2H)

Intermediate I-23

1,1-Dioxo-1,2,6-thiadiazinan-4-ol

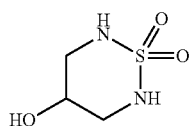

Intermediate I-23 was prepared according to the following scheme:

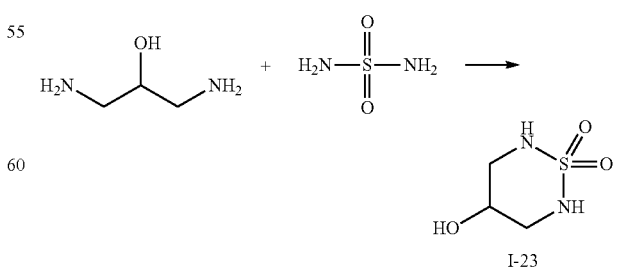

To a solution of sulfamide (1 g, 10.4 mmol) in pyridine (5 mL) was added 1,3-diaminopropan-2-ol (0.94 g, 10.4 mmol)

at 120° C. The reaction mixture was stirred at 120° C. for 16 hours. After being cooled to room temperature, the mixture concentrated and the residue was dissolved in H₂O (3 mL). The resulting mixture was extracted by EtOAc (5 mL) for 10 times. The combined organic layer was dried over Na₂SO₄ and concentrated to give intermediate I-23 (0.3 g, crude) as a yellow solid. ¹H NMR (400 MHz, DMSO-d₆) δ 6.65-6.54 (m, 1H), 5.05 (d, 1H), 3.45 (d, 1H), 3.31-3.22 (m, 2H), 3.15-3.04 (m, 2H).

Intermediate I-24

1,2,6-Thiadiazinane 1,1-dioxide

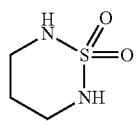

Intermediate I-24 was prepared according to the following scheme:

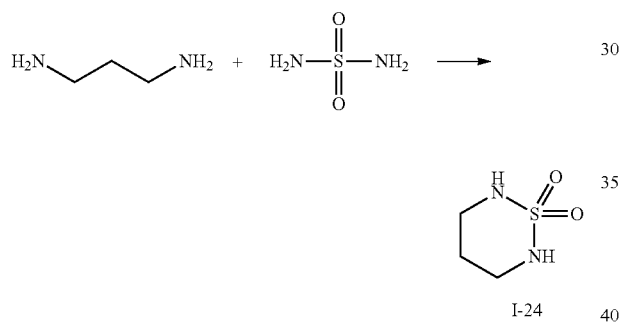

To a mixture of sulfamide (0.96 g, 10 mmol) in pyridine (30 mL) was added propane-1,3-diamine (0.74 g, 10 mmol) at 110° C. The reaction mixture was stirred at 110° C. for 16 hours, then concentrated. The residue was purified by column chromatography to give intermediate I-24 (0.5 g) as a yellow solid. ¹H NMR (400 MHz, DMSO-d₆) δ 6.35 (br t, 2H), 3.31-3.20 (m, 4H), 1.49-1.33 (m, 2H).

Intermediate I-25 tert-Butyl 3-iodo-6-methyl-6,7-dihydro-4H-triazolo[1,5-a]pyrazine-5-carboxylate

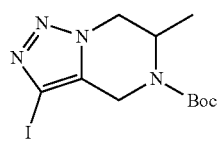 [SMILES: CC1Cn2nnc(I)c2CN1C(=O)OC(C)(C)C]

Intermediate I-25 was prepared according to the following scheme:

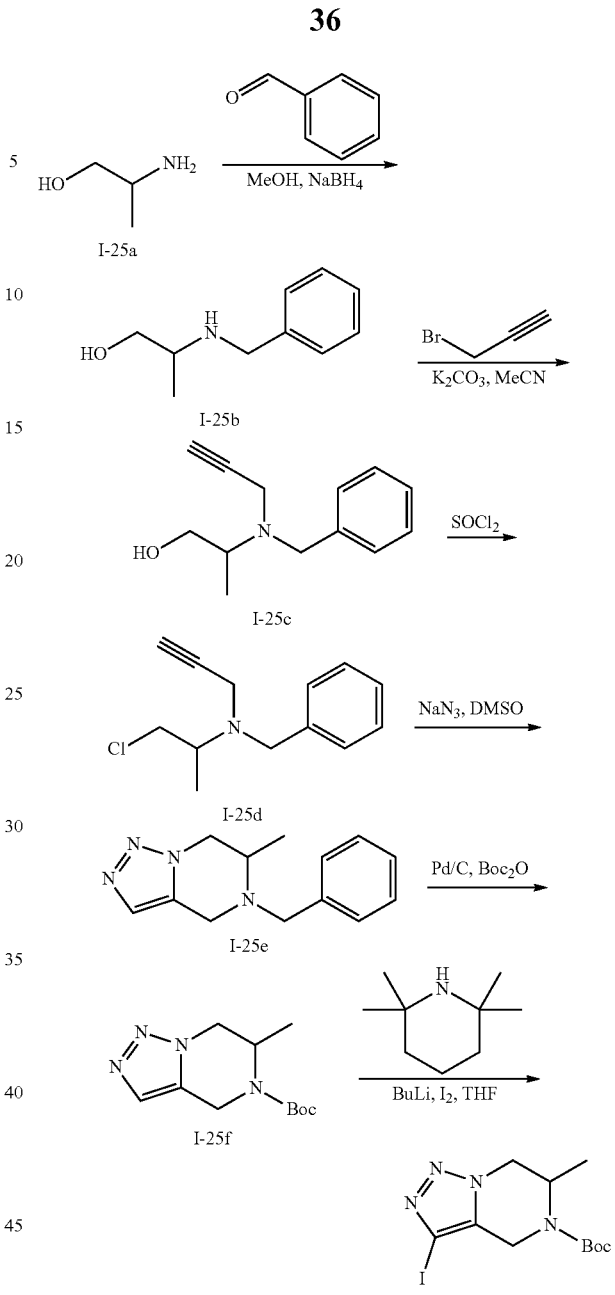

Step 1: Preparation of 2-(benzylamino)propan-1-ol (Compound I-25b)

To a suspension of 2-aminopropan-1-ol (compound I-25a, 20 g, 266 mmol) in toluene (200 mL) was added benzaldehyde (28 g, 266 mmol). The mixture was stirred at 110° C. for 2 hours, then cooled down to 20° C. and concentrated. The residue was dissolved in MeOH (200 mL), followed by addition of NaBH₄ (10 g, 266 mmol) at 0° C. The reaction mixture was allowed to warmed to 20° C. and stirred for 16 hours, then concentrated. The residue was diluted with ice-water (100 mL) and stirred for 30 mins. The resulting mixture was extracted with ethyl acetate (200 mL) for 5 times. The combined organic layer was washed with brine, dried with anhydrous Na₂SO₄, filtered and concentrated.

The residue was purified by column chromatography to afford compound I-25b (18 g) as a yellow solid. LCMS (M+H+): 166.

Step 2: Preparation of 2-[benzyl(prop-2-ynyl)amino]propan-1-ol (Compound I-25c)

To a solution of 2-(benzylamino)propan-1-ol (compound I-25b, 18 g, 109 mmol) and 3-bromoprop-1-yne (15.6 g, 130 mmol) in MeCN (20 mL) was added $K_2CO_3$ (22.6 g, 163 mmol) at 20° C. The mixture was stirred at 80° C. for 16 hours, then cooled down to 20° C. and filtered. The filtrate was concentrated and the residue was purified by column chromatography to afford compound I-25c (19 g) as yellow oil. LCMS (M+H+): 204.

Step 3: Preparation of N-benzyl-1-chloro-N-prop-2-ynyl-propan-2-amine (Compound I-25d)

To a solution of pyridine (11.7 g, 148 mmol) and $SOCl_2$ (21 g, 177 mmol) in DCM (200 mL) was added 2-[benzyl (prop-2-ynyl)amino]propan-1-ol (compound I-25c, 20 g, 98 mmol) at 0° C. This reaction mixture was stirred at 20° C. for 3 hours, then washed with saturated aqueous $NaHCO_3$ (300 mL). The organic layer was washed with water (100 mL) for 3 times, dried over anhydrous $Na_2SO_4$, and concentrated. The residue was purified by column chromatography to afford compound I-25d (17.3 g) as a yellow oil. LCMS (M+H+): 222.

Step 4: Preparation of 5-benzyl-6-methyl-6,7-dihydro-4H-triazolo[1,5-a]pyrazine (Compound I-25e)

To a solution of N-benzyl-1-chloro-N-prop-2-ynyl-propan-2-amine (compound I-25d, 18 g, 81 mmol) in DMSO (200 mL) was added $NaN_3$ (5.28 g, 81 mmol) slowly at 25° C. The reaction mixture was stirred at 150° C. for 3 hours. After cooled down to r.t., the reaction mixture was partitioned between EtOAc (800 mL) and saturated aqueous $Na_2CO_3$ (200 mL). The organic layer was washed with water (100 mL) for 3 times, dried over anhydrous $Na_2SO_4$ and concentrated. The residue was purified by column chromatography to afford compound I-25e (15 g) as a red oil. LCMS (M+H+): 229.

Step 5: Preparation of tert-butyl 6-methyl-6,7-dihydro-4H-triazolo[1,5-a]pyrazine-5-carboxylate (Compound I-25f)

To a solution of 5-benzyl-6-methyl-6,7-dihydro-4H-triazolo[1,5-a]pyrazine (compound I-25e, 15 g, 66 mmol) in MeOH (200 mL) was added $Boc_2O$ (17 g, 79 mmol) and Pd/C (1.20 g). The reaction mixture was stirred at 50° C. for 24 hours under $H_2$ (50 psi). Then filtered. The filtrate was concentrated under reduced pressure. The residue was purified by column chromatography to give a light yellow oil, which was further purified and separated by SFC (Column: Chiralpak AD-3 100×4.6 mm I.D., 3 um, Mobile phase: methanol (0.05% DEA) in $CO_2$ from 5% to 40%) to give compound I-25f-1 (1 g) as a yellow solid and compound I-25f-2 (2 g) as a yellow oil.

Compound I-25f-1: $^1$H NMR (400 MHz, DMSO-$d_6$) δ 7.66 (s, 1H), 4.92 (d, 1H), 4.74 (br. s., 1H), 4.50-4.43 (m, 1H), 4.41-4.29 (m, 2H), 1.45 (s, 9H), 1.02 (d, 3H). LCMS (M+H+): 239.

Compound I-25f-2: $^1$H NMR (400 MHz, DMSO-$d_6$) δ 7.66 (s, 1H), 4.92 (d, 1H), 4.74 (br. s., 1H), 4.50-4.43 (m, 1H), 4.41-4.29 (m, 2H), 1.51-1.40 (m, 9H), 1.02 (d, 3H). LCMS (M+H+): 239.

Step 6: Preparation of tert-butyl 3-iodo-6-methyl-6,7-dihydro-4H-triazolo[1,5-a]pyrazine-5-carboxylate (Intermediate I-25)

To a mixture of 2,2,6,6-tetramethylpiperidine (249 mg, 1.26 mmol) in THF (3 mL) was added BuLi (0.6 mL, 1.5 mmol) at 0° C. The mixture was then cooled to −70° C., followed by addition of a solution of compound I-25f-2 (300 mg, 1.26 mmol) in THF (3 mL). The mixture was stirred at −70° C. for 1 hour, then $I_2$ (1.6 g, 6.3 mmol) in THF (6 mL) was added. The reaction mixture was allowed to warm to 15° C. and stirred for 1 hour. The mixture was quenched with aqueous $NH_4Cl$ (2 mL) and aqueous $Na_2SO_3$ (4 mL), then extracted with EtOAc (50 mL). The organic layer was washed with brine (30 mL), dried over anhydrous $Na_2SO_4$ and concentrated under reduced pressure. The residue was purified by column (PE:EA=5:1) and prep-TLC (PE:EA=1:1) to give intermediate I-25-2 (60 mg) as a white viscous solid. LCMS (M+H+): 365.

Intermediate I-25-1 was prepared in analogy to compound I-25-2 by using compound I-25f-1 instead of compound I-25f-2. Intermediate I-25-1 (60 mg) was obtained as a white viscous solid. LCMS (M+H+): 365.

Intermediate I-26

Phenyl N-(3-thienylmethyl)carbamate

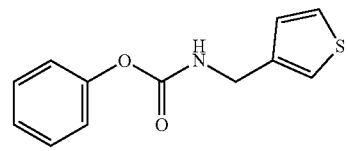 [SMILES: O=C(NCc1ccsc1)Oc1ccccc1]

Intermediate I-26 was prepared in analogy to compound I-5 by using 3-thienylmethanamine instead of 4-chloro-3-fluoroaniline. Intermediate I-26 (60 mg) was obtained as a yellow oil. MS obsd. (ESI+) [(M+H)+]: 234.

Example 1

(6S)-3-(1,1-dioxo-1,2-thiazolidin-2-yl)-6-methyl-N-(3,4,5-trifluorophenyl)-6,7-dihydro-4H-pyrazolo[1,5-a]pyrazine-5-carboxamide

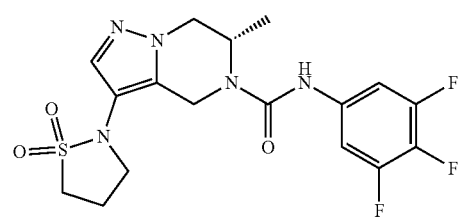 [SMILES: C[C@H]1Cn2ncc(N3CCCS3(=O)=O)c2CN1C(=O)Nc1cc(F)c(F)c(F)c1]

The title compound was prepared according to the following scheme:

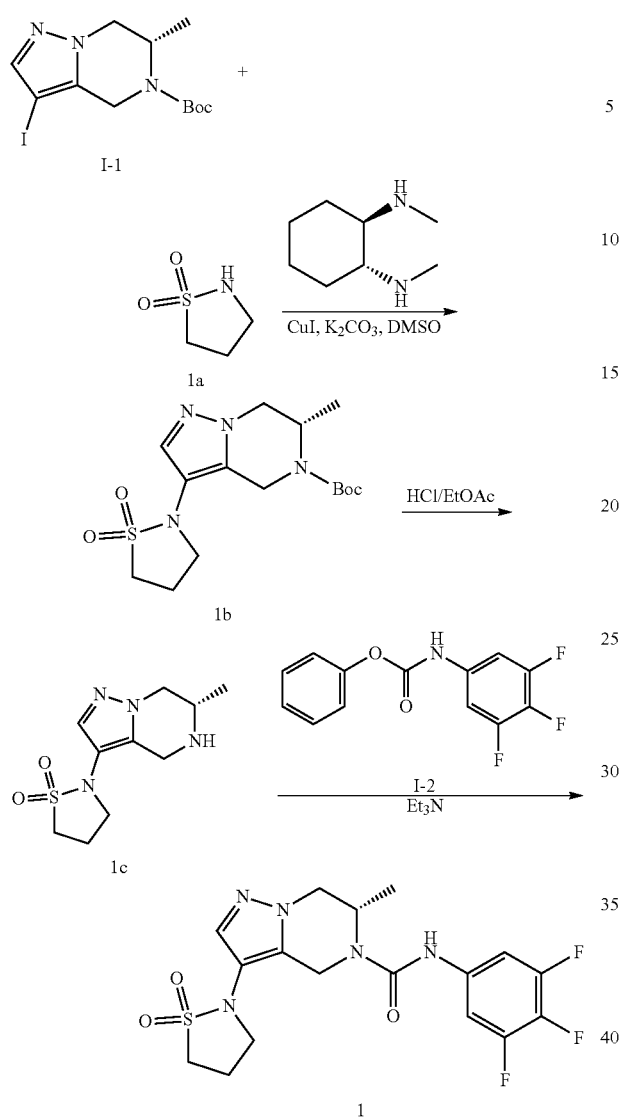

carboxylate (compound 1b, 72 mg, 0.20 mmol) in HCl/EtOAc (4 N, 10 mL) was stirred at 20° C. for 2 hours. Then the reaction mixture was concentrated under reduced pressure to give 2-[(6S)-6-methyl-4,5,6,7-tetrahydropyrazolo[1,5-a]pyrazin-3-yl]-1,2-thiazolidine 1,1-dioxide (compound 1c, 55 mg, crude) as a brown oil. MS obsd. (ESI$^+$) [(M+H)$^+$]: 257.

Step 3: Preparation of (6S)-3-(1,1-dioxo-1,2-thiazolidin-2-yl)-6-methyl-N-(3,4,5-trifluorophenyl)-6,7-dihydro-4H-pyrazolo[1,5-a]pyrazine-5-carboxamide To a mixture of 2-[(6S)-6-methyl-4,5,6,7-tetrahydropyrazolo[1,5-a]pyrazin-3-yl]-1,2-thiazolidine 1,1-dioxide (compound 1c, 55 mg, crude) and phenyl N-(3,4,5-trifluorophenyl)carbamate (intermediate I-2, 57 mg, 0.21 mmol) in DMF (5 mL) was added Et$_3$N (65 mg, 0.64 mmol). The reaction mixture was stirred at 20° C. for 4 hours, and then concentrated under reduced pressure. The residue was purified by prep-HPLC to give (6S)-3-(1,1-dioxo-1,2-thiazolidin-2-yl)-6-methyl-N-(3,4,5-trifluorophenyl)-6,7-dihydro-4H-pyrazolo[1,5-a]pyrazine-5-carboxamide (Example 1, 45 mg) as a white solid. $^1$H NMR (400 MHz, CHLOROFORM-d) δ 7.59 (s, 1H), 7.13-7.25 (m, 2H), 7.01-7.13 (m, 1H), 5.10 (m, 1H), 5.00 (d, 1H), 4.52 (d, 1H), 4.27 (dd, 1H), 4.09 (d, 1H), 3.60-3.79 (m, 2H), 3.31-3.46 (m, 2H), 2.46-2.66 (m, 2H), 1.33 (d, 3H). MS obsd. (ESI$^+$) [(M+H)$^+$]: 430.

Example 2

(6S)—N-(2-chloro-4-pyridyl)-3-(1,1-dioxo-1,2-thiazolidin-2-yl)-6-methyl-6,7-dihydro-4H-pyrazolo[1,5-a]pyrazine-5-carboxamide

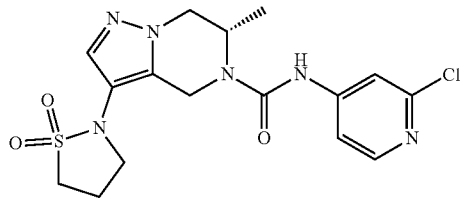 [SMILES: C[C@H]1Cn2ncc(N3CCCS3(=O)=O)c2CN1C(=O)Nc1ccnc(Cl)c1]

The title compound was prepared according to the following scheme:

Step 1: Preparation of tert-butyl (6S)-3-(1,1-dioxo-1,2-thiazolidin-2-yl)-6-methyl-6,7-dihydro-4H-pyrazolo[1,5-a]pyrazine-5-carboxylate (Compound 1b)

To a mixture of tert-butyl (6S)-3-iodo-6-methyl-6,7-dihydro-4H-pyrazolo[1,5-a]pyrazine-5-carboxylate (intermediate I-1, 100 mg, 0.28 mmol), 1,2-thiazolidine 1,1-dioxide (compound 1a, 50 mg, 0.41 mmol), trans-N,N'-dimethylcyclohexane-1,2-diamine (8 mg, 0.055 mmol) and CuI (10 mg, 0.055 mmol) in DMSO (5 mL) was added K$_2$CO$_3$ (114 mg, 0.83 mmol). The reaction mixture was stirred at 100° C. for 12 hours, and then concentrated under reduced pressure. The residue was purified by prep-HPLC to give tert-butyl (6S)-3-(1,1-dioxo-1,2-thiazolidin-2-yl)-6-methyl-6,7-dihydro-4H-pyrazolo[1,5-a]pyrazine-5-carboxylate (compound 1b, 72 mg) as a yellow solid. MS obsd. (ESI$^+$) [(M+H)$^+$]: 357.

Step 2: Preparation of 2-[(6S)-6-methyl-4,5,6,7-tetrahydropyrazolo[1,5-a]pyrazin-3-yl]-1,2-thiazolidine 1,1-dioxide (Compound 1c)

A mixture of tert-butyl (6S)-3-(1,1-dioxo-1,2-thiazolidin-2-yl)-6-methyl-6,7-dihydro-4H-pyrazolo[1,5-a]pyrazine-5-

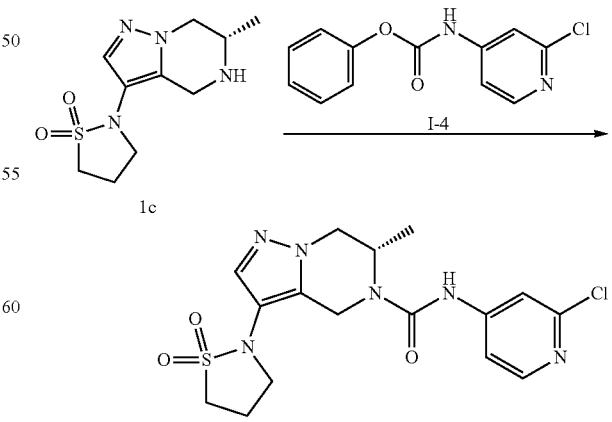

To a solution of 2-[(6S)-6-methyl-4,5,6,7-tetrahydropyrazolo[1,5-a]pyrazin-3-yl]-1,2-thiazolidine 1,1-dioxide (compound 1c, 20 mg, 0.078 mmol) in DMF (1.0 mL) was added TEA (24.0 mg, 0.234 mmol) and phenyl N-(2-chloro-4-pyridyl)carbamate (intermediate I-4, 29.0 mg, 0.117 mmol). The mixture was stirred at 15° C. for 18 hours, and then partitioned between water (5.0 mL) and EtOAc (10.0 mL). The aqueous layer was extracted with EtOAc twice. The combined organic layer was washed with brine, dried over anhydrous Na₂SO₄ and concentrated under reduced pressure. The residue was purified by prep-HPLC to give (6S)—N-(2-chloro-4-pyridyl)-3-(1,1-dioxo-1,2-thiazolidin-2-yl)-6-methyl-6,7-dihydro-4H-pyrazol[1,5-a]pyrazine-5-carboxamide (Example 2, 21 mg) as a white solid. ¹H NMR (400 MHz, CDCl₃) δ 8.17 (d, 1H), 7.56 (s, 1H), 7.55-7.47 (m, 2H), 7.29 (dd, 1H), 5.03-5.01 (m, 2H), 4.52-4.48 (m, 1H), 4.31-4.18 (m, 1H), 4.07 (d, 1H), 3.76-3.58 (m, 2H), 3.36 (t, 2H), 2.61-2.46 (m, 2H), 1.30 (d, 3H). MS obsd. (ESI⁺) [(M+H)⁺]: 411.

Example 3

(6S)—N-(4-chloro-3-fluoro-phenyl)-3-(1,1-dioxo-1,2-thiazolidin-2-yl)-6-methyl-6,7-dihydro-4H-pyrazolo[1,5-a]pyrazine-5-carboxamide

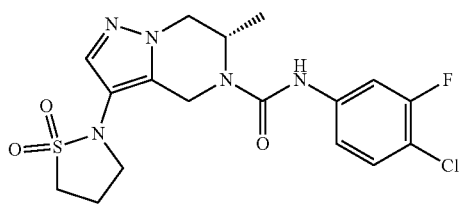 [SMILES: C[C@H]1Cn2ncc(N3CCCS3(=O)=O)c2CN1C(=O)Nc1ccc(Cl)c(F)c1]

The title compound was prepared in analogy to the preparation of Example 2 by using phenyl N-(4-chloro-3-fluoro-phenyl)carbamate (intermediate I-5) instead of phenyl N-(2-chloro-4-pyridyl)carbamate (intermediate I-4). Example 3 (8.0 mg) was obtained as a white solid. ¹H NMR (400 MHz, CDCl₃) δ 7.50 (s, 1H), 7.39 (dd, 1H), 7.15-7.24 (m, 1H), 6.99 (m, 1H), 6.78 (s, 1H), 4.97-5.05 (m, 1H), 4.92 (d, 1H), 4.45 (d, 1H), 4.19 (m, 1H), 4.01 (d, 1H), 3.54-3.67 (m, 2H), 3.26-3.33 (m, 2H), 2.42-2.51 (m, 2H), 1.24 (d, 3H). MS obsd. (ESI⁺) [(M+H)⁺]: 428.

Example 4

(6S)-3-(1,1-dioxo-1,2-thiazolidin-2-yl)-N-(4-fluoro-3-methyl-phenyl)-6-methyl-6,7-dihydro-4H-pyrazolo[1,5-a]pyrazine-5-carboxamide

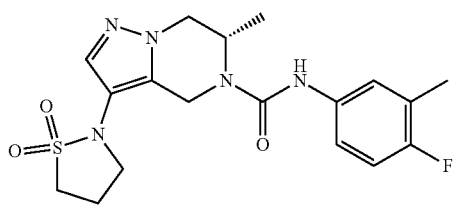 [SMILES: Cc1cc(NC(=O)N2Cc3c(N4CCCS4(=O)=O)cnn3C[C@@H]2C)ccc1F]

The title compound was prepared in analogy to the preparation of Example 2 by using phenyl N-(4-fluoro-3-methyl-phenyl)carbamate (intermediate I-6) instead of phenyl N-(2-chloro-4-pyridyl)carbamate (intermediate I-4). Example 4 (10.7 mg) was obtained as a white solid. ¹H NMR (400 MHz, CDCl₃) δ ppm 7.58 (s, 1H), 7.23-7.27 (m, 1H), 7.08-7.16 (m, 1H), 6.93 (t, 1H), 6.60 (s, 1H), 5.04-5.14 (m, 1H), 4.98 (d, 1H), 4.55 (d, 1H), 4.28 (dd, 1H), 4.10 (d, 1H), 3.62-3.74 (m, 2H), 3.31-3.41 (m, 2H), 2.54 (quin, 2H), 2.26 (s, 3H), 1.28 (d, 3H). MS obsd (ESI) [(M+H)⁺]: 408.

Example 5

(6S)—N-(3-cyano-4-fluoro-phenyl)-3-(1,1-dioxo-1,2-thiazolidin-2-yl)-6-methyl-6,7-dihydro-4H-pyrazolo[1,5-a]pyrazine-5-carboxamide

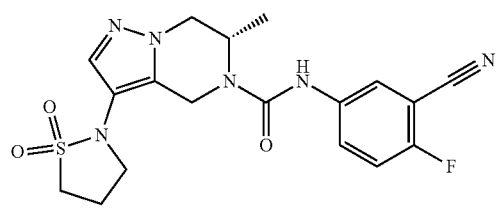 [SMILES: C[C@H]1Cn2ncc(N3CCCS3(=O)=O)c2CN1C(=O)Nc1ccc(F)c(C#N)c1]

The title compound was prepared in analogy to the preparation of Example 2 by using phenyl N-(3-cyano-4-fluoro-phenyl)carbamate (intermediate I-7) instead of phenyl N-(2-chloro-4-pyridyl)carbamate (intermediate I-4). Example 5 (11 mg) was obtained as a white solid. ¹H NMR (400 MHz, CDCl₃) δ 7.73 (m, 1H), 7.64 (m, 1H), 7.57 (s, 1H), 7.21-7.05 (m, 2H), 5.14-4.91 (m, 2H), 4.50 (d, 1H), 4.25 (dd, 1H), 4.06 (d, 1H), 3.81-3.58 (m, 2H), 3.37 (t, 2H), 2.65-2.44 (m, 2H), 1.32 (d, 3H), MS obsd. (ESI⁺) [(M+H)⁺]: 419.

Example 6

(6S)—N-[2-(difluoromethyl)-4-pyridyl]-3-(1,1-dioxo-1,2-thiazolidin-2-yl)-6-methyl-6,7-dihydro-4H-pyrazolo[1,5-a]pyrazine-5-carboxamide

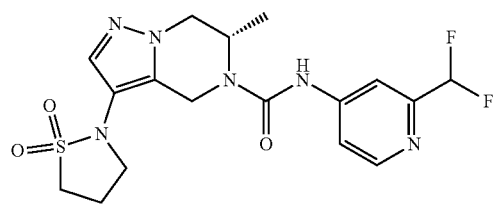 [SMILES: C[C@H]1Cn2ncc(N3CCCS3(=O)=O)c2CN1C(=O)Nc1ccnc(C(F)F)c1]

A mixture of tert-butyl (6S)-3-(1,1-dioxo-1,2-thiazolidin-2-yl)-6-methyl-6,7-dihydro-4H-pyrazolo[1,5-a]pyrazine-5-carboxylate (compound 1b, 100 mg, 0.28 mmol) in DCM (1 mL) and TFA (1 mL) was stirred at room temperature for 30 mins. The reaction mixture was concentrated, and the residue was dissolved in DMF (2.5 mL), followed by addition of N-ethyl-N-isopropylpropan-2-amine (181 mg, 1.4 mmol) and phenyl (2-(difluoromethyl)pyridin-4-yl)carbamate (intermediate I-3, 89 mg, 0.34 mmol). The reaction mixture was stirred at 70° C. for 1 hour, and purified by prep-HPLC to give Example 6 (45 mg) as a white solid. ¹H NMR (400 MHz, METHANOL-d4) δ ppm 8.50 (d, J=6.1 Hz, 1H), 8.02 (d, J=2.2 Hz, 1H), 7.83 (dd, J=2.3, 6.1 Hz, 1H), 7.66 (s, 1H), 6.83 (t, J=54.8 Hz, 1H), 5.18 (d, J=17.0 Hz, 1H), 5.07-4.96 (m, 1H), 4.63 (d, J=17.1 Hz, 1H), 4.34 (dd, J=4.4, 12.8 Hz, 1H), 4.18 (dd, J=1.0, 12.8 Hz, 1H), 3.70 (t, J=6.7 Hz, 2H), 3.45-3.36 (m, 2H), 2.58-2.43 (m, 2H), 1.28 (d, J=6.8 Hz, 3H). MS obsd. (ESI$^+$) [(M+H)$^+$]: 427.

Example 7

(6S)-3-(1,1-dioxo-1,2-thiazolidin-2-yl)-N-[4-fluoro-3-(trifluoromethyl)phenyl]-6-methyl-6,7-dihydro-4H-pyrazolo[1,5-a]pyrazine-5-carboxamide

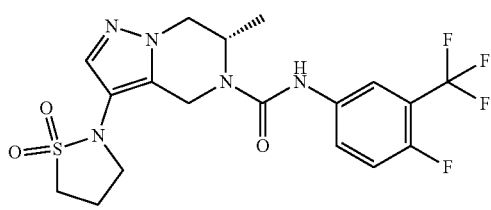 [SMILES: C[C@H]1Cn2ncc(N3CCCS3(=O)=O)c2CN1C(=O)Nc1ccc(F)c(C(F)(F)F)c1]

The title compound was prepared in analogy to the preparation of Example 2 by using phenyl N-[4-fluoro-3-(trifluoromethyl)phenyl]carbamate (intermediate I-8) instead of phenyl N-(2-chloro-4-pyridyl)carbamate (intermediate I-4). Example 7 (17 mg) was obtained as a white solid. $^1$H NMR (400 MHz, CDCl$_3$) δ 7.70 (dd, 1H), 7.54-7.62 (m, 2H), 7.13 (t, 1H), 6.93 (s, 1H), 5.06-5.16 (m, 1H), 5.01 (d, 1H), 4.54 (d, 1H), 4.27 (dd, 1H), 4.10 (d, 1H), 3.61-3.77 (m, 2H), 3.38 (t, 2H), 2.49-2.62 (m, 2H), 1.31 (d, 3H). MS obsd. (ESI$^+$) [(M+H)$^+$]: 462.

Example 8

(6S)-3-(1,1-dioxo-1,2-thiazolidin-2-yl)-N-(2-fluorophenyl)-6-methyl-6,7-dihydro-4H-pyrazolo[1,5-a]pyrazine-5-carboxamide

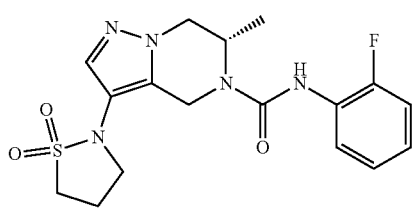 [SMILES: C[C@H]1Cn2ncc(N3CCCS3(=O)=O)c2CN1C(=O)Nc1ccccc1F]

The title compound was prepared in analogy to the preparation of Example 2 by using phenyl N-(2-fluorophenyl)carbamate (intermediate I-9) instead of phenyl N-(2-chloro-4-pyridyl)carbamate (intermediate I-4). Example 8 (18 mg) was obtained as a white solid. $^1$H NMR (400 MHz, CDCl$_3$) δ 8.06-7.98 (m, 1H), 7.59 (s, 1H), 7.16-6.97 (m, 3H), 6.65 (br. s., 1H), 5.10-4.95 (m, 2H), 4.66 (s, 1H), 4.31 (dd, 1H), 4.20-4.10 (m, 1H), 3.66 (dt, 2H), 3.35 (t, 2H), 2.58-2.47 (m, 2H), 1.27 (d, 3H). MS obsd. (ESI$^+$) [(M+H)$^+$]: 394.

Example 9

(6S)—N-(1,3-benzothiazol-6-yl)-3-(1,1-dioxo-1,2-thiazolidin-2-yl)-6-methyl-6,7-dihydro-4H-pyrazolo[1,5-a]pyrazine-5-carboxamide

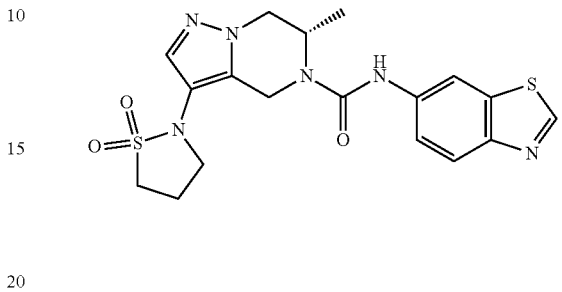

The title compound was prepared in analogy to the preparation of Example 2 by using phenyl N-(1,3-benzothiazol-6-yl)carbamate (intermediate I-10) instead of phenyl N-(2-chloro-4-pyridyl)carbamate (intermediate I-4). Example 9 (4.7 mg) was obtained as a white solid. $^1$H NMR (400 MHz, CDCl$_3$) δ 8.88 (s, 1H), 8.28 (d, 1H), 8.02 (d, 1H), 7.58 (s, 1H), 7.37 (dd, 1H), 6.99 (s, 1H), 5.13 (quin, 1H), 5.05 (d, 1H), 4.66-4.53 (m, 1H), 4.34-4.24 (m, 1H), 4.11 (d, 1H), 3.76-3.61 (m, 2H), 3.37 (t, 2H), 2.62-2.48 (m, 2H), 1.31 (d, 3H). MS obsd. (ESI$^+$) [(M+H)$^+$]: 433.

Example 10

(6S)-3-(1,1-dioxo-1,2-thiazolidin-2-yl)-6-methyl-N-(3-thienyl)-6,7-dihydro-4H-pyrazolo[1,5-a]pyrazine-5-carboxamide

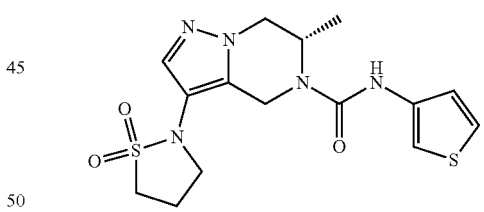

The title compound was prepared in analogy to the preparation of Example 2 by using phenyl N-(3-thienyl)carbamate (intermediate I-11) instead of phenyl N-(2-chloro-4-pyridyl)carbamate (intermediate I-4). Example 10 (3.5 mg) was obtained as a white solid. $^1$H NMR (400 MHz, CDCl$_3$) δ 7.57 (s, 1H), 7.31 (d, 1H), 7.21 (dd, 1H), 7.03 (d, 1H), 7.00-6.94 (m, 1H), 5.15-5.02 (m, 1H), 4.94 (d, 1H), 4.54 (d, 1H), 4.27 (dd, 1H), 4.10 (d, 1H), 3.75-3.60 (m, 2H), 3.41-3.30 (m, 2H), 2.61-2.46 (m, 2H), 1.27 (d, 3H). MS obsd. (ESI$^+$) [(M+H)$^+$]: 382.

Example 11

(6S)—N-benzyl-3-(1,1-dioxo-1,2-thiazolidin-2-yl)-6-methyl-6,7-dihydro-4H-pyrazolo[1,5-a]pyrazine-5-carboxamide

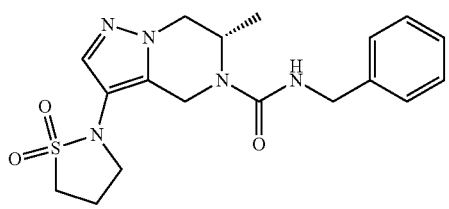 [SMILES: C[C@H]1Cn2ncc(N3CCCS3(=O)=O)c2CN1C(=O)NCc1ccccc1]

The title compound was prepared in analogy to the preparation of Example 2 by using phenyl N-benzylcarbamate (intermediate I-12) instead of phenyl N-(2-chloro-4-pyridyl)carbamate (intermediate I-4). Example 11 (6.4 mg) was obtained as a white solid. $^1$H NMR (400 MHz, CDCl$_3$) δ 7.49 (s, 1H), 7.30-7.20 (m, 5H), 5.09-4.97 (m, 1H), 4.96-4.87 (m, 1H), 4.73 (d, 1H), 4.45-4.31 (m, 3H), 4.15 (dd, 1H), 3.99 (d, 1H), 3.62-3.49 (m, 2H), 3.22 (t, 2H), 2.48-2.31 (m, 2H), 1.11 (d, 3H). MS obsd. (ESI$^+$) [(M+H)$^+$]: 390.

Example 12

(6S)-3-(1,1-dioxo-3a,4,6,7-tetrahydro-3H-[1,2,5]thiadiazolo[3,2-c][1,4]oxazin-2-yl)-6-methyl-N-(3,4,5-trifluorophenyl)-6,7-dihydro-4H-pyrazolo[1,5-a]pyrazine-5-carboxamide

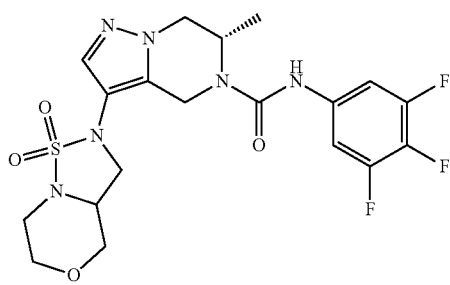 [SMILES: C[C@H]1Cn2ncc(N3CC4COCCN4S3(=O)=O)c2CN1C(=O)Nc1cc(F)c(F)c(F)c1]

The title compound was prepared according to the following scheme:

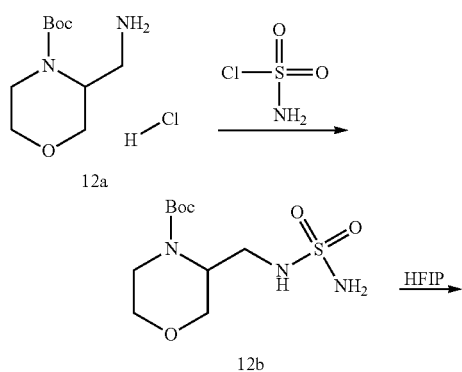

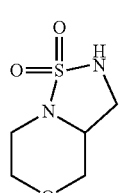
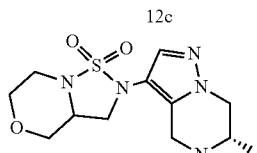

Step 1: Preparation of tert-butyl 3-[(sulfamoylamino)methyl]morpholine-4-carboxylate (Compound 12b)

To a solution of tert-butyl 3-(aminomethyl)morpholine-4-carboxylate hydrochloride (compound 12a, 388 mg, 1.54 mmol) in DCE (5.0 mL) at 0° C. was added TEA (777 mg, 7.68 mmol), DMAP (94 mg, 0.77 mmol) and sulfamoyl chloride (355 mg, 3.07 mmol). The reaction mixture was slowly warmed to room temperature and stirred for 1 hour, then quenched by adding ice-water. The resulting mixture was extracted with DCM. The organic layer was concentrated. The residue was purified by column chromatography (eluting with 8%~10% methanol in dichloromethane) to give compound 12b (227 mg). MS obsd. (ESI$^+$) [(M+H)$^+$]: 296.

Step 2: Preparation of 2,3,3a,4,6,7-hexahydro-[1,2,5]thiadiazolo[3,2-c][1,4]oxazine 1,1-dioxide (Compound 12c)

A solution of tert-butyl 3-[(sulfamoylamino)methyl]morpholine-4-carboxylate (compound 12b, 200 mg, 0.68 mmol) in 1,1,1,3,3,3-hexafluoro-2-propanol (8.0 mL) was heated at 140° C. under microwave in a sealed tube for 2 hours. The reaction mixture was concentrated to give crude compound 12c (121 mg). MS obsd. (ESI$^+$) [(M+H)$^+$]: 179.

Step 3: Preparation of tert-butyl (6S)-3-(1,1-dioxo-3a,4,6,7-tetrahydro-3H-[1,2,5]thiadiazolo[3,2-c][1,4]oxazin-2-yl)-6-methyl-6,7-dihydro-4H-pyrazolo[1,5-a]pyrazine-5-carboxylate (Compound 12d)

A mixture of tert-butyl (6S)-3-iodo-6-methyl-6,7-dihydro-4H-pyrazolo[1,5-a]pyrazine-5-carboxylate (intermediate I-1, 100 mg, 0.28 mmol), K₃PO₄ (117 mg, 0.55 mmol), CuI (10.5 mg, 55 μmol), (1R,2R)—N1,N2-dimethylcyclohexane-1,2-diamine (7.8 mg, 55 μmol) and 2,3,3a,4,6,7-hexahydro-[1,2,5]thiadiazolo[3,2-c][1,4]oxazine 1,1-dioxide (compound 12c, 59 mg, 0.33 mmol) in DMSO (6.0 ml) was heated at 120° C. for 2 hours. The reaction mixture was cooled down, quenched by adding ice-water and extracted with EtOAc twice. The combined organic layer was concentrated, and the residue was purified by column chromatography to compound 12d (45 mg). MS obsd. (ESI⁺) [(M+H)⁺]: 414.

Step 4: Preparation of (6S)-3-(1,1-dioxo-3a,4,6,7-tetrahydro-3H-[1,2,5]thiadiazolo[3,2-c][1,4]oxazin-2-yl)-6-methyl-N-(3,4,5-trifluorophenyl)-6,7-dihydro-4H-pyrazolo[1,5-a]pyrazine-5-carboxamide (Example 12)

A mixture of tert-butyl (6S)-3-(1,1-dioxo-3a,4,6,7-tetrahydro-3H-[1,2,5]thiadiazolo[3,2-c][1,4]oxazin-2-yl)-6-methyl-6,7-dihydro-4H-pyrazolo[1,5-a]pyrazine-5-carboxylate (compound 12d, 45 mg, 109 μmol), 2,2,2-trifluoroacetic acid (2 mL) and DCM (1 mL) was stirred at room temperature for 1 hour. The reaction mixture was concentrated, and the residue was dissolved in DCE (3.0 mL), followed by addition of DIPEA (0.5 mL) and phenyl (3,4,5-trifluorophenyl)carbamate (intermediate I-2, 44 mg, 163 μmol). The reaction mixture was stirred at 45° C. for 2 hours, then washed with ice-water. The aqueous solution was extracted with EtOAc for three times. The combined organic layer was dried over anhydrous Na₂SO₄ and concentrated under reduced pressure. The reside was purified by column chromatography to give Example 12 (22 mg). ¹H NMR (400 MHz, METHANOL-d₄) δ 7.57 (s, 1H), 7.22-7.11 (m, 2H), 4.99 (d, 1H), 4.89-4.80 (m, 1H), 4.46 (d, 1H), 4.20 (dd, 1H), 4.05 (dd, 1H), 3.92 (dd, 1H), 3.81 (td, 1H), 3.69-3.59 (m, 3H), 3.55-3.47 (m, 2H), 3.30-3.25 (m, 1H), 3.04-2.95 (m, 1H), 1.12 (d, 3H). MS obsd. (ESI⁺) [(M+H)⁺]: 487.

Example 13

Benzyl 2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2,5-thiadiazinane-5-carboxylate

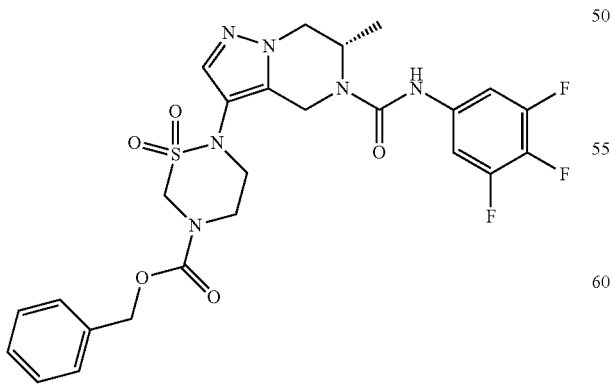

13

The title compound was prepared according to the following scheme:

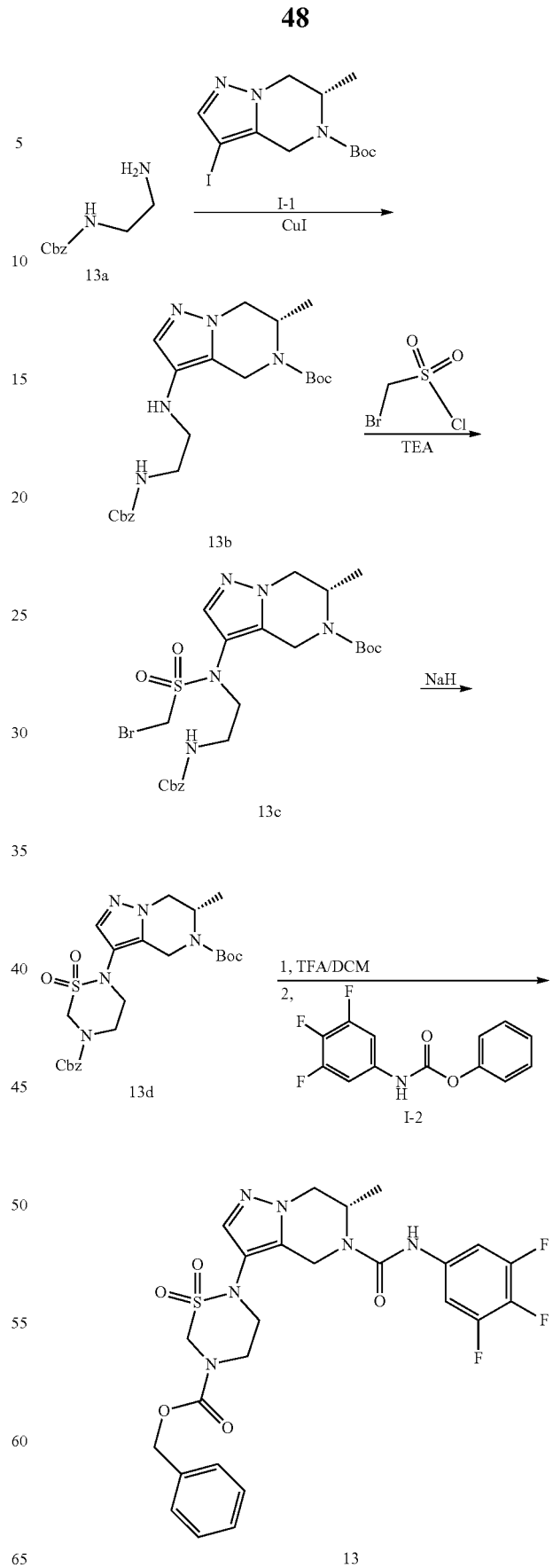

Step 1: Preparation of tert-butyl (6S)-3-[2-(benzyloxycarbonylamino)ethylamino]-6-methyl-6,7-dihydro-4H-pyrazolo[1,5-a]pyrazine-5-carboxylate (Compound 13b)

To a mixture of tert-butyl (6S)-3-iodo-6-methyl-6,7-dihydro-4H-pyrazolo[1,5-a]pyrazine-5-carboxylate (intermediate I-1, 1.09 g, 3.0 mmol), $K_3PO_4$ (1.27 g, 6.0 mmol), CuI (114 mg, 0.6 mmol) and 2-((2,6-dimethylphenyl)amino)-2-oxoacetic acid (232 mg, 1.2 mmol) in DMSO (15.0 mL) was added benzyl (2-aminoethyl)carbamate (compound 13a, 874 mg, 4.5 mmol) under argon. The mixture was heated at 120° C. under microwave for 2 hours. The reaction mixture was diluted with ice-water and then extracted with EtOAc twice. The combined organic layer was separated and concentrated. The residue was purified by column chromatography to give compound 13b (450 mg). MS obsd. (ESI$^+$) [(M+H)$^+$]: 430.

Step 2: Preparation of tert-butyl (6S)-3-[2-(benzyloxycarbonylamino)ethyl-(bromomethylsulfonyl)amino]-6-methyl-6,7-dihydro-4H-pyrazolo[1,5-a]pyrazine-5-carboxylate (Compound 13c)

To a solution of tert-butyl (6S)-3-[2-(benzyloxycarbonylamino)ethylamino]-6-methyl-6,7-dihydro-4H-pyrazolo[1,5-a]pyrazine-5-carboxylate (compound 13b, 450 mg, 1.05 mmol) in THF (10.0 mL) was added TEA (0.44 mL, 3.14 mmol). The reaction mixture was cooled to 0° C., followed by drop-wise addition of bromomethanesulfonyl chloride (507 mg, 2.62 mmol). The reaction mixture was slowly warmed to room temperature and stirred for 2 hours, then quenched by adding ice-water. The resulting mixture was extracted with EtOAc twice, and the combined organic layer were separated and concentrated. The residue was purified by column chromatography to give compound 13c (540 mg). MS obsd. (ESI$^+$) [(M+H)$^+$]: 587.

Step 3: Preparation of benzyl 2-[(6S)-5-tert-butoxycarbonyl-6-methyl-6,7-dihydro-4H-pyrazolo[1,5-a]pyrazin-3-yl]-1,1-dioxo-1,2,5-thiadiazinane-5-carboxylate (Compound 13d)

To a solution of tert-butyl (6S)-3-[2-(benzyloxycarbonylamino)ethyl-(bromomethylsulfonyl)amino]-6-methyl-6,7-dihydro-4H-pyrazolo[1,5-a]pyrazine-5-carboxylate (compound 13c, 540 mg, 0.92 mmol) in DMF (8.0 mL) at 0° C. was added sodium hydride (92 mg, 2.3 mmol). The reaction mixture was stirred at 0° C. for 1 hour then warmed up to room temperature and stirred for 2 hours. The reaction mixture was quenched by adding ice-water, and then extracted with EtOAc twice. The combined organic layer was dried over anhydrous $Na_2SO_4$, filtrated and concentrated. The residue was purified by column chromatography to give compound 13d (300 mg, crude). MS obsd. (ESI$^+$) [(M+H)$^+$]: 506.

Step 4: Preparation of benzyl 2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2,5-thiadiazinane-5-carboxylate (Example 13)

A mixture of benzyl 2-[(6S)-5-tert-butoxycarbonyl-6-methyl-6,7-dihydro-4H-pyrazolo[1,5-a]pyrazin-3-yl]-1,1-dioxo-1,2,5-thiadiazinane-5-carboxylate (compound 13d, 123 mg, 0.24 mmol) in 2,2,2-trifluoroacetic acid (2.0 mL) and DCM (1.0 mL) was stirred at room temperature for 1 hour, and then concentrated. The residue was dissolved in DCE (3.0 mL), followed by addition of DIPEA (0.5 mL) and phenyl (3,4,5-trifluorophenyl)carbamate (intermediate I-2, 78 mg, 0.29 mmol). The reaction mixture was stirred at 45° C. for 2 hours, then diluted with EtOAc. The mixture was washed with water, and the aqueous layer was extracted with EtOAc for three times. The combined organic layer was dried over anhydrous $Na_2SO_4$ and concentrated under reduced pressure. The residue was purified by prep-HPLC to give Example 13 (70 mg). $^1$H NMR (400 MHz, METHANOL-$d_4$) δ 7.63 (br s, 1H), 7.33-7.13 (m, 7H), 5.14 (br s, 2H), 4.97-4.81 (m, 4H), 4.42 (d, J=17.0 Hz, 1H), 4.17 (dd, J=4.3, 12.9 Hz, 1H), 4.06-3.99 (m, 1H), 3.87-3.62 (m, 4H), 1.10 (d, J=6.8 Hz, 3H). MS obsd. (ESI$^+$) [(M+H)$^+$]: 579.

Example 14

(6S)-6-methyl-N-(3,4,5-trifluorophenyl)-3-(3,3,6-trioxo-4,7,8,8a-tetrahydro-1H-pyrrolo[2,1-d][1,2,5]thiadiazin-2-yl)-6,7-dihydro-4H-pyrazolo[1,5-a]pyrazine-5-carboxamide

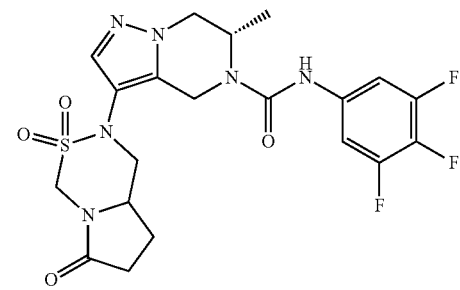 [SMILES: C[C@H]1Cn2ncc(N3CC4CCC(=O)N4CS3(=O)=O)c2CN1C(=O)Nc1cc(F)c(F)c(F)c1]

The title compound was prepared according to the following scheme:

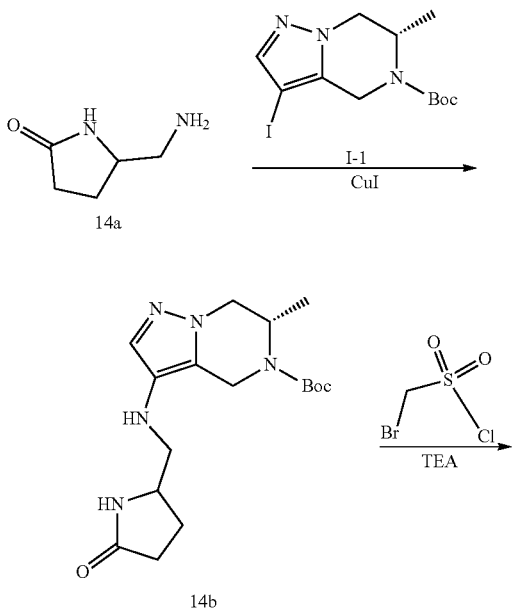

51

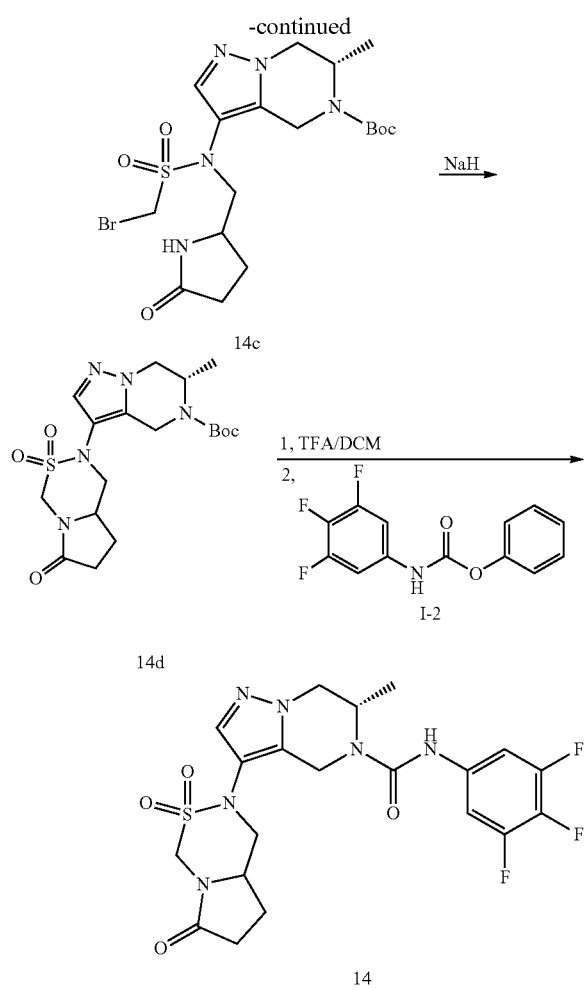

14c

14d

14

The title compound was prepared in analogy to Example 13 by using 5-(aminomethyl)pyrrolidin-2-one (compound 14a) instead of benzyl N-(2-aminoethyl)carbamate (compound 13a). Example 14 (11.1 mg) was obtained as a solid. $^1$H NMR (400 MHz, METHANOL-$d_4$) δ 7.70 (s, 0.5H), 7.65 (s, 0.5H), 7.23-7.13 (m, 2H), 5.19-5.09 (m, 1H), 4.99-4.90 (m, 1H), 4.90-4.82 (m, 1H), 4.48-4.36 (m, 2H), 4.31-4.11 (m, 2H), 4.09-3.89 (m, 2H), 3.59-3.42 (m, 1H), 2.59-2.38 (m, 2H), 2.31-2.18 (m, 1H), 1.75-1.63 (m, 1H), 1.11 (d, J=6.8 Hz, 3H). MS obsd. (ESI$^+$) [(M+H)$^+$]: 499.

Example 15

(6S)-3-(5-acetyl-1,1-dioxo-1,2,5-thiadiazinan-2-yl)-6-methyl-N-(3,4,5-trifluorophenyl)-6,7-dihydro-4H-pyrazolo[1,5-a]pyrazine-5-carboxamide

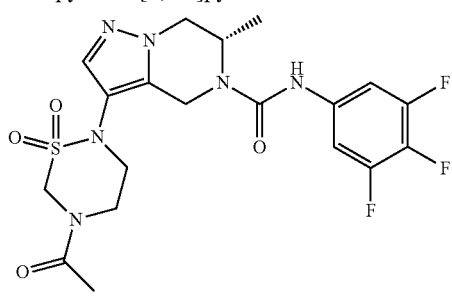

52

The title compound was prepared according to the following scheme:

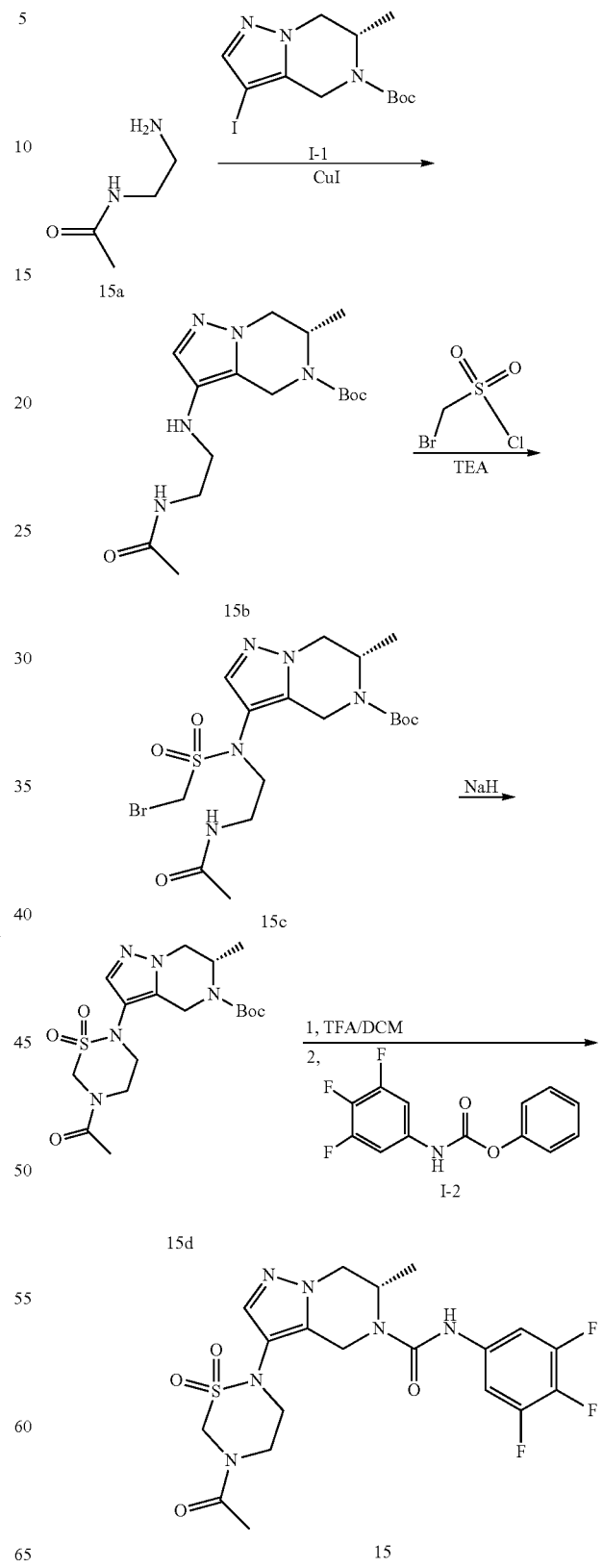

15

The title compound was prepared in analogy to Example 13 by using N-(2-aminoethyl)acetamide (compound 15a) instead of benzyl N-(2-aminoethyl)carbamate (compound 13a). Example 15 (15.0 mg) was obtained as a solid. $^1$H NMR (400 MHz, METHANOL-d$_4$) δ 7.65-7.62 (m, 1H), 7.22-7.13 (m, 2H), 5.02-4.92 (m, 3H), 4.91-4.78 (m, 1H), 4.43 (d, J=17.0 Hz, 1H), 4.18 (dd, J=4.1, 12.7 Hz, 1H), 4.08-4.01 (m, 1H), 3.92-3.80 (m, 2H), 3.74-3.69 (m, 1H), 3.66-3.61 (m, 1H), 2.18-2.12 (m, 3H), 1.11 (d, J=7.0 Hz, 3H). MS obsd. (ESI$^+$) [(M+H)$^+$]: 487.

Example 16

(6S)-6-methyl-3-(3-methyl-1,1-dioxo-1,2-thiazolidin-2-yl)-N-(3,4,5-trifluorophenyl)-6,7-dihydro-4H-pyrazolo[1,5-a]pyrazine-5-carboxamide

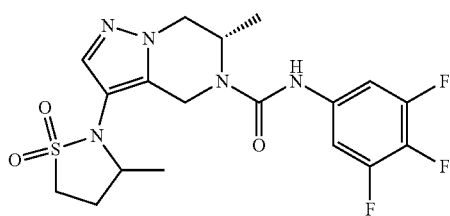 [SMILES: CC1CCS(=O)(=O)N1c1cnn2c1CN(C(=O)Nc1cc(F)c(F)c(F)c1)[C@@H](C)C2]

The title compound was prepared according to the following scheme:

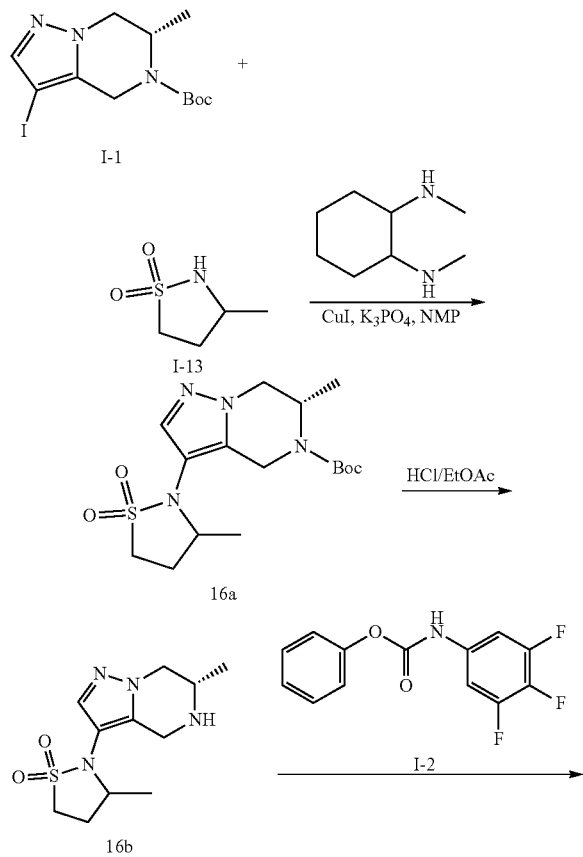

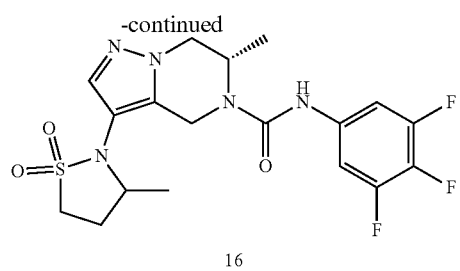

Step 1: Preparation of tert-butyl (6S)-6-methyl-3-(3-methyl-1,1-dioxo-1,2-thiazolidin-2-yl)-6,7-dihydro-4H-pyrazolo[1,5-a]pyrazine-5-carboxylate (Compound 16a)

To a solution of tert-butyl (6S)-3-iodo-6-methyl-6,7-dihydro-4H-pyrazolo[1,5-a]pyrazine-5-carboxylate (intermediate I-1, 100.0 mg, 0.275 mmol) in NMP (5.0 mL) was added CuI (10.0 mg, 0.055 mmol), K$_3$PO$_4$ (175.0 mg, 0.825 mmol), N,N'-dimethyl-1,2-cyclohexanediamine (8.0 mg, 0.055 mmol) and 3-methyl-1,2-thiazolidine 1,1-dioxide (intermediate I-13, 56.0 mg, 0.413 mmol). Then the mixture was heated under microwaves at 140° C. with stirring for 3 hrs. The reaction was conducted at the same scale ten times in parallel. The reaction mixtures were partitioned between H$_2$O (80.0 mL) and EA (80.0 mL). The aqueous was extracted with EA (80.0 mL) twice. The combined organic layer was washed with brine, dried over anhydrous Na$_2$SO$_4$ and concentrated under reduced pressure. The residue was purified by column chromatography and pre-HPLC to give tert-butyl (6S)-6-methyl-3-(3-methyl-1,1-dioxo-1,2-thiazolidin-2-yl)-6,7-dihydro-4H-pyrazolo[1,5-a]pyrazine-5-carboxylate (compound 16a, 100.0 mg) as a yellow oil. MS obsd. (ESI$^+$) [(M+H)$^+$]: 371.

Step 2: Preparation of 3-methyl-2-[(6S)-6-methyl-4,5,6,7-tetrahydropyrazolo[1,5-a]pyrazin-3-yl]-1,2-thiazolidine 1,1-dioxide (Compound 16b)

To a solution of tert-butyl (6S)-6-methyl-3-(3-methyl-1,1-dioxo-1,2-thiazolidin-2-yl)-6,7-dihydro-4H-pyrazolo[1,5-a]pyrazine-5-carboxylate (compound 16a, 50 mg, 0.135 mmol) in EtOAc (2.0 mL) was added a solution of HCl in EtOAc (5.0 mL, 20.0 mmol). The mixture was stirred at 15° C. for 4 hrs, and then concentrated under reduced pressure to give 3-methyl-2-[(6S)-6-methyl-4,5,6,7-tetrahydropyrazolo[1,5-a]pyrazin-3-yl]-1,2-thiazolidine 1,1-dioxide (compound 16b, 60 mg, crude) as a yellow solid. MS obsd. (ESI$^+$) [(M+H)$^+$]: 271.

Step 3: Preparation of (6S)-6-methyl-3-(3-methyl-1,1-dioxo-1,2-thiazolidin-2-yl)-N-(3,4,5-trifluorophenyl)-6,7-dihydro-4H-pyrazolo[1,5-a]pyrazine-5-carboxamide To a mixture of 3-methyl-2-[(6S)-6-methyl-4,5,6,7-tetrahydropyrazolo[1,5-a]pyrazin-3-yl]-1,2-thiazolidine 1,1-dioxide (60.0 mg, 0.222 mmol) in DMF (5 mL) was added Et$_3$N (67.4 mg, 0.666 mmol) and phenyl N-(3,4,5-trifluorophenyl)carbamate (59.3 mg, 0.222 mmol). The mixture was stirred at 15° C. for 15 hrs, and then partitioned between EA (100 mL) and water (30 mL). The organic layer was washed with brine (30 mL), dried over anhydrous Na$_2$SO$_4$ and concentrated under reduced pressure. The residue was purified by prep-HPLC to give (6S)-6-methyl-3-(3-methyl-1,1-dioxo-1,2-thiazolidin-2-yl)-N-(3,4,5-trifluorophenyl)-6,7-dihydro-4H-pyrazolo[1,5-a]pyrazine-5-carboxamide (Example 16, 11.5 mg) as a white solid. ¹H NMR (400 MHz, CDCl₃) δ 7.58-7.51 (m, 1H), 7.21-7.08 (m, 2H), 7.02 (s, 1H), 5.05 (m, 1H), 5.00-4.82 (m, 1H), 4.56-4.35 (m, 1H), 4.31-4.19 (m, 1H), 4.14-4.02 (m, 1H), 3.89-3.69 (m, 1H), 3.50-3.27 (m, 2H), 2.66-2.55 (m, 1H), 2.16 (m, 1H), 1.35-1.26 (m, 3H), 1.26-1.17 (m, 3H), MS obsd. (ESI⁺) [(M+H)⁺]: 444.

Example 17

(6S)-6-methyl-3-(1-oxo-1,2-thiazolidin-2-yl)-N-(3,4,5-trifluorophenyl)-6,7-dihydro-4H-pyrazolo[1,5-a]pyrazine-5-carboxamide

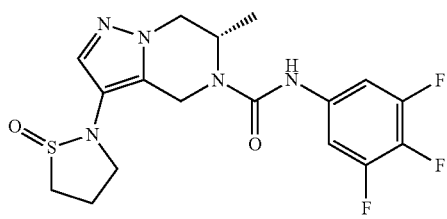 [SMILES: C[C@H]1Cn2ncc(N3CCCS3=O)c2CN1C(=O)Nc1cc(F)c(F)c(F)c1]

The title compound was prepared according to the following scheme:

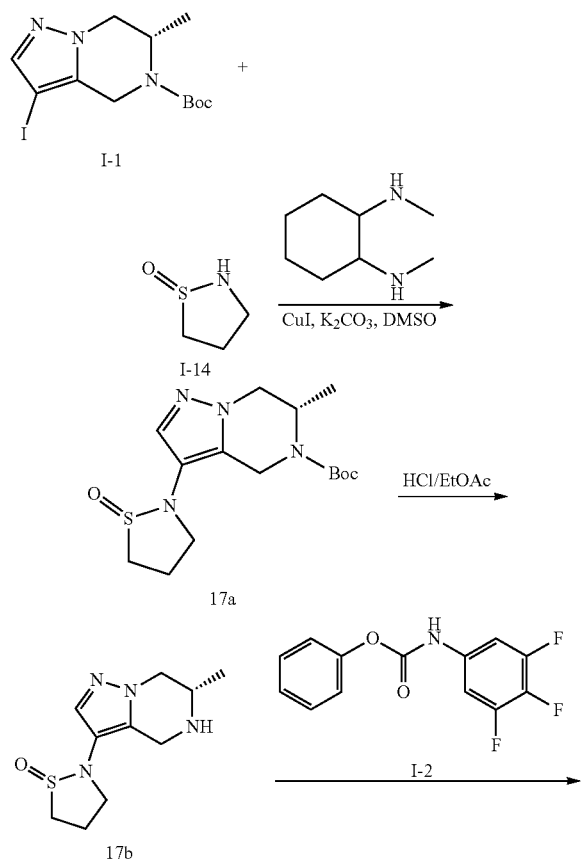

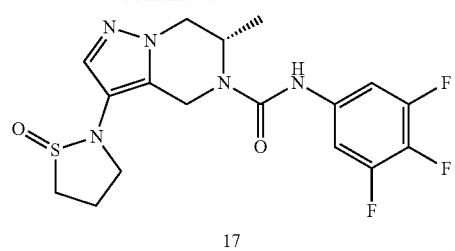

The title compound was prepared in analogy to Example 1 by using 1,2-thiazolidine 1-oxide (intermediate I-14) instead of 1,2-thiazolidine 1,1-dioxide (compound 1a), and N,N'-dimethyl-1,2-cyclohexanediamine instead of trans-N,N'-dimethyl-1,2-cyclohexanediamine. Example 17 (11 mg) was obtained as a white solid. ¹H NMR (400 MHz, DMSO-d₆) δ 7.56-8.05 (m, 1H), 7.41-7.46 (d, 1H), 7.22-7.27 (m, 2H), 4.87-5.23 (m, 2H), 4.66-4.35 (m, 1H), 4.02-4.27 (m, 2H), 3.66-3.72 (m, 2H), 3.17-3.22 (m, 2H), 2.82 (m, 1H), 1.25-1.37 (m, 3H). MS obsd. (ESI⁺) [(M+H)⁺]: 414.

Example 18

(6S)-3-(4-hydroxy-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide

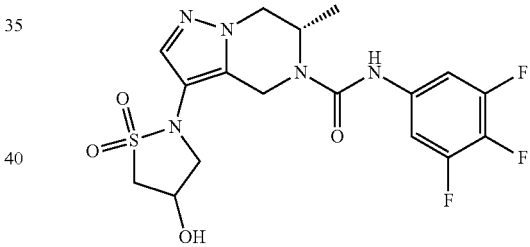

The title compound was prepared according to the following scheme:

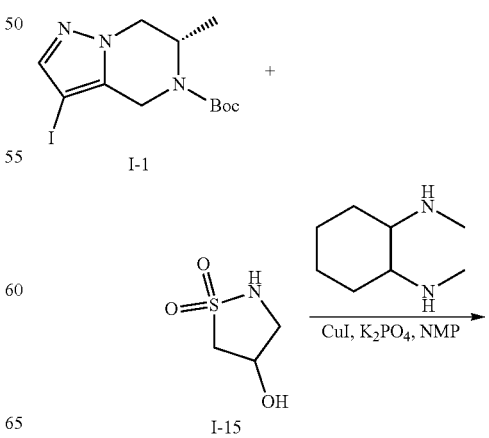

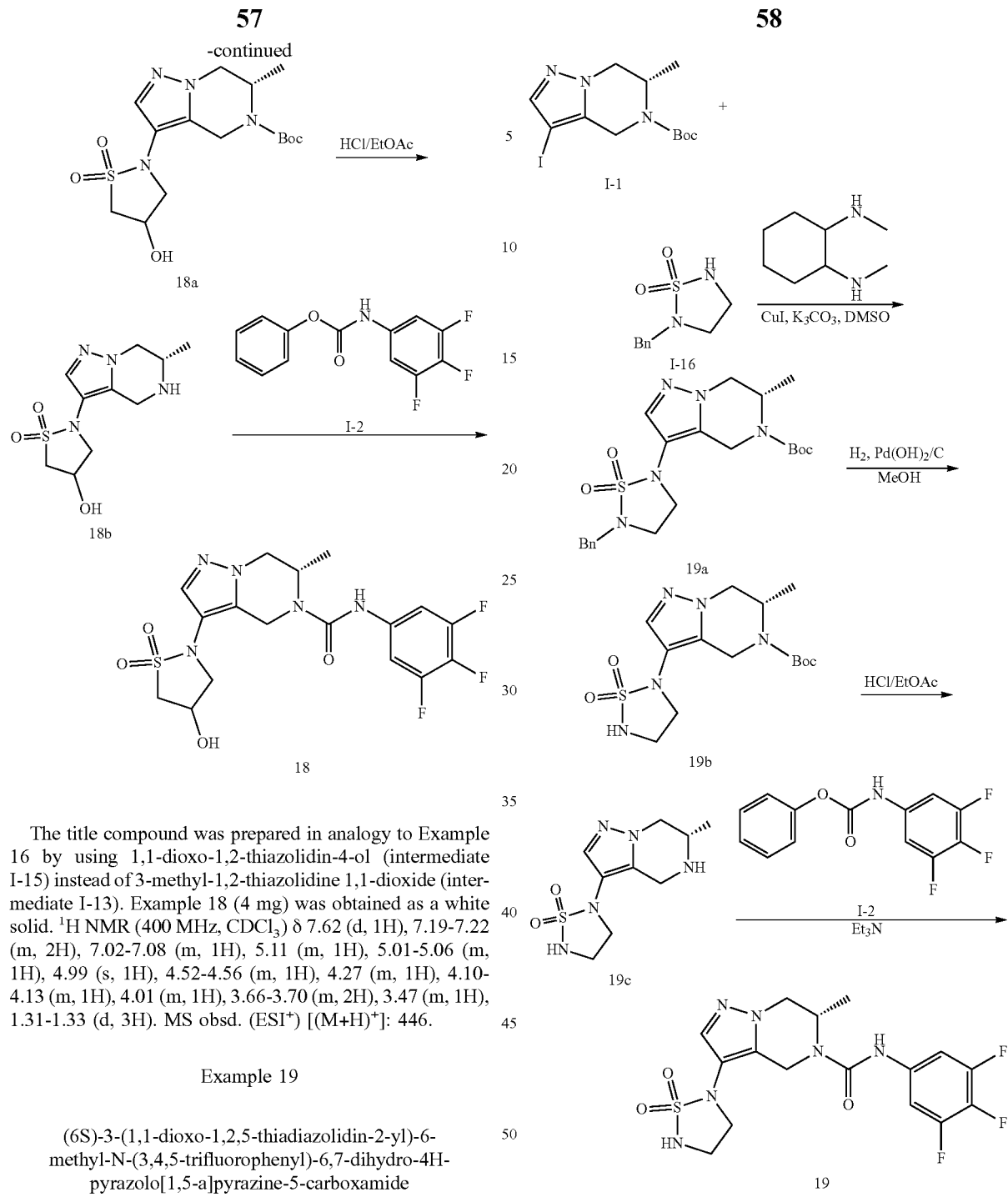

The title compound was prepared in analogy to Example 16 by using 1,1-dioxo-1,2-thiazolidin-4-ol (intermediate I-15) instead of 3-methyl-1,2-thiazolidine 1,1-dioxide (intermediate I-13). Example 18 (4 mg) was obtained as a white solid. $^1$H NMR (400 MHz, CDCl$_3$) δ 7.62 (d, 1H), 7.19-7.22 (m, 2H), 7.02-7.08 (m, 1H), 5.11 (m, 1H), 5.01-5.06 (m, 1H), 4.99 (s, 1H), 4.52-4.56 (m, 1H), 4.27 (m, 1H), 4.10-4.13 (m, 1H), 4.01 (m, 1H), 3.66-3.70 (m, 2H), 3.47 (m, 1H), 1.31-1.33 (d, 3H). MS obsd. (ESI$^+$) [(M+H)$^+$]: 446.

Example 19

(6S)-3-(1,1-dioxo-1,2,5-thiadiazolidin-2-yl)-6-methyl-N-(3,4,5-trifluorophenyl)-6,7-dihydro-4H-pyrazolo[1,5-a]pyrazine-5-carboxamide

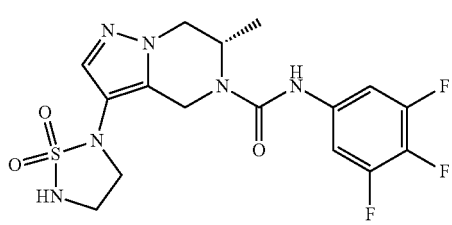 [SMILES: C[C@H]1Cn2ncc(N3CCNS3(=O)=O)c2CN1C(=O)Nc1cc(F)c(F)c(F)c1]

The title compound was prepared according to the following scheme:

Step 1: Preparation of tert-butyl (6S)-3-(5-benzyl-1,1-dioxo-1,2,5-thiadiazolidin-2-yl)-6-methyl-6,7-dihydro-4H-pyrazolo[1,5-a]pyrazine-5-carboxylate (Compound 19a)

To a solution of tert-butyl (6S)-3-iodo-6-methyl-6,7-dihydro-4H-pyrazolo[1,5-a]pyrazine-5-carboxylate (intermediate I-1, 100 mg, 0.275 mmol), 2-benzyl-1,2,5-thiadiazolidine 1,1-dioxide (intermediate I-16, 117 mg, 0.413 mmol), N,N'-dimethyl-1,2-cyclohexanediamine (8 mg, 0.055 mmol) and CuI (10 mg, 0.055 mmol) in DMSO (5 mL) was added K$_2$CO$_3$ (114 mg, 0.825 mmol). The reaction mixture was stirred at 110° C. for 12 hours. After being cooled to room temperature, the mixture was filtered and the filtrate was purified by prep-HPLC to give compound 19a (90 mg) as a yellow solid substance. MS obsd. (ESI+) [(M+H)+]: 448.

Step 2: Preparation of tert-butyl (6S)-3-(1,1-dioxo-1,2,5-thiadiazolidin-2-yl)-6-methyl-6,7-dihydro-4H-pyrazolo[1,5-a]pyrazine-5-carboxylate (Compound 19b)

To a solution of tert-butyl (6S)-3-(5-benzyl-1,1-dioxo-1,2,5-thiadiazolidin-2-yl)-6-methyl-6,7-dihydro-4H-pyrazolo[1,5-a]pyrazine-5-carboxylate (compound 19a, 90 mg, 0.20 mmol) in MeOH (20 mL) was added Pd(OH)$_2$/C (10 mg). The reaction mixture was stirred at 40° C. for 12 hours under H$_2$ (50 psi), and then at 60° C. for 12 hours under H$_2$ (50 psi). The reaction mixture was filtered, and the filtrate was concentrated under reduced pressure to give compound 19b (65 mg, crude) as a yellow oil. MS obsd. (ESI+) [(M+H)+]: 358.

Step 3: Preparation of 2-[(6S)-6-methyl-4,5,6,7-tetrahydropyrazolo[1,5-a]pyrazin-3-yl]-1,2,5-thiadiazolidine 1,1-dioxide (Compound 19c)

A solution of tert-butyl (6S)-3-(1,1-dioxo-1,2,5-thiadiazolidin-2-yl)-6-methyl-6,7-dihydro-4H-pyrazolo[1,5-a]pyrazine-5-carboxylate (compound 19b, 65 mg, 0.18 mmol) in HCl/EA (10 mL, 4 N) was stirred at 20° C. for 2 hours, and then concentrated under reduced pressure to give compound 19c (50 mg, crude) as a brown oil. MS obsd. (ESI+) [(M+H)+]: 258.

Step 4: Preparation of (6S)-3-(1,1-dioxo-1,2,5-thiadiazolidin-2-yl)-6-methyl-N-(3,4,5-trifluorophenyl)-6,7-dihydro-4H-pyrazolo[1,5-a]pyrazine-5-carboxamide (Example 19)

To a mixture of 2-[(6S)-6-methyl-4,5,6,7-tetrahydropyrazolo[1,5-a]pyrazin-3-yl]-1,2,5-thiadiazolidine 1,1-dioxide (compound 19c, 47 mg, 0.183 mmol) and phenyl N-(3,4,5-trifluorophenyl)carbamate (intermediate I-2, 49 mg, 0.183 mmol) in DMF (5 mL) was added Et$_3$N (56 mg, 0.549 mmol). The mixture was stirred at 20° C. for 4 hours, then concentrated under reduced pressure. The residue was purified by prep-HPLC to give Example 19 (33 mg) as a white solid. $^1$H NMR (400 MHz, CHLOROFORM-d) δ 7.62 (s, 1H), 7.15 (dd, 2H), 6.83 (s, 1H), 5.04-5.13 (m, 1H), 4.99 (d, 1H), 4.49-4.63 (m, 2H), 4.28 (dd, 1H), 4.10 (d, 1H), 3.78-3.94 (m, 2H), 3.72 (q, 2H), 1.24-1.39 (m, 3H). MS obsd. (ESI+) [(M+H)+]: 431.

Example 20

(6S)-6-methyl-3-(5-methyl-1,1-dioxo-1,2,5-thiadiazolidin-2-yl)-N-(3,4,5-trifluorophenyl)-6,7-dihydro-4H-pyrazolo[1,5-a]pyrazine-5-carboxamide

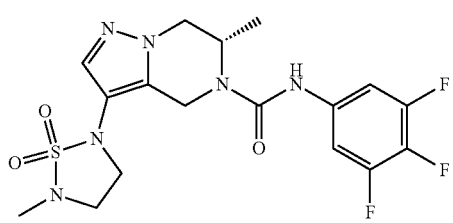 [SMILES: C[C@H]1Cn2ncc(N3CCN(C)S3(=O)=O)c2CN1C(=O)Nc1cc(F)c(F)c(F)c1]

The title compound was prepared according to the following scheme:

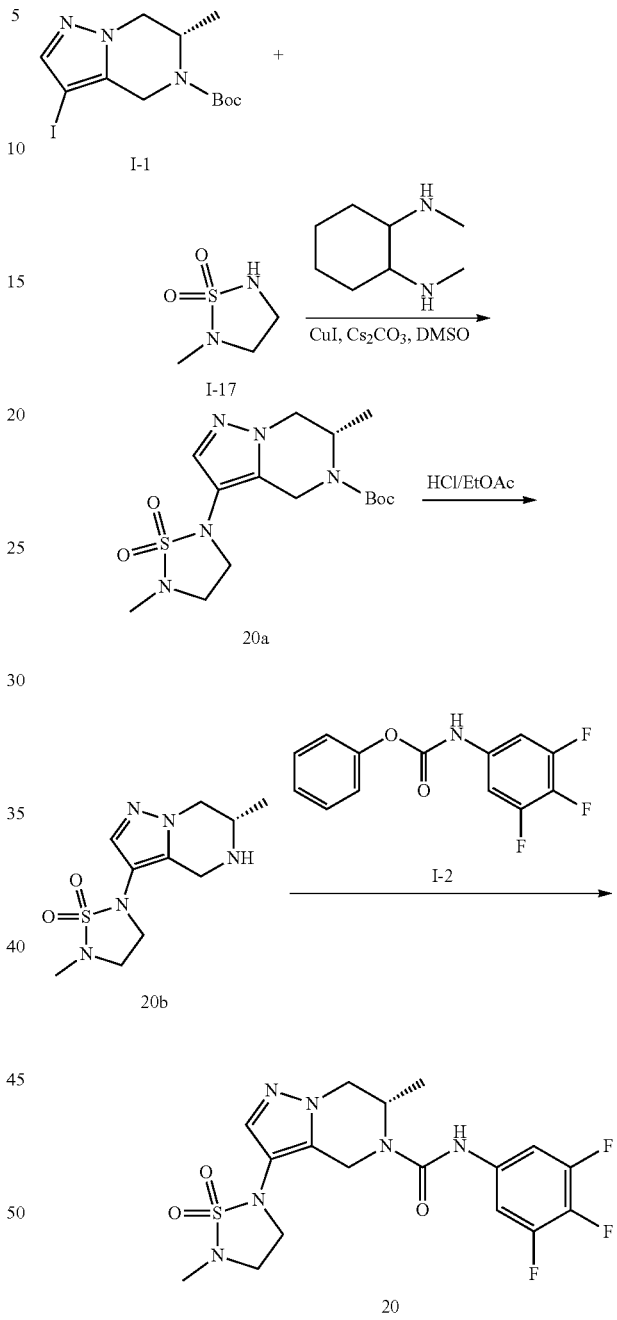

The title compound was prepared in analogy to Example 1 by using 2-methyl-1,2,5-thiadiazolidine 1,1-dioxide (intermediate I-17) instead of 1,2-thiazolidine 1,1-dioxide (compound 1a), N,N'-dimethyl-1,2-cyclohexanediamine instead of trans-N,N'-dimethyl-1,2-cyclohexanediamine, and Cs$_2$CO$_3$ instead of K$_2$CO$_3$. Example 20 (12 mg) was obtained as a white solid. $^1$H NMR (400 MHz, CDCl$_3$) δ 7.61 (s, 1H) 7.15 (dd, 2H) 6.78 (s, 1H) 5.06-5.16 (m, 1H) 4.99 (d, 1H) 4.53 (d, 1H) 4.27 (dd, 1H) 4.10 (d, 1H) 3.67-3.84 (m, 2H) 3.46-3.55 (m, 2H) 2.88 (s, 3H) 1.32 (d, 3H). MS obsd. (ESI+) [(M+H)+]: 445.

Example 21

(6S)-6-methyl-3-[(3S)-3-methyl-1,1-dioxo-thiazetidin-2-yl]-N-(3,4,5-trifluorophenyl)-6,7-dihydro-4H-pyrazolo[1,5-a]pyrazine-5-carboxamide

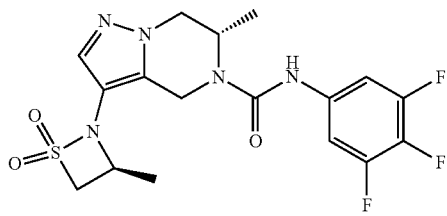 [SMILES: C[C@H]1Cn2ncc(N3[C@@H](C)CS3(=O)=O)c2CN1C(=O)Nc1cc(F)c(F)c(F)c1]

The title compound was prepared according to the following scheme:

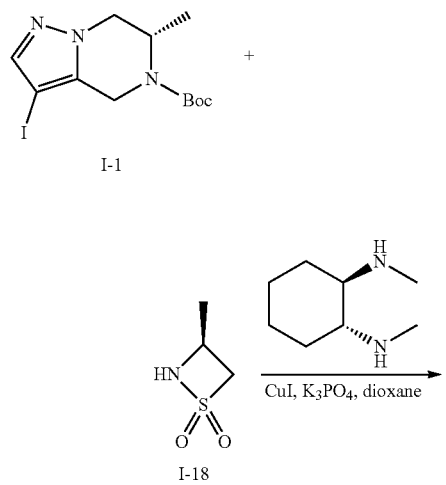

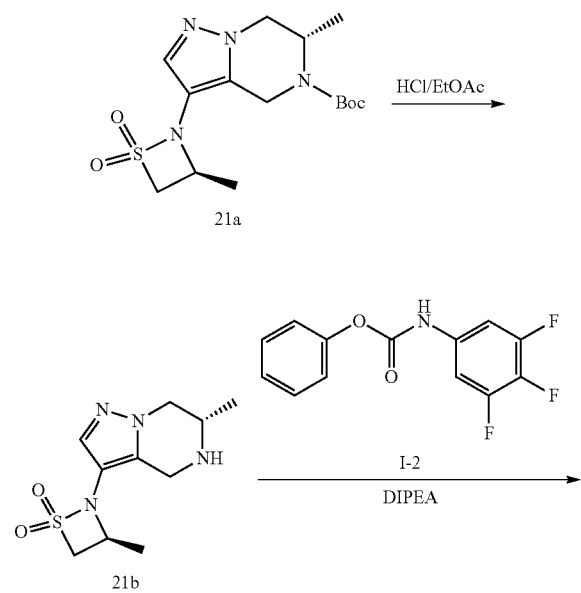

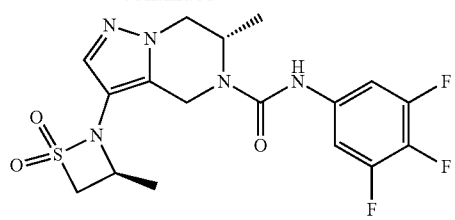

The title compound was prepared in analogy to Example 1 by using (3S)-3-methylthiazetidine 1,1-dioxide (intermediate I-18) instead of 1,2-thiazolidine 1,1-dioxide (compound 1a), $K_3PO_4$ instead of $K_2CO_3$, dioxane instead of DMSO (in step 1) and DIPEA instead of $Et_3N$ (in step 3). Example 21 (36 mg) was obtained as a white solid. $^1H$ NMR (400 MHz, METHANOL-$d_4$) 7.68 (s, 1H), 7.29 (dd, 2H), 5.12 (d, 1H), 5.02-4.92 (m, 1H), 4.58 (d, 1H), 4.39 (dd, 1H), 4.31 (dd, 1H), 4.17 (dd, 1H), 4.03-3.90 (m, 2H), 1.46 (d, 3H), 1.23 (d, 3H). MS obsd. (ESI$^+$) [(M+H)$^+$]: 430.

Example 22

(6S)-6-methyl-3-[(3S)-3-methyl-1,1-dioxo-1,2,5-thiadiazolidin-2-yl]-N-(3,4,5-trifluorophenyl)-6,7-dihydro-4H-pyrazolo[1,5-a]pyrazine-5-carboxamide

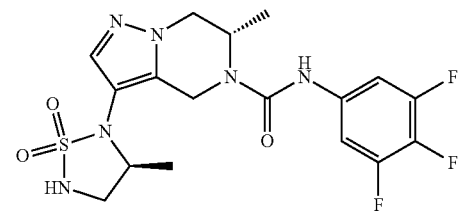 [SMILES: C[C@H]1Cn2ncc(N3[C@@H](C)CNS3(=O)=O)c2CN1C(=O)Nc1cc(F)c(F)c(F)c1]

The title compound was prepared according to the following scheme:

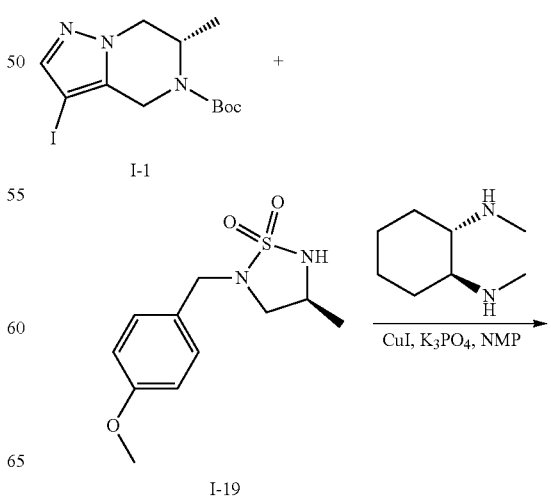

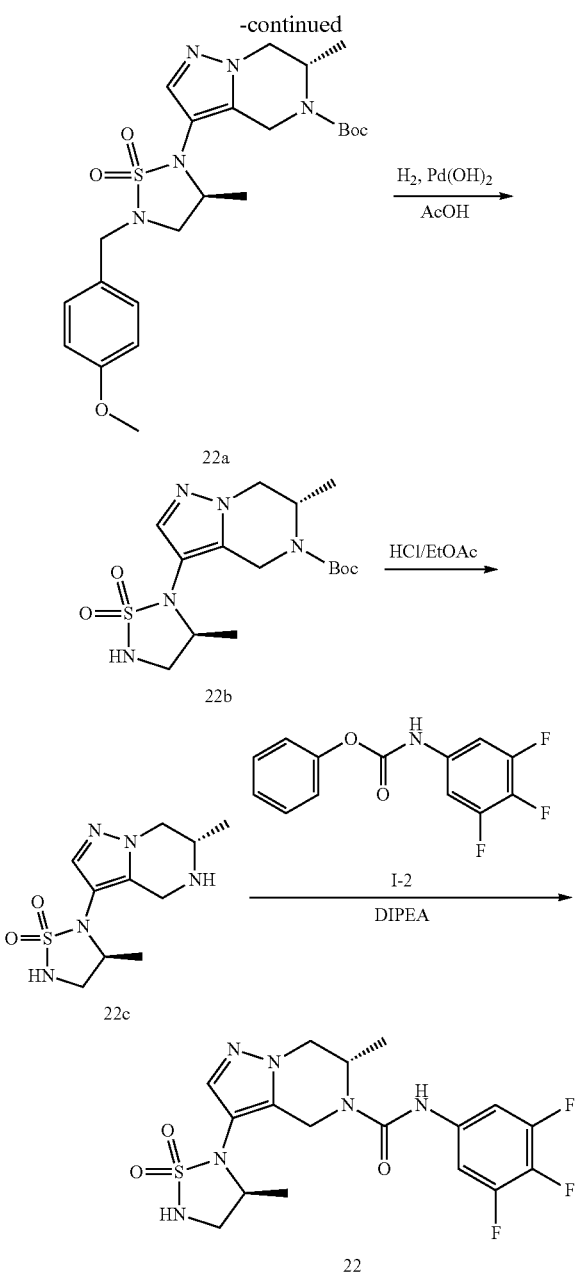

Step 1: Preparation of tert-butyl (6S)-3-[(3S)-5-[(4-methoxyphenyl)methyl]-3-methyl-1,1-dioxo-1,2,5-thiadiazolidin-2-yl]-6-methyl-6,7-dihydro-4H-pyrazolo[1,5-a]pyrazine-5-carboxylate (Compound 22a)

To a mixture of trans-N,N'-dimethyl-1,2-cyclohexanediamine (28.4 mg, 0.2 mmol), $K_3PO_4$ (413.9 mg, 1.95 mmol), CuI (38.1 mg, 0.02 mmol), (4S)-2-[(4-methoxyphenyl)methyl]-4-methyl-1,2,5-thiadiazolidine 1,1-dioxide (intermediate I-19, 250.0 mg, 0.98 mmol) in NMP (15.0 mL) was added, tert-butyl (6S)-3-iodo-6-methyl-6,7-dihydro-4H-pyrazolo[1,5-a]pyrazine-5-carboxylate (intermediate I-1, 355.9 mg, 0.98 mmol). The mixture was stirred at 120° C. for 16 hours. After being cooled to room temperature, the mixture was filtered. The filtrate was concentrated, and the residue was purified by column chromatography to give compound 22a (45.0 mg) as a yellow oil. MS obsd. (ESI⁺) [(M+H)⁺]: 492.

Step 2: Preparation of tert-butyl (6S)-6-methyl-3-[(3S)-3-methyl-1,1-dioxo-1,2,5-thiadiazolidin-2-yl]-6,7-dihydro-4H-pyrazolo[1,5-a]pyrazine-5-carboxylate (Compound 22b)

To a solution of compound 22a (20.0 mg, 0.04 mmol) in AcOH (5.0 mL) was added $Pd(OH)_2$ (2.0 mg) at 20° C. The mixture was stirred at 80° C. under $H_2$ (50 psi) for 64 hours, then filtered. The filtrate was concentrated to give compound 22b (30.0 mg, crude) as a colorless oil. MS obsd. (ESI⁺) [(M+H)⁺]: 372.

Step 3: Preparation of (3S)-3-methyl-2-[(6S)-6-methyl-4,5,6,7-tetrahydropyrazolo[1,5-a]pyrazin-3-yl]-1,2,5-thiadiazolidine 1,1-dioxide (Compound 22c)

To a solution of tert-butyl (6S)-6-methyl-3-[(3S)-3-methyl-1,1-dioxo-1,2,5-thiadiazolidin-2-yl]-6,7-dihydro-4H-pyrazolo[1,5-a]pyrazine-5-carboxylate (compound 22b, 30.0 mg, 0.08 mmol) in EtOAc (1.0 mL) was added HCl/EtOAc (3.0 mL) at 20° C. The reaction mixture was stirred at 20° C. for 2 hours, then concentrated to give compound 22c (25.0 mg, crude) as yellow solid. MS obsd. (ESI⁺) [(M+H)⁺]: 272.

Step 4: Preparation of (6S)-6-methyl-3-[(3S)-3-methyl-1,1-dioxo-1,2,5-thiadiazolidin-2-yl]-N-(3,4,5-trifluorophenyl)-6,7-dihydro-4H-pyrazolo[1,5-a]pyrazine-5-carboxamide (Example 22)

To a solution of (3S)-3-methyl-2-[(6S)-6-methyl-4,5,6,7-tetrahydropyrazolo[1,5-a]pyrazin-3-yl]-1,2,5-thiadiazolidine 1,1-dioxide (compound 22c, 25.0 mg, 0.08 mmol) and DIPEA (20.7 mg, 0.16 mmol) in DMF (1.0 mL) was added phenyl N-(3,4,5-trifluorophenyl)carbamate (intermediate I-2, 21.4 mg, 0.08 mmol) at 20° C. The reaction mixture was stirred at 20° C. for 2 hours, then partitioned between EtOAc (5.0 mL) and brine (3.0 mL). The organic layer was dried over anhydrous $Na_2SO_4$ and concentrated. The residue was purified by prep-HPLC to give example 22 as a colorless oil. ¹H NMR (400 MHz, DMSO-$d_6$) δ 9.57 (s, 1H), 7.62-7.56 (m, 2H), 7.54 (s, 1H), 5.13-5.05 (m, 1H), 5.03-4.95 (m, 1H), 4.41-4.32 (m, 1H), 4.30-4.23 (m, 1H), 4.13 (d, 1H), 3.93 (q, 1H), 3.64-3.56 (m, 1H), 3.03 (td, 1H), 1.12-1.07 (m, 6H). MS obsd. (ESI⁺) [(M+H)⁺]: 445.

Example 23

(6S)-3-[(3S)-3,4-dimethyl-1,1-dioxo-1,2,5-thiadiazolidin-2-yl]-6-methyl-N-(3,4,5-trifluorophenyl)-6,7-dihydro-4H-pyrazolo[1,5-a]pyrazine-5-carboxamide

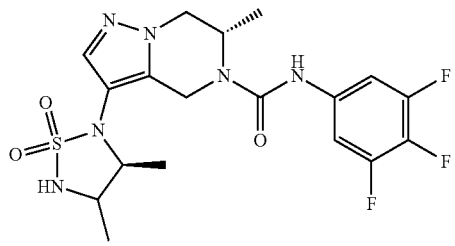 [SMILES: CC1NS(=O)(=O)N(c2cnn3c2CN(C(=O)Nc2cc(F)c(F)c(F)c2)[C@@H](C)C3)[C@H]1C]

The title compound was prepared according to the following scheme:

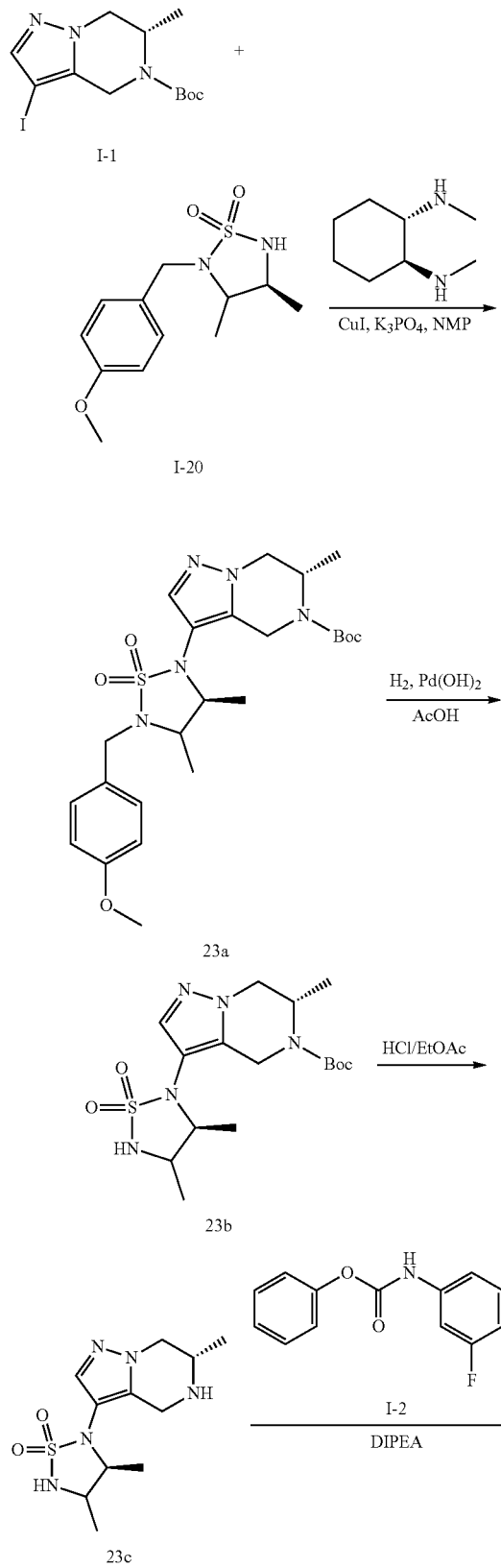

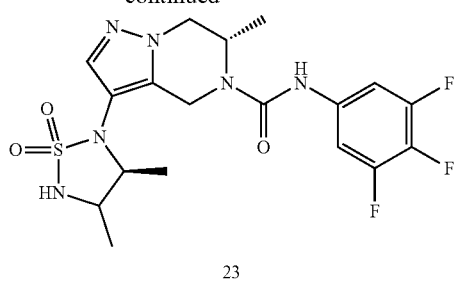

The title compound was prepared in analogy to Example 22 by using (4S)-2-[(4-methoxyphenyl)methyl]-3,4-dimethyl-1,2,5-thiadiazolidine 1,1-dioxide (intermediate I-20) instead of (4S)-2-[(4-methoxyphenyl)methyl]-4-methyl-1,2,5-thiadiazolidine 1,1-dioxide (intermediate I-19). Example 23 (8.7 mg) was obtained as a colorless oil. $^1$H NMR (400 MHz, DMSO-d$_6$) δ 9.21-9.06 (m, 1H), 7.57 (t, 1H), 7.43 (br dd, 1H), 5.05-4.92 (m, 1H), 4.85 (br s, 1H), 4.34 (br d, 1H), 4.26 (br d, 1H), 4.16 (br d, 1H), 3.90 (br s, 1H), 3.57-3.41 (m, 2H), 1.31-1.19 (m, 4H), 1.16-1.03 (m, 5H). MS obsd. (ESI$^+$) [(M+H)$^+$]: 459.

Example 24

(6S)-3-(3,3-dioxo-1,3,4-oxathiazinan-4-yl)-6-methyl-N-(3,4,5-trifluorophenyl)-6,7-dihydro-4H-pyrazolo[1,5-a]pyrazine-5-carboxamide

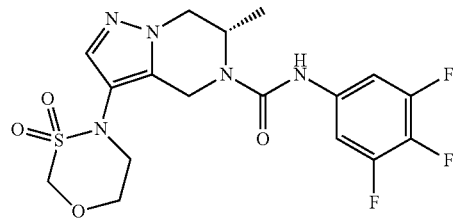 [SMILES: C[C@H]1Cn2ncc(N3CCOCS3(=O)=O)c2CN1C(=O)Nc1cc(F)c(F)c(F)c1]

The title compound was prepared according to the following scheme:

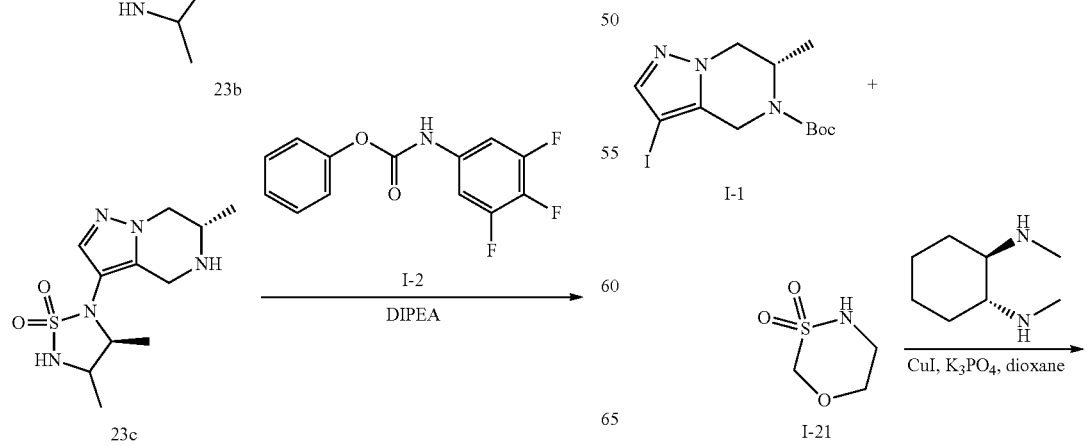

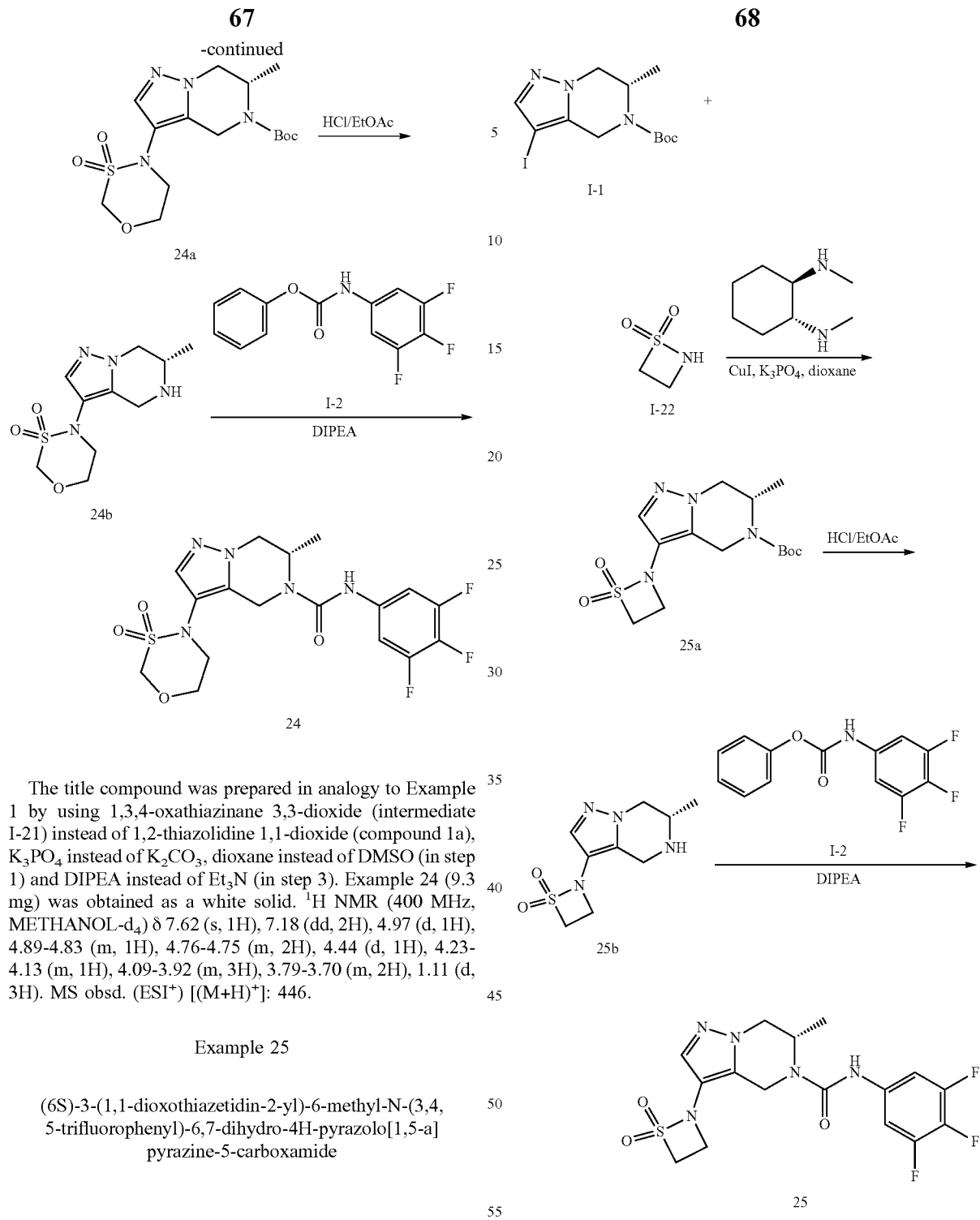

The title compound was prepared in analogy to Example 1 by using 1,3,4-oxathiazinane 3,3-dioxide (intermediate I-21) instead of 1,2-thiazolidine 1,1-dioxide (compound 1a), $K_3PO_4$ instead of $K_2CO_3$, dioxane instead of DMSO (in step 1) and DIPEA instead of $Et_3N$ (in step 3). Example 24 (9.3 mg) was obtained as a white solid. $^1$H NMR (400 MHz, METHANOL-$d_4$) δ 7.62 (s, 1H), 7.18 (dd, 2H), 4.97 (d, 1H), 4.89-4.83 (m, 1H), 4.76-4.75 (m, 2H), 4.44 (d, 1H), 4.23-4.13 (m, 1H), 4.09-3.92 (m, 3H), 3.79-3.70 (m, 2H), 1.11 (d, 3H). MS obsd. (ESI$^+$) [(M+H)$^+$]: 446.

Example 25

(6S)-3-(1,1-dioxothiazetidin-2-yl)-6-methyl-N-(3,4,5-trifluorophenyl)-6,7-dihydro-4H-pyrazolo[1,5-a]pyrazine-5-carboxamide

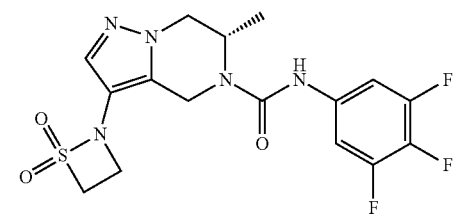 [SMILES: C[C@H]1Cn2ncc(N3CCS3(=O)=O)c2CN1C(=O)Nc1cc(F)c(F)c(F)c1]

The title compound was prepared according to the following scheme:

The title compound was prepared in analogy to Example 1 by using thiazetidine 1,1-dioxide (intermediate I-22) instead of 1,2-thiazolidine 1,1-dioxide (compound 1a), $K_3PO_4$ instead of $K_2CO_3$, dioxane instead of DMSO (in step 1) and DIPEA instead of $Et_3N$ (in step 3). Example 25 (8.5 mg) was obtained as a white solid. $^1$H NMR (400 MHz, METHANOL-$d_4$) δ 7.68 (s, 1H), 7.30 (dd, 2H), 5.13 (d, 1H), 4.96 (t, 1H), 4.56 (d, 1H), 4.38-4.26 (m, 3H), 4.19-4.13 (m, 1H), 3.69 (dt, 2H), 1.24 (d, 3H). MS obsd. (ESI$^+$) [(M+H)$^+$]: 416.

Example 26

(6S)-3-(4-hydroxy-1,1-dioxo-1,2,6-thiadiazinan-2-yl)-6-methyl-N-(3,4,5-trifluorophenyl)-6,7-dihydro-4H-pyrazolo[1,5-a]pyrazine-5-carboxamide

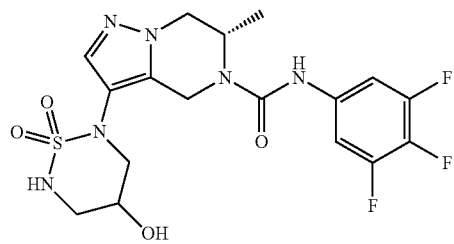 [SMILES: C[C@H]1Cn2ncc(N3CC(O)CNS3(=O)=O)c2CN1C(=O)Nc1cc(F)c(F)c(F)c1]

The title compound was prepared according to the following scheme:

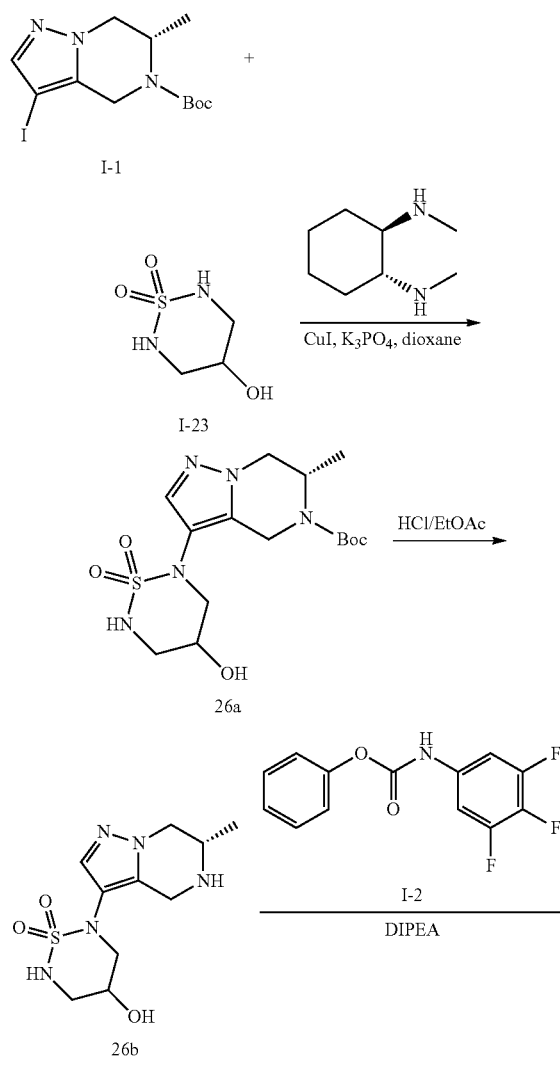

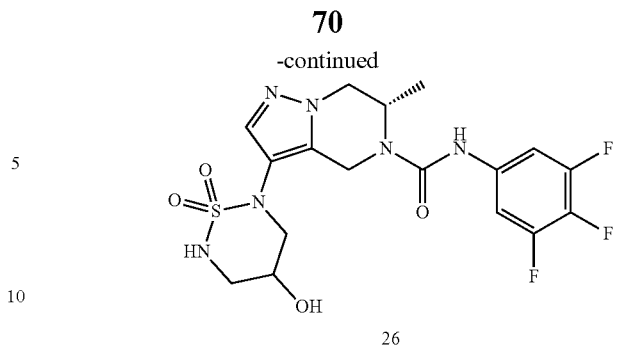

The title compound was prepared in analogy to Example 1 by using 1,1-dioxo-1,2,6-thiadiazinan-4-ol (intermediate I-23) instead of 1,2-thiazolidine 1,1-dioxide (compound 1a), $K_3PO_4$ instead of $K_2CO_3$, dioxane instead of DMSO (in step 1) and DIPEA instead of $Et_3N$ (in step 3). Example 26 (3.4 mg) was obtained as a white solid. $^1$H NMR (400 MHz, CHLOROFORM-d) δ 7.60 (d, 1H), 7.10-7.00 (m, 2H), 5.01-4.82 (m, 2H), 4.51-4.35 (m, 1H), 4.25-4.14 (m, 1H), 4.11-3.89 (m, 3H), 3.81 (d, 1H), 3.52-3.39 (m, 2H), 1.22 (d, 3H). MS obsd. (ESI$^+$) [(M+H)$^+$]: 461.

Example 27

(6S)-3-(1,1-dioxo-1,2,6-thiadiazinan-2-yl)-6-methyl-N-(3,4,5-trifluorophenyl)-6,7-dihydro-4H-pyrazolo[1,5-a]pyrazine-5-carboxamide

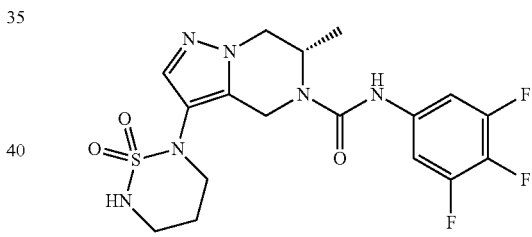

The title compound was prepared according to the following scheme:

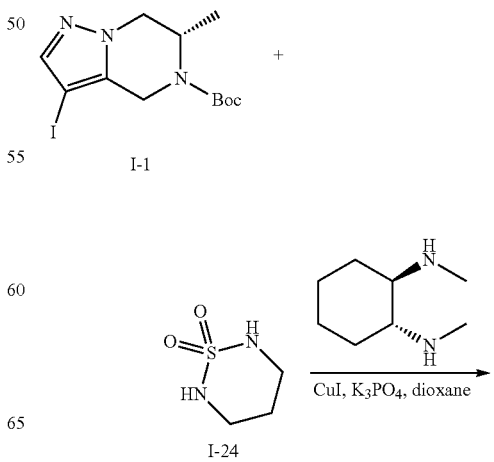

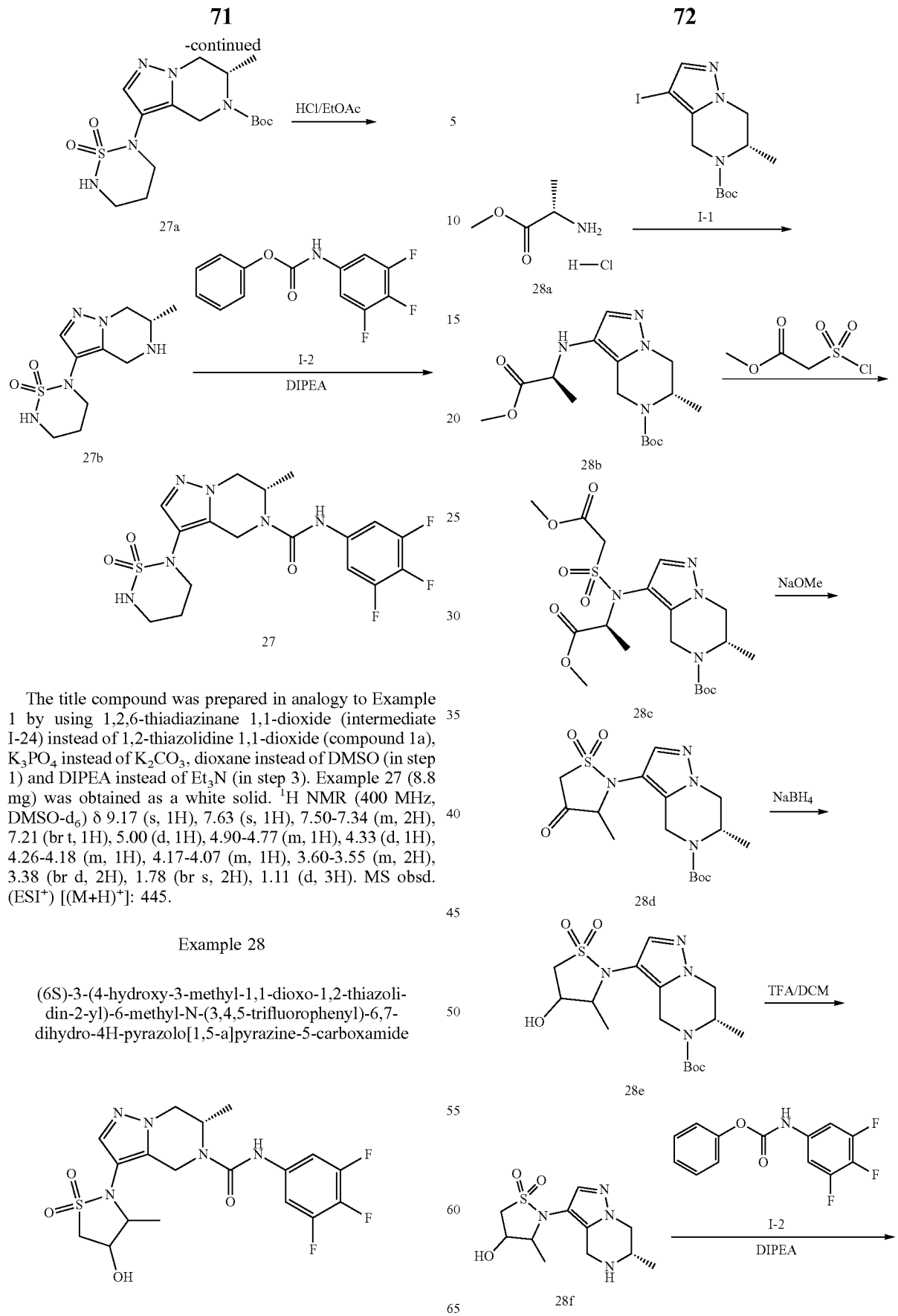

The title compound was prepared in analogy to Example 1 by using 1,2,6-thiadiazinane 1,1-dioxide (intermediate I-24) instead of 1,2-thiazolidine 1,1-dioxide (compound 1a), $K_3PO_4$ instead of $K_2CO_3$, dioxane instead of DMSO (in step 1) and DIPEA instead of $Et_3N$ (in step 3). Example 27 (8.8 mg) was obtained as a white solid. $^1$H NMR (400 MHz, DMSO-$d_6$) δ 9.17 (s, 1H), 7.63 (s, 1H), 7.50-7.34 (m, 2H), 7.21 (br t, 1H), 5.00 (d, 1H), 4.90-4.77 (m, 1H), 4.33 (d, 1H), 4.26-4.18 (m, 1H), 4.17-4.07 (m, 1H), 3.60-3.55 (m, 2H), 3.38 (br d, 2H), 1.78 (br s, 2H), 1.11 (d, 3H). MS obsd. (ESI$^+$) [(M+H)$^+$]: 445.

Example 28

(6S)-3-(4-hydroxy-3-methyl-1,1-dioxo-1,2-thiazoli-din-2-yl)-6-methyl-N-(3,4,5-trifluorophenyl)-6,7-dihydro-4H-pyrazolo[1,5-a]pyrazine-5-carboxamide

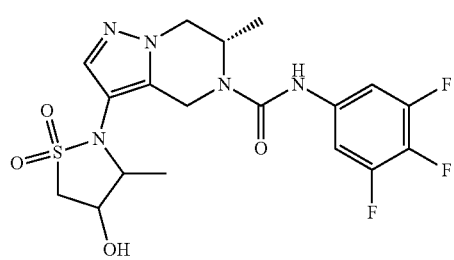 [SMILES: CC1C(O)CS(=O)(=O)N1c1cnn2c1CN(C(=O)Nc1cc(F)c(F)c(F)c1)[C@@H](C)C2]

The title compound was prepared according to the following scheme:

-continued

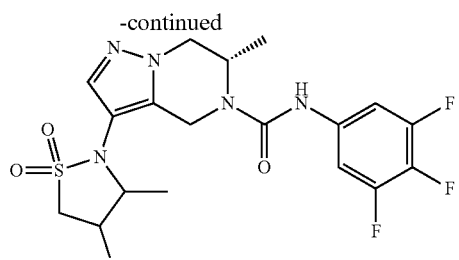

28

Step 1: Preparation of tert-butyl (6S)-3-[[(1S)-2-methoxy-1-methyl-2-oxo-ethyl]amino]-6-methyl-6,7-dihydro-4H-pyrazolo[1,5-a]pyrazine-5-carboxylate (Compound 28b)

An oven-dried resealable Schlenk tube was charged with (S)-tert-butyl 3-iodo-6-methyl-6,7-dihydropyrazolo[1,5-a]pyrazine-5(4H)-carboxylate (intermediate I-1, 1 g, 2.75 mmol), $K_3PO_4$ (1.46 g, 6.88 mmol), CuI (105 mg, 0.55 mmol) and 2-((2,6-dimethylphenyl)amino)-2-oxoacetic acid (213 mg, 1.10 mmol), then evacuated and backfilled with argon, followed by addition of (S)-methyl 2-aminopropanoate hydrochloride (compound 28a, 423 mg, 3.03 mmol) in DMSO (10.0 mL). The mixture was stirred at 110° C. for 2 hours under microwave, then quenched with saturated aqueous $NH_4Cl$ and diluted with EtOAc. The organic layer was separated and washed with saturated aqueous $NH_4Cl$ and brine, dried over $Na_2SO_4$ and concentrated. The residue was purified by column chromatography to afford compound 28b (323 mg). LCMS (M+H$^+$): 339.

Step 2: Preparation of tert-butyl (6S)-3-[[(1S)-2-methoxy-1-methyl-2-oxo-ethyl]-(2-methoxy-2-oxo-ethyl)sulfonyl-amino]-6-methyl-6,7-dihydro-4H-pyrazolo[1,5-a]pyrazine-5-carboxylate (Compound 28c)

To a solution of mixture of tert-butyl (6S)-3-[[(1S)-2-methoxy-1-methyl-2-oxo-ethyl]amino]-6-methyl-6,7-dihydro-4H-pyrazolo[1,5-a]pyrazine-5-carboxylate (compound 28b, 323 mg, 0.954 mmol) and DIPEA (370 mg, 2.86 mmol) in DCM (10 mL) was added methyl 2-(chlorosulfonyl)acetate (181 mg, 1.05 mmol). The mixture was stirred at r.t. overnight and concentrated. The residue was purified by flash chromatography to afford compound 28c (319 mg). LCMS (M+H$^+$): 475.

Step 3: Preparation of tert-butyl (6S)-6-methyl-3-(3-methyl-1,1,4-trioxo-1,2-thiazolidin-2-yl)-6,7-dihydro-4H-pyrazolo[1,5-a]pyrazine-5-carboxylate (Compound 28d)

Sodium methanolate (182 mg, 3.36 mmol) was added to a solution of tert-butyl (6S)-3-[[(1 S)-2-methoxy-1-methyl-2-oxo-ethyl]-(2-methoxy-2-oxo-ethyl)sulfonyl-amino]-6-methyl-6,7-dihydro-4H-pyrazolo[1,5-a]pyrazine-5-carboxylate (compound 28c, 319 mg, 672 µmol) in MeOH (10 mL). The mixture was stirred at r.t. for 24 hours. The mixture was concentrated and the residue was acidified to pH=4 with hydrochloric acid. The resulting mixture was extracted with ethyl acetate. The organic phase was dried over anhydrous $Na_2SO_4$ and concentrated. The residue was purified with column chromatography to afford compound 28d (80 mg). LCMS (M+H$^+$): 385.

Step 4: Preparation of tert-butyl (6S)-3-(4-hydroxy-3-methyl-1,1-dioxo-1,2-thiazolidin-2-yl)-6-methyl-6,7-dihydro-4H-pyrazolo[1,5-a]pyrazine-5-carboxylate (Compound 28e)

$NaBH_4$ (11.2 mg, 297 µmol) was added to a solution of tert-butyl (6S)-6-methyl-3-(3-methyl-1,1,4-trioxo-1,2-thiazolidin-2-yl)-6,7-dihydro-4H-pyrazolo[1,5-a]pyrazine-5-carboxylate (compound 28d, 76 mg, 198 µmol) in MeOH (10 mL). The mixture was stirred at r.t. for 1 hour, then concentrated. The residue was partitioned between water and ethyl acetate. The organic layer was dried over anhydrous $Na_2SO_4$ and concentrated to give compound 28e (69 mg, crude), which was used in the next step without further purification. LCMS (M+H$^+$): 387.

Step 5: Preparation of 3-methyl-2-[(6S)-6-methyl-4,5,6,7-tetrahydropyrazolo[1,5-a]pyrazin-3-yl]-1,1-dioxo-1,2-thiazolidin-4-ol (Compound 28f)

A mixture of tert-butyl (6S)-3-(4-hydroxy-3-methyl-1,1-dioxo-1,2-thiazolidin-2-yl)-6-methyl-6,7-dihydro-4H-pyrazolo[1,5-a]pyrazine-5-carboxylate (compound 28e, 69 mg, 623 mol), 2,2,2-trifluoroacetic acid (2.0 mL) in DCM (5.0 mL) was stirred at room temperature for 30 minutes. The reaction mixture was concentrated to afford crude compound 28f (105 mg). LCMS (M+H$^+$): 287.

Step 6: Preparation of (6S)-3-(4-hydroxy-3-methyl-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide To a solution of 3-methyl-2-[(6S)-6-methyl-4,5,6,7-tetrahydropyrazolo[1,5-a]pyrazin-3-yl]-1,1-dioxo-1,2-thiazolidin-4-ol (compound 28f, 105 mg, crude) in DCM (3.0 mL) was added DIPEA (0.5 mL) and phenyl N-(3,4,5-trifluorophenyl)carbamate (intermediate I-2, 57.2 mg, 214 µmol). The reaction mixture was stirred at 50° C. for 3 hours, then partitioned between ice-water and DCM. The aqueous layer was extracted with DCM. The combined organic layer was concentrated. The residue was purified by prep-HPLC to afford Example 28-1 (35 mg) and Example 28-2 (6 mg).

Example 28-1: $^1$H NMR (400 MHz, METHANOL-d$_4$) δ 7.63 (d, 1H), 7.30 (br dd, 2H), 5.07 (dd, 1H), 5.01-4.94 (m, 1H), 4.59 (br d, 1H), 4.33 (td, 1H), 4.22-4.13 (m, 2H), 3.99-3.92 (m, 1H), 3.74 (dd, 1H), 3.49-3.42 (m, 1H), 1.32 (t, 3H), 1.27-1.21 (m, 3H). LCMS (M+H$^+$): 460.

Example 28-2: $^1$H NMR (400 MHz, METHANOL-d$_4$) δ 7.66-7.61 (m, 1H), 7.29 (dd, 2H), 5.05 (d, 1H), 5.00-4.94 (m, 1H), 4.58-4.50 (m, 1H), 4.32-4.26 (m, 1H), 4.20-4.14 (m, 2H), 3.83-3.76 (m, 1H), 3.66-3.61 (m, 1H), 1.30-1.19 (m, 6H). LCMS (M+H$^+$): 460.

Example 29

(6S)—N-[2-(difluoromethyl)-4-pyridyl]-3-(4-hydroxy-3-methyl-1,1-dioxo-1,2-thiazolidin-2-yl)-6-methyl-6,7-dihydro-4H-pyrazolo[1,5-a]pyrazine-5-carboxamide

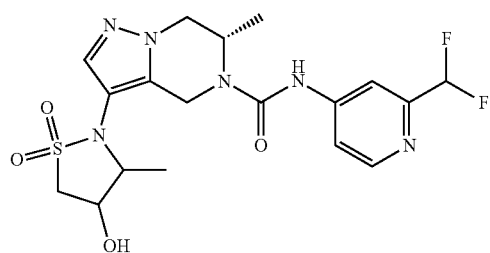 [SMILES: CC1C(O)CS(=O)(=O)N1c1cnn2c1CN(C(=O)Nc1ccnc(C(F)F)c1)[C@@H](C)C2]

The title compound was prepared according to the following scheme:

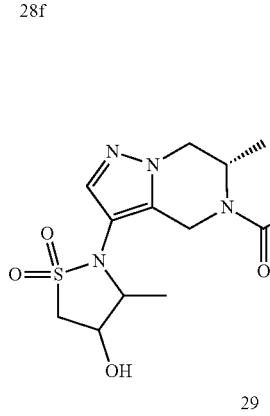

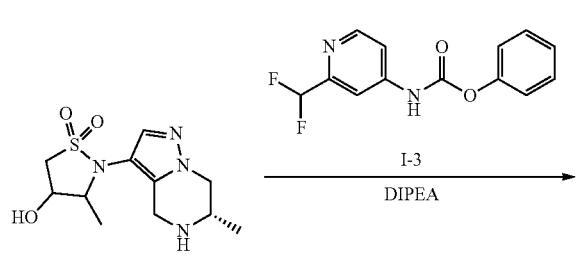

To a solution of 3-methyl-2-[(6S)-6-methyl-4,5,6,7-tetrahydropyrazolo[1,5-a]pyrazin-3-yl]-1,1-dioxo-1,2-thiazolidin-4-ol (compound 28f, 53 mg, crude) in DCM (3.0 mL) was added DIPEA (0.5 mL) and phenyl N-[2-(difluoromethyl)-4-pyridyl]carbamate (intermediate I-3, 28 mg, 106 μmol). The reaction mixture was stirred at 50° C. for 1 hour, then partitioned between ice-water and DCM. The aqueous layer was extracted with DCM. The combined organic layer was concentrated. The residue was purified by prep-HPLC to afford Example 29 (7.6 mg). $^1$H NMR (400 MHz, METHANOL-$d_4$) δ 8.35 (d, 1H), 7.80 (d, 1H), 7.61 (br d, 1H), 7.56 (d, 1H), 6.75-6.43 (m, 1H), 5.04 (dd, 1H), 4.96-4.89 (m, 1H), 4.51 (dd, 1H), 4.31-4.17 (m, 2H), 4.11 (dd, 1H), 3.72 (dd, 1H), 3.56 (dt, 1H), 3.21-3.15 (m, 1H), 1.20-1.13 (m, 6H). LCMS (M+H$^+$): 457.

Example 30

(6S)-6-methyl-3-(3-methyl-1,1-dioxo-4-pyrimidin-2-yloxy-1,2-thiazolidin-2-yl)-N-(3,4,5-trifluorophenyl)-6,7-dihydro-4H-pyrazolo[1,5-a]pyrazine-5-carboxamide

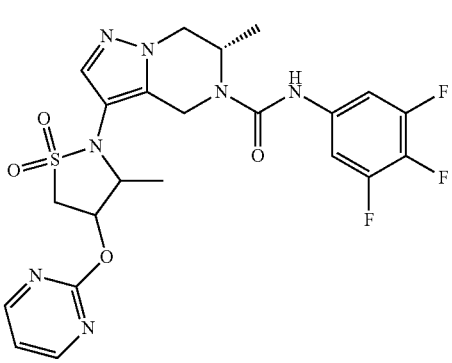 [SMILES: CC1C(Oc2ncccn2)CS(=O)(=O)N1c1cnn2c1CN(C(=O)Nc1cc(F)c(F)c(F)c1)[C@@H](C)C2]

The title compound was prepared according to the following scheme:

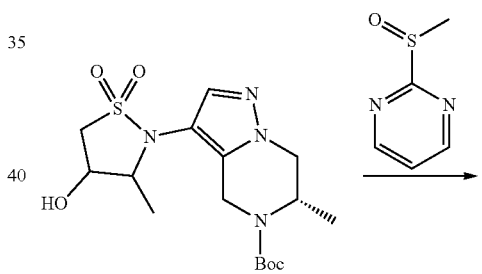

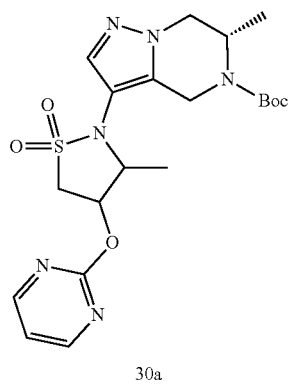

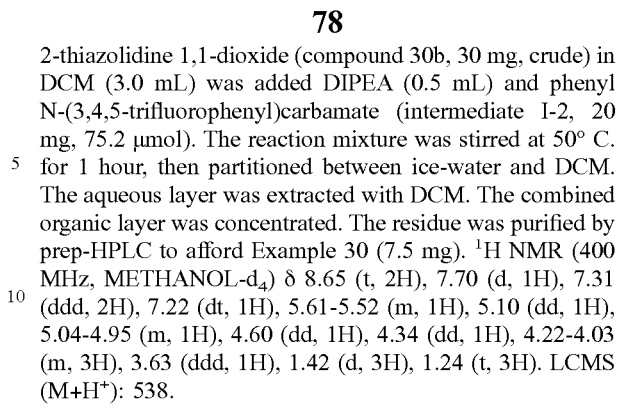

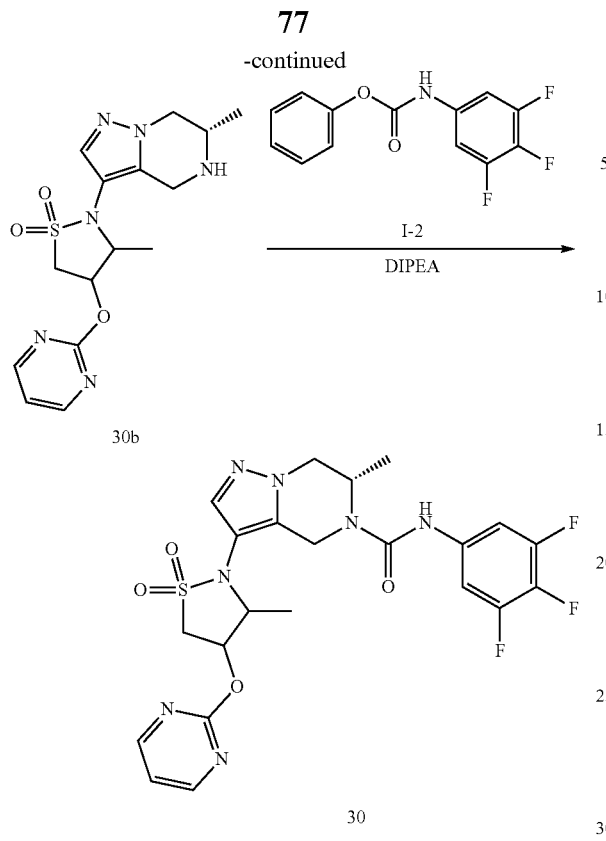

Step 1: Preparation of tert-butyl (6S)-6-methyl-3-(3-methyl-1,1-dioxo-4-pyrimidin-2-yloxy-1,2-thiazolidin-2-yl)-6,7-dihydro-4H-pyrazolo[1,5-a]pyrazine-5-carboxylate (Compound 30a)

To a mixture of $K_2CO_3$ (32.2 mg, 233 μmol) and tert-butyl (6S)-3-(4-hydroxy-3-methyl-1,1-dioxo-1,2-thiazolidin-2-yl)-6-methyl-6,7-dihydro-4H-pyrazolo[1,5-a]pyrazine-5-carboxylate (compound 28e, 30 mg, 77.6 μmol) in dioxane (10 mL) was added 2-(methylsulfinyl)pyrimidine (22.1 mg, 155 μmol). The mixture was stirred at r.t overnight, then concentrated. The residue was partitioned between water and ethyl acetate. The organic layer was dried over anhydrous $Na_2SO_4$ and concentrated. The residue was purified by column chromatography to afford compound 30a (29 mg). LCMS (M+H$^+$): 465.

Step 2: Preparation of 3-methyl-2-[(6S)-6-methyl-4,5,6,7-tetrahydropyrazolo[1,5-a]pyrazin-3-yl]-4-pyrimidin-2-yloxy-1,2-thiazolidine 1,1-dioxide (Compound 30b)

A mixture of tert-butyl (6S)-6-methyl-3-(3-methyl-1,1-dioxo-4-pyrimidin-2-yloxy-1,2-thiazolidin-2-yl)-6,7-dihydro-4H-pyrazolo[1,5-a]pyrazine-5-carboxylate (compound 30a, 25 mg, 53.8 μmol) and 2,2,2-trifluoroacetic acid (2.0 mL) in DCM (5.0 mL) was stirred at room temperature for 30 minutes. The reaction mixture was concentrated to afford compound 30b (30 mg, crude). LCMS (M+H$^+$): 365.

Step 3: Preparation of (6S)-6-methyl-3-(3-methyl-1,1-dioxo-4-pyrimidin-2-yloxy-1,2-thiazolidin-2-yl)-N-(3,4,5-trifluorophenyl)-6,7-dihydro-4H-pyrazolo[1,5-a]pyrazine-5-carboxamide (Example 30)

To a solution of 3-methyl-2-[(6S)-6-methyl-4,5,6,7-tetrahydropyrazolo[1,5-a]pyrazin-3-yl]-4-pyrimidin-2-yloxy-1, 2-thiazolidine 1,1-dioxide (compound 30b, 30 mg, crude) in DCM (3.0 mL) was added DIPEA (0.5 mL) and phenyl N-(3,4,5-trifluorophenyl)carbamate (intermediate I-2, 20 mg, 75.2 μmol). The reaction mixture was stirred at 50° C. for 1 hour, then partitioned between ice-water and DCM. The aqueous layer was extracted with DCM. The combined organic layer was concentrated. The residue was purified by prep-HPLC to afford Example 30 (7.5 mg). $^1$H NMR (400 MHz, METHANOL-d$_4$) δ 8.65 (t, 2H), 7.70 (d, 1H), 7.31 (ddd, 2H), 7.22 (dt, 1H), 5.61-5.52 (m, 1H), 5.10 (dd, 1H), 5.04-4.95 (m, 1H), 4.60 (dd, 1H), 4.34 (dd, 1H), 4.22-4.03 (m, 3H), 3.63 (ddd, 1H), 1.42 (d, 3H), 1.24 (t, 3H). LCMS (M+H$^+$): 538.

Example 31

(6S)-3-(4-methoxy-3-methyl-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide

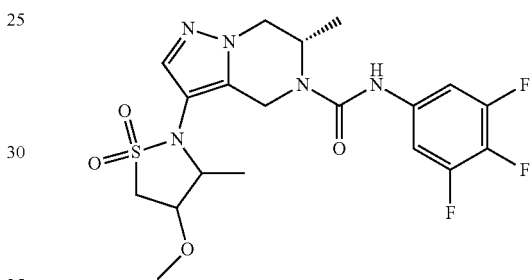

The title compound was prepared according to the following scheme:

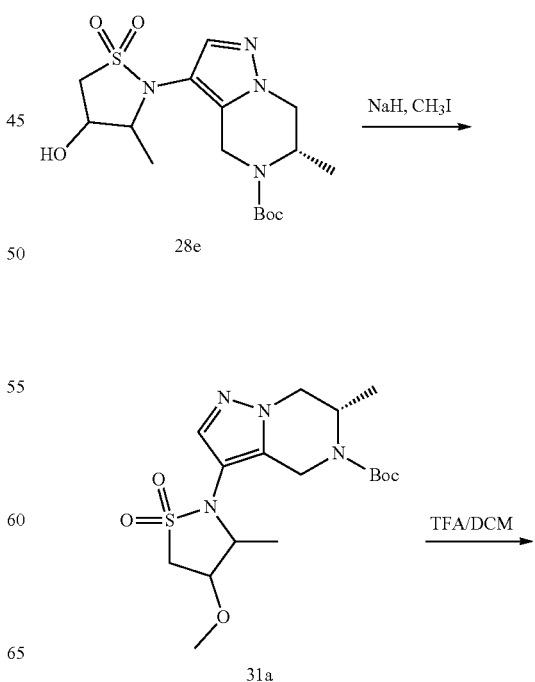

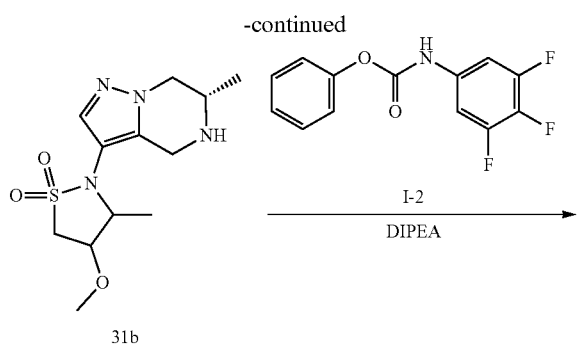

Step 1: Preparation of tert-butyl (6S)-3-(4-methoxy-3-methyl-1,1-dioxo-1,2-thiazolidin-2-yl)-6-methyl-6,7-dihydro-4H-pyrazolo[1,5-a]pyrazine-5-carboxylate (Compound 31a)

NaH (60% in oil, 10 mg, 259 μmol) was added to a solution of tert-butyl (6S)-3-(4-hydroxy-3-methyl-1,1-dioxo-1,2-thiazolidin-2-yl)-6-methyl-6,7-dihydro-4H-pyrazolo[1,5-a]pyrazine-5-carboxylate (compound 28e, 50 mg, 129 μmol) in THF (10 mL) at 0° C. The mixture was stirred at 0° C. for 5 minutes, then iodomethane (55 mg, 388 μmol) was added in. The reaction mixture was stirred at r.t. overnight, then concentrated. The residue was partitioned between water and ethyl acetate. The organic layer was dried over anhydrous Na$_2$SO$_4$ and concentrated. The residue was purified by column chromatography to afford compound 31a (42 mg, crude). LCMS (M+H$^+$): 401.

Step 2: Preparation of 4-methoxy-3-methyl-2-[(6S)-6-methyl-4,5,6,7-tetrahydropyrazolo[1,5-a]pyrazin-3-yl]-1,2-thiazolidine 1,1-dioxide (Compound 31b)

A mixture of tert-butyl (6S)-3-(4-methoxy-3-methyl-1,1-dioxo-1,2-thiazolidin-2-yl)-6-methyl-6,7-dihydro-4H-pyrazolo[1,5-a]pyrazine-5-carboxylate (compound 31a, 25 mg, crude) and 2,2,2-trifluoroacetic acid (2.0 mL) in DCM (5.0 mL) was stirred at room temperature for 30 minutes. The reaction mixture was concentrated to afford compound 31b (25 mg). LCMS (M+H$^+$): 301.

Step 3: Preparation of (6S)-3-(4-methoxy-3-methyl-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide (Example 31)

To a solution of 4-methoxy-3-methyl-2-[(6S)-6-methyl-4,5,6,7-tetrahydropyrazolo[1,5-a]pyrazin-3-yl]-1,2-thiazolidine 1,1-dioxide (compound 31b, 25 mg, crude) in DCM (3.0 mL) was added DIPEA (0.5 mL) and phenyl N-(3,4,5-trifluorophenyl)carbamate (intermediate I-2, 16 mg, 60 μmol). The reaction mixture was stirred at 50° C. for 1 hour, then partitioned between ice-water and DCM. The aqueous layer was extracted with DCM. The combined organic layer was concentrated. The residue was purified by prep-HPLC to afford Example 31 (8.2 mg). $^1$H NMR (400 MHz, METHANOL-d$_4$) δ 7.64 (d, 1H), 7.29 (dd, 2H), 5.05 (dd, 1H), 5.00-4.93 (m, 1H), 4.53 (d, 1H), 4.33 (td, 1H), 4.17 (dd, 1H), 4.03 (td, 1H), 3.82 (m, 1H), 3.72 (dt, 1H), 3.50-3.46 (m, 3H), 3.41 (ddd, 1H), 1.29 (dd, 3H), 1.26-1.21 (m, 3H). LCMS (M+H$^+$): 474.

Example 32

(6S)—N-[2-(difluoromethyl)-4-pyridyl]-3-(4-methoxy-3-methyl-1,1-dioxo-1,2-thiazolidin-2-yl)-6-methyl-6,7-dihydro-4H-pyrazolo[1,5-a]pyrazine-5-carboxamide

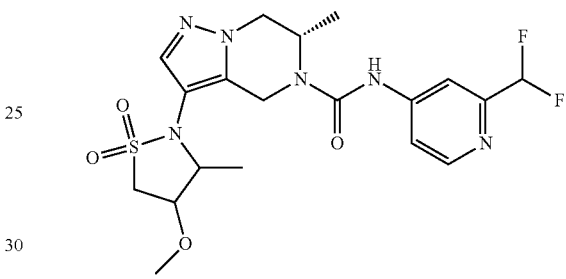

The title compound was prepared according to the following scheme:

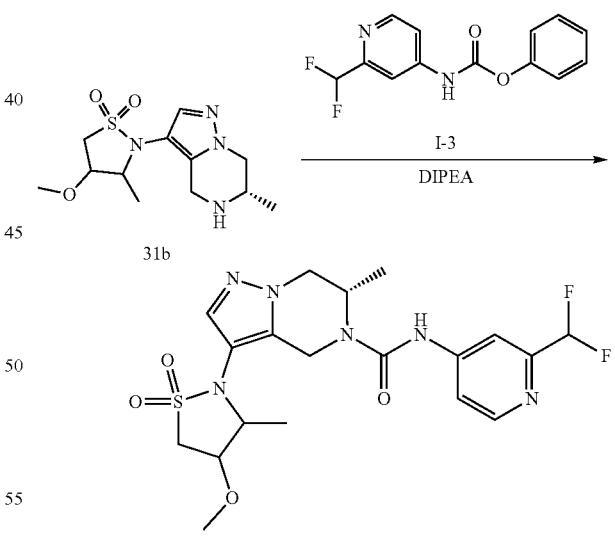

To a solution of 4-methoxy-3-methyl-2-[(6S)-6-methyl-4,5,6,7-tetrahydropyrazolo[1,5-a]pyrazin-3-yl]-1,2-thiazolidine 1,1-dioxide (compound 31b, 25 mg, crude) in DCM (3.0 mL) was added DIPEA (0.5 mL) and phenyl N-[2-(difluoromethyl)-4-pyridyl]carbamate (intermediate I-3, 16 mg, 60 μmol). The reaction mixture was stirred at 50° C. for 1 hour, then partitioned between ice-water and DCM. The aqueous layer was extracted with DCM. The combined organic layer was concentrated. The residue was purified by prep-HPLC to afford Example 32-1 (8.4 mg) and Example 32-2 (1.9 mg).

Example 32-1: $^1$H NMR (400 MHz, METHANOL-$d_4$) δ 8.53 (br s, 1H), 8.02 (s, 1H), 7.83 (br d, 1H), 7.68 (br s, 1H), 7.00-6.66 (m, 1H), 5.13 (dd, 1H), 5.01 (br dd, 1H), 4.59 (d, 1H), 4.35 (br s, 1H), 4.21 (br d, 1H), 4.07-4.00 (m, 1H), 3.87-3.79 (m, 1H), 3.75-3.69 (m, 1H), 3.47 (d, 3H), 3.41 (ddd, 1H), 1.28 (dt, 6H). LCMS (M+H$^+$): 471.

Example 32-2: $^1$H NMR (400 MHz, METHANOL-$d_4$) δ 8.31 (d, 1H), 7.77 (d, 1H), 7.57 (br d, 1H), 7.53-7.49 (m, 1H), 6.75-6.39 (m, 1H), 5.04-4.96 (m, 1H), 4.95-4.87 (m, 1H), 4.52-4.43 (m, 1H), 4.28-4.20 (m, 1H), 4.15 (q, 1H), 4.07 (br d, 1H), 3.93 (dd, 1H), 3.55 (d, 2H), 3.35 (s, 3H), 1.16-1.06 (m, 6H). LCMS (M+H$^+$): 471.

Example 33

3-(1,1-dioxo-1,2-thiazolidin-2-yl)-6-methyl-N-(3,4,5-trifluorophenyl)-6,7-dihydro-4H-triazolo[1,5-a]pyrazine-5-carboxamide

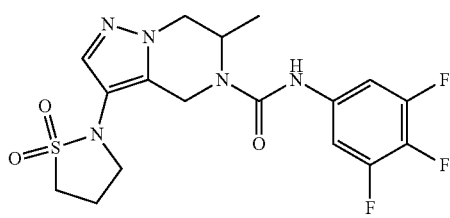 [SMILES: CC1Cn2ncc(N3CCCS3(=O)=O)c2CN1C(=O)Nc1cc(F)c(F)c(F)c1]

The title compound was prepared according to the following scheme:

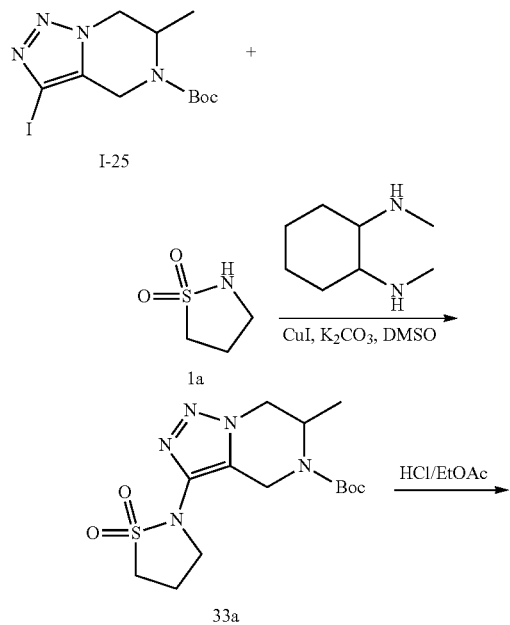

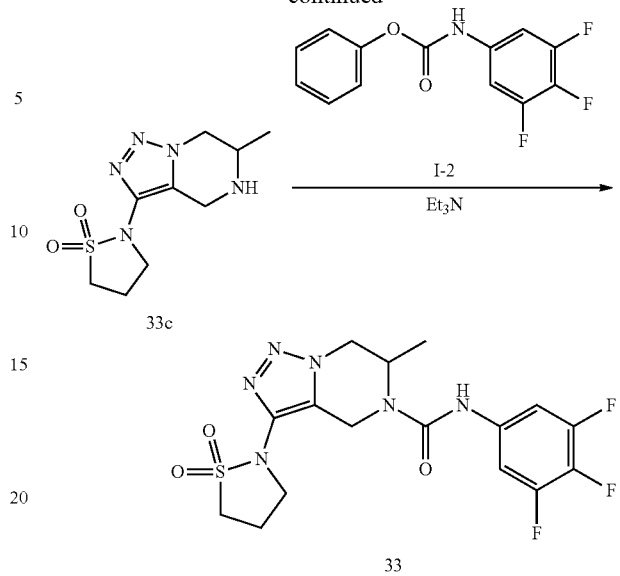

The title compound was prepared in analogy to Example 1 by using tert-butyl 3-iodo-6-methyl-6,7-dihydro-4H-triazolo[1,5-a]pyrazine-5-carboxylate (intermediate I-25) instead of tert-butyl (6S)-3-iodo-6-methyl-6,7-dihydro-4H-pyrazolo[1,5-a]pyrazine-5-carboxylate (intermediate I-1), and N,N'-dimethyl-1,2-cyclohexanediamine instead of trans-N,N'-dimethyl-1,2-cyclohexanediamine in step 1.

Example 33-1 (4.2 mg, from intermediate I-25-1) was obtained as a white solid. $^1$H NMR (400 MHz, CDCl$_3$) δ ppm 7.16 (dd, 2H), 6.95 (s, 1H), 5.21 (m, 1H), 5.02 (d, 1H), 4.61 (d, 1H), 4.37-4.47 (m, 2H), 4.16 (dt, 1H), 4.06 (dt, 1H), 3.31-3.45 (m, 2H), 2.68 (quin, 2H), 1.27 (d, 3H). MS obsd. (ESI$^+$) [(M+H)$^+$]: 431.

Example 33-2 (5 mg, from intermediate I-25-2) was obtained as a white solid. $^1$H NMR (400 MHz, CDCl$_3$) δ ppm 7.08-7.21 (m, 2H), 6.89 (br. s., 1H), 5.21 (br. s., 1H), 5.02 (d, 1H), 4.61 (d, 1H), 4.43 (br. s., 2H), 4.12-4.23 (m, 1H), 4.01-4.11 (m, 1H), 3.38 (d, 2H), 2.68 (t, 2H), 1.27 (d, 3H). MS obsd. (ESI$^+$) [(M+H)$^+$]: 431.

Example 34

(6S)-3-(1,1-dioxo-1,2-thiazolidin-2-yl)-6-methyl-N-(3-thienylmethyl)-6,7-dihydro-4H-pyrazolo[1,5-a]pyrazine-5-carboxamide

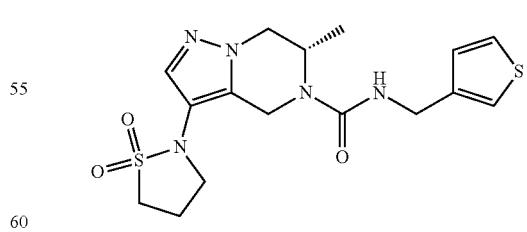

The title compound was prepared in analogy to the preparation of Example 2 by using phenyl N-(3-thienylmethyl)carbamate (intermediate I-26) instead of phenyl N-(2-chloro-4-pyridyl)carbamate (intermediate I-4). Example 34 (24 mg) was obtained as a white solid. $^1$H NMR (400 MHz, CDCl$_3$) δ 7.52 (s, 1H), 7.28-7.24 (m, 1H), 7.14 (d, 1H), 7.04

(dd, 1H), 5.04-4.87 (m, 1H), 4.76 (d, 1H), 4.46-4.33 (m, 3H), 4.19 (dd, 1H), 4.03 (d, 1H), 3.66-3.55 (m, 2H), 3.41 (s, 1H), 3.29 (t, 2H), 2.53-2.40 (m, 2H), 1.14 (d, 3H). (ESI$^+$) [(M+H)$^+$]: 396.

Example 35

(2S)-1-[2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2-thiazolidin-4-yl]pyrrolidine-2-carboxylic Acid

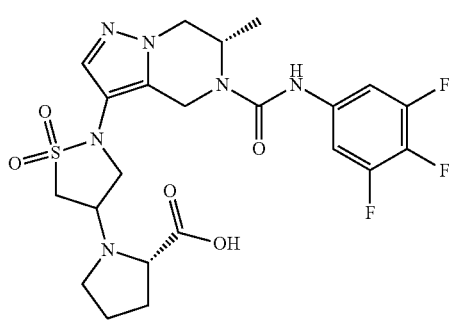 [SMILES: C[C@H]1Cn2ncc(N3CC(N4CCC[C@H]4C(=O)O)CS3(=O)=O)c2CN1C(=O)Nc1cc(F)c(F)c(F)c1]

The title compound was prepared according to the following scheme:

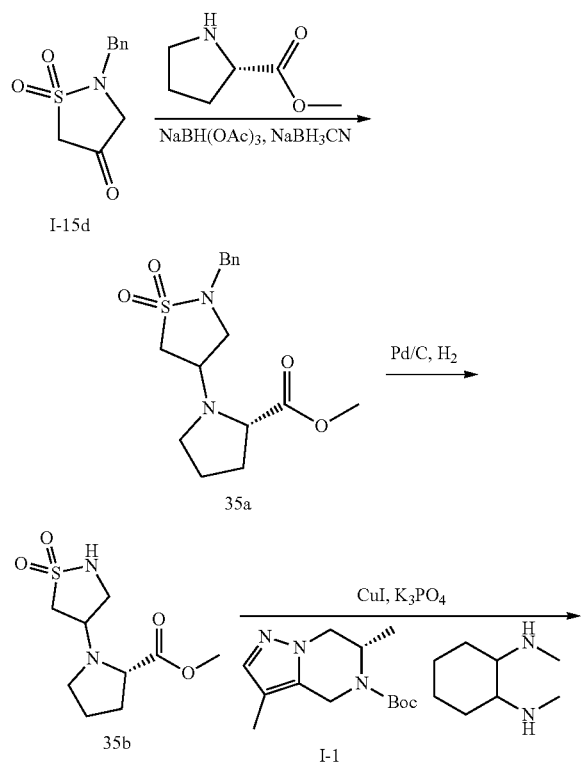

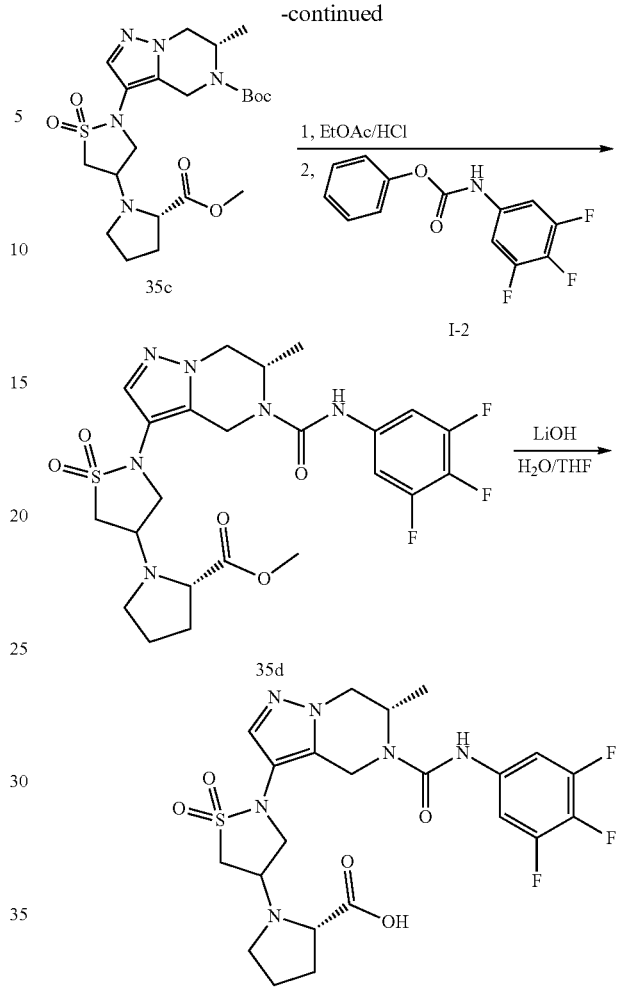

Step 1: Preparation of methyl (2S)-1-(2-benzyl-1,1-dioxo-1,2-thiazolidin-4-yl)pyrrolidine-2-carboxylate (Compound 35a)

To a solution of 2-benzyl-1,1-dioxo-1,2-thiazolidin-4-one (compound I-15d, 500 mg, 2.2 mmol) in MeOH (10 mL) was added methyl (2S)-pyrrolidine-2-carboxylate (860 mg, 6.66 mmol) and NaBH(OAc)$_3$ (1411 mg, 6.66 mmol). The resulting mixture was stirred at 20° C. for 18 hours, then NaBH$_3$CN (418 mg, 6.66 mmol) was added. The resulting mixture was stirred at 20° C. for additional 18 hours. The mixture was filtered and the filtrate was purified by prep-HPLC to give compound 35a (500 mg) as a colorless oil. MS obsd (ESI) [(M+H)$^+$]: 337.

Step 2: Preparation of methyl (2S)-1-(1,1-dioxo-1,2-thiazolidin-4-yl)pyrrolidine-2-carboxylate (Compound 35b)

To a solution of methyl (2S)-1-(2-benzyl-1,1-dioxo-1,2-thiazolidin-4-yl)pyrrolidine-2-carboxylate (compound 35a, 100 mg, 0.3 mmol) in MeOH (5 mL) was added Pd/C (300 mg). The reaction mixture was stirred at 60° C. for 18 hours under H$_2$ (50 psi), then filtered. The filtrate was concentrated under reduced pressure. The residue was purified by chromatography to give compound 35b (30 mg) as a colorless oil. MS obsd (ESI) [(M+H)⁺]: 249.

Step 3: Preparation of tert-butyl (6S)-3-[4-[(2S)-2-methoxycarbonylpyrrolidin-1-yl]-1,1-dioxo-1,2-thiazolidin-2-yl]-6-methyl-6,7-dihydro-4H-pyrazolo[1,5-a]pyrazine-5-carboxylate (Compound 35c)

To a solution of methyl (2S)-1-(1,1-dioxo-1,2-thiazolidin-4-yl)pyrrolidine-2-carboxylate (compound 35b, 130 mg, 0.52 mmol) in DMSO (1 mL) was added K₃PO₄ (330 mg, 1.56 mmol), N,N'-dimethyl-1,2-cyclohexanediamine (15 mg, 0.1 mmol), tert-butyl (6S)-3-iodo-6-methyl-6,7-dihydro-4H-pyrazolo[1,5-a]pyrazine-5-carboxylate (intermediate I-1, 380 mg) and CuI (20 mg, 0.1 mmol). The resulting mixture was stirred at 110° C. for 15 hours under N₂. The mixture was purified by prep-HPLC to give compound 35c (30 mg) as a white solid. MS obsd (ESI) [(M+H)⁺]: 484.

Step 4: Preparation of methyl (2S)-1-[2-[(6S)-6-methyl-5-[(3,4,5-trifluorophenyl)carbamoyl]-6,7-dihydro-4H-pyrazolo 1,5-a]pyrazin-3-yl-1,1-dioxo-1,2-thiazolidin-4-yl]pyrrolidine-2-carboxylate (Compound 35d)

To a solution of tert-butyl (6S)-3-[4-[(2S)-2-methoxycarbonylpyrrolidin-1-yl]-1,1-dioxo-1,2-thiazolidin-2-yl]-6-methyl-6,7-dihydro-4H-pyrazolo[1,5-a]pyrazine-5-carboxylate (compound 35c, 30 mg, 0.06 mmol) in EtOAc (5 mL) was added HCl/EtOAc (2 mL). The resulting mixture was stirred at 20° C. for 2 hours, then concentrated under reduced pressure. The residue was dissolved in DMF (1 mL), followed by addition of Et₃N (13 mg, 0.13 mmol) and phenyl N-(3,4,5-trifluorophenyl)carbamate (intermediate I-2, 21 mg, 0.08 mmol). The resulting mixture was stirred at 20° C. for 15 hours, then partitioned between water (10 mL) and EtOAc (10 mL). The aqueous layer was extracted with EtOAc twice. The combined organic layer was washed with water (20 mL) and brine (20 mL), dried over anhydrous Na₂SO₄ and concentrated under reduced pressure to give crude compound 35d (40 mg) as a yellow oil which was directly used in the next step without purification. MS obsd (ESI) [(M+H)⁺]: 557.

Step 5: Preparation of (2S)-1-[2-[(6S)-6-methyl-5-[(3,4,5-trifluorophenyl)carbamoyl]-6,7-dihydro-4H-pyrazolo[1,5-a]pyrazin-3-yl]-diox-1,1-dioxo-1,2-thiazolidin-4-yl]pyrrolidine-2-carboxylic acid (Example 35)

To a mixture of methyl (2S)-1-[2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2-thiazolidin-4-yl]pyrrolidine-2-carboxylate (compound 35d, 40 mg, 0.07 mmol) in THF (3 mL) and water (1 mL) was added LiOH.H₂O (9 mg, 0.22 mmol). The resulting mixture was stirred at 20° C. for 2 hours, then acidified with 1 N HCl to pH=1. The mixture was extracted with EtOAc (20 mL) for three times. The combined organic layer was washed with brine, dried with anhydrous Na₂SO₄ and concentrated under reduced pressure. The residue was purified by prep-HPLC to give Example (20 mg) as a white solid. ¹H NMR (400 MHz, MeOD) δ 7.66 (d, 1H), 7.39-7.24 (m, 2H), 5.21-5.02 (m, 1H), 5.00-4.94 (m, 1H), 4.56 (dd, 1H), 4.35-4.04 (m, 3H), 3.92-3.81 (m, 1H), 3.81-3.56 (m, 3H), 3.60 (br dd, 1H), 3.36 (br s, 1H), 3.43 (br s, 1H), 2.99-2.79 (m, 1H), 2.38-2.23 (m, 1H), 2.10 (br s, 1H), 2.01-1.83 (m, 2H), 1.22 (br d, 3H). MS obsd. (ESI⁺) [(M+H)⁺]: 543.

Example 36

2-[2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2-thiazolidin-4-yl]benzoic acid

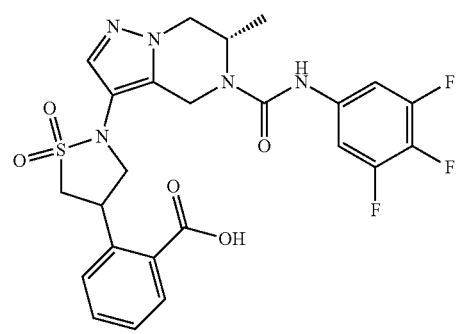 [SMILES: C[C@H]1Cn2ncc(N3CC(c4ccccc4C(=O)O)CS3(=O)=O)c2CN1C(=O)Nc1cc(F)c(F)c(F)c1]

The title compound was prepared according to the following scheme:

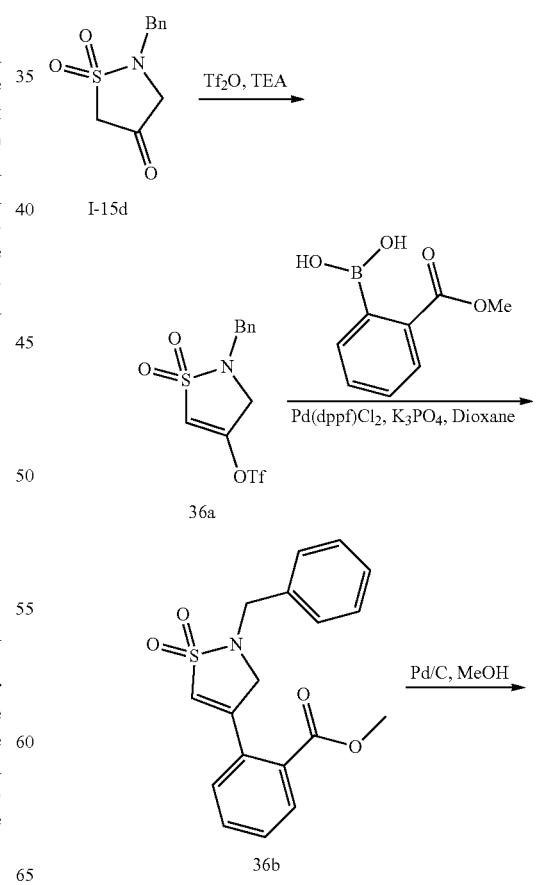

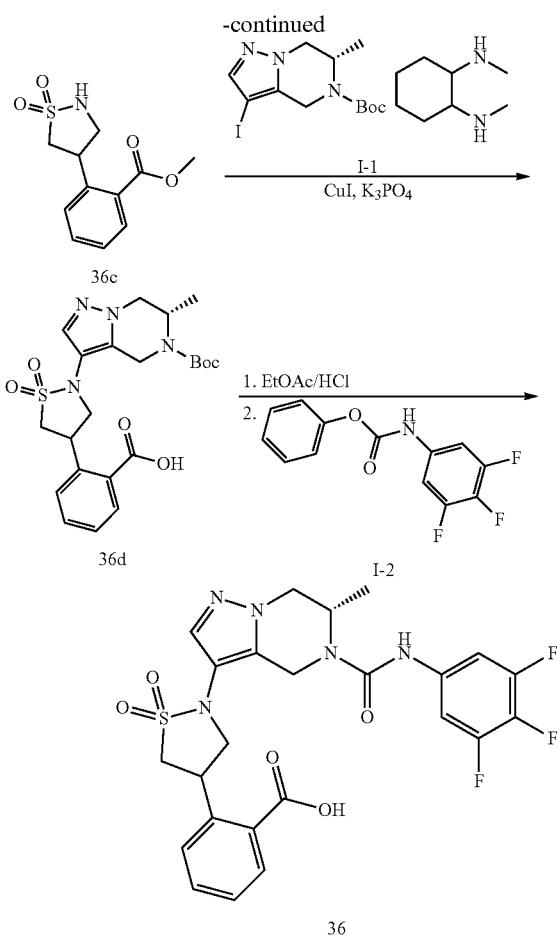

Step 1: Preparation of (2-benzyl-1,1-dioxo-3H-isothiazol-4-yl) trifluoromethanesulfonate (Compound 36a)

To a solution of 2-benzyl-1,1-dioxo-1,2-thiazolidin-4-one (compound I-15d, 5 g, 22 mmol) in DCM (100 mL) was added TEA (4.6 mL, 33 mmol). The solution was cooled to −78° C., then Tf$_2$O (7.5 g, 26.6 mmol) was added dropwise over 5 minutes under N$_2$. The reaction mixture was stirred at −78° C. for 1 hour, then quenched by adding water (50 mL). The resulting mixture was diluted with DCM (500 mL). The organic layer was separated and washed with water and 1 N hydrochloric acid, dried over anhydrous Na$_2$SO$_4$, and concentrated under reduced pressure. The residue was purified by column chromatography (PE: EA=20: 1-5:1) to give compound 36a (2.8 g) as a white solid. $^1$H NMR (400 MHz, DMSO-d$_6$) δ 7.36-7.44 (m, 5H), 6.78 (s, 1H), 4.40 (s, 2H), 3.90 (s, 2H).

Step 2: Preparation of methyl 2-(2-benzyl-1,1-dioxo-3H-isothiazol-4-yl)benzoate (Compound 36b)

To a solution of (2-benzyl-1,1-dioxo-3H-isothiazol-4-yl) trifluoromethanesulfonate (compound 36a, 500 mg, 1.4 mmol) in 1,4-dioxane (10 mL) and water (2 mL) was added 2-methoxycarbonylphenylboronic acid (252 mg, 1.4 mmol), Pd(dppf)Cl$_2$ (114 mg) and K$_3$PO$_4$ (594 mg, 2.8 mmol). The reaction mixture was stirred at 100° C. for 4 hours under N$_2$, then concentrated under reduced pressure. The residue was purified by column chromatography (PE:EA=10: 1-3:1) to give compound 32b (420 mg) as a brown solid. MS obsd. (ESI$^+$) [(M+H)$^+$]: 344.

Step 3: Preparation of methyl 2-(1,1-dioxo-1,2-thiazolidin-4-yl)benzoate (Compound 36c)

To a solution of methyl 2-(2-benzyl-1,1-dioxo-3H-isothiazol-4-yl)benzoate (compound 36b, 100 mg, 0.29 mmol) in methanol (5 mL) was added Pd/C (40 mg). The mixture was stirred at 60° C. for 18 hours under H$_2$ (50 psi). The reaction was conducted at same scale twice in total. The reaction mixtures were combined and filtered. The filtrate was concentrated under reduced pressure. The residue was purified by chromatography to give compound 36c (60 mg) as a colorless oil.

Step 4: Preparation of 2-[2-[(6S)-5-tert-butoxycarbonyl-6-methyl-6,7-dihydro-4H-pyrazolo[1,5-a]pyrazin-3-yl]-1,1-dioxo-1,2-thiazolidin-4-yl]benzoic acid (Compound 36d)

To a solution of methyl 2-(1,1-dioxo-1,2-thiazolidin-4-yl) benzoate (compound 36c, 60 mg, 0.24 mmol) in DMSO (2 mL) was added CuI (9 mg, 0.05 mmol), tert-butyl (6S)-3-iodo-6-methyl-6,7-dihydro-4H-pyrazolo[1,5-a]pyrazine-5-carboxylate (intermediate I-1, 171 mg, 0.47 mmol), K$_3$PO$_4$ (150 mg, 0.71 mmol) and N,N'-dimethyl-1,2-cyclohexane-diamine (7 mg, 0.05 mmol). The mixture was stirred at 110° C. for 15 hours under N$_2$, then cooled down to r.t. and purified by prep-HPLC to give compound 36d (30 mg) as a yellow oil. MS obsd. (ESI$^+$) [(M+H)$^+$]: 477.

Step 5: Preparation of 2-[2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2-thiazolidin-4-yl]benzoic acid (Example 36)

To a solution of 2-[2-[(6S)-5-tert-butoxycarbonyl-6-methyl-6,7-dihydro-4H-pyrazolo[1,5-a]pyrazin-3-yl]-1,1-dioxo-1,2-thiazolidin-4-yl]benzoic acid (compound 36d, 25 mg, 0.05 mmol) in EtOAc (5 mL) was added EtOAc/HCl (2 mL). The resulting mixture was stirred at 25° C. for 2 hours, then concentrated under reduced pressure and the residue was dissolved in DMF (0.5 mL). To the resulting solution was added TEA (55 mg, 0.55 mmol) and phenyl N-(3,4,5-trifluorophenyl)carbamate (intermediate I-2, 17 mg, 0.06 mmol). The mixture was stirred at 25° C. for 18 hours, then purified by prep-HPLC to give Example 36 (18.4 mg) as a white solid. $^1$H NMR (400 MHz, MeOD) δ 7.88 (d, 1H), 7.74-7.67 (m, 2H), 7.65-7.56 (m, 1H), 7.43-7.35 (m, 1H), 7.34-7.22 (m, 2H), 5.19-5.09 (m, 1H), 5.01-4.95 (m, 2H), 4.65-4.51 (m, 1H), 4.35-4.23 (m, 1H), 4.20-4.08 (m, 1H), 4.05-3.94 (m, 1H), 3.90-3.72 (m, 2H), 3.66-3.53 (m, 1H), 1.23 (dd, 3H). MS obsd. (ESI$^+$) [(M+H)$^+$]: 550.

Example 37: HBV Inhibition Assays

Cell Line and Culture Conditions:

HepG2.2.15 is a stably-transfected cell line containing the HBV genome. It is derived from the hepatoblastoma cell line Hep G2 (American Type Culture Collection, ATCC® HB-8065™) by the published procedures described in reference: M A Selles et al. Proc. Natl. Acad. Sci. USA 1987, 84, 1005-1009. The cell line was maintained in Dulbecco's modified Eagle's medium and nutrient mixture F-12

(DMEM/F-12, Gibco, Cat. #: 11320-033) supplemented with 10% fetal bovine serum (Gibco, Cat. #:10099-141), 100 U/mL penicillin, 100 µg/mL streptomycin (Gibco, Cat. #:15140-122), and 0.3 mg/mL of G418 Sulfate (Gibco, Cat. #: 10131-027).

Anti-HBV Activity In Vitro:

HepG2.2.15 cells were seeded into 96-well plates at a density of $3\times10^4$ cells per well in culture media of 100 µL DMEM/F-12 supplemented with 2.5% fetal bovine serum, 100 U/mL penicillin, 100 µg/mL streptomycin and cultured overnight at 37° C. The test compounds were serially half-log diluted in DMSO, then diluted 100 times in culture media. 100 µL culture media containing diluted compounds were added into the plates to reach 0.5% final concentration of DMSO in every well. Five days after compound treatment, culture supernatant was collected for further analysis.

For quantitative PCR detection of extracellular HBV DNA, culture supernatant was processed by 500 µg/mL Proteinase K (Sigma, Cat. #:P2308) digestion at 50° C. for 1 hour. After heat inactivation of the enzyme at 95° C. for 15 minutes, the samples were subjected to HBV DNA quantification by qPCR. The effective compound concentration at which HBV replication was inhibited by 50% ($EC_{50}$) was determined.

The Examples of the present invention were tested in the above assays as described herein and found to have $EC_{50}$ less than 1 µM in HepG2.2.15 assay as shown in Table 1 below.

TABLE 1

Activity of compounds of this invention in HepG2.2.15 assay

| Example No | $EC_{50}$ (µM) |
| --- | --- |
| 1 | 0.0046 |
| 2 | 0.079 |
| 3 | 0.036 |
| 4 | 0.006 |
| 5 | 0.014 |
| 6 | 0.083 |
| 7 | 0.0098 |
| 8 | 0.30 |
| 9 | 0.26 |
| 10 | 0.57 |
| 11 | 0.11 |
| 12 | 0.040 |
| 13 | 0.052 |
| 14 | 0.028 |
| 15 | 0.026 |
| 16 | 0.009 |
| 17 | 0.086 |
| 18 | 0.012 |
| 19 | 0.014 |
| 20 | 0.017 |
| 21 | 0.046 |
| 22 | 0.027 |
| 23 | 0.052 |
| 24 | 0.011 |
| 25 | 0.14 |
| 26 | 0.13 |
| 27 | 0.044 |
| 28-1 | 0.021 |
| 28-2 | 0.018 |
| 29 | 0.32 |
| 30 | 0.0035 |
| 31 | 0.0097 |
| 32-1 | 0.17 |
| 33-2 | 0.093 |
| 33-1 | 0.024 |
| 33-2 | 0.41 |
| 34 | 0.099 |
| 35 | 0.0067 |
| 36 | 0.017 |

The invention claimed is:

1. A compound of formula (I),

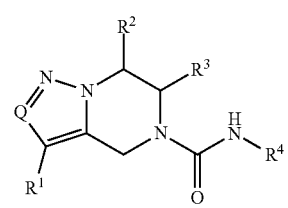

wherein:
$R^1$ is dioxooxathiazinanyl, dioxotetrahydro[1,2,5]thiadiazolo[3,2-c][1,4]oxazinyl, dioxothiadiazinanyl, dioxothiadiazolidinyl, dioxothiazetidinyl, dioxothiazolidinyl, oxothiazolidinyl or trioxotetrahydropyrrolo[2,1-d][1,2,5]thiadiazinyl, wherein $R^1$ is unsubstituted or substituted once, twice or three times by substituents independently selected from hydroxy, $C_{1-6}$alkyl, $C_{1-6}$alkoxy, $C_{1-6}$alkylcarbonyl, benzyloxycarbonyl, carboxyphenyl, carboxypyrrolidinyl and pyrimidinyloxy;
$R^2$ is H or $C_{1-6}$alkyl;
$R^3$ is $C_{1-6}$alkyl;
$R^4$ is benzothiazolyl, phenyl$C_{1-6}$alkyl, phenyl, pyridinyl, thienyl or thienyl$C_{1-6}$alkyl wherein $R^4$ is unsubstituted or once, twice or three times substituted by substituents independently selected from halogen, cyano, $C_{1-6}$alkyl and halo$C_{1-6}$alkyl; and
Q is CH or N;
or a pharmaceutically acceptable salt, enantiomer or diastereomer thereof.

2. A compound according to claim 1, wherein:
$R^1$ is selected from the group consisting of: dioxooxathiazinanyl; dioxotetrahydro[1,2,5]thiadiazolo[3,2-c][1,4]oxazinyl; dioxothiadiazinanyl, unsubstituted or substituted by hydroxy, $C_{1-6}$alkylcarbonyl or benzyloxycarbonyl; dioxothiadiazolidinyl, unsubstituted or substituted once or twice by $C_{1-6}$alkyl; dioxothiazetidinyl, unsubstituted or substituted by $C_{1-6}$alkyl; dioxothiazolidinyl, unsubstituted or substituted once or twice by substituents independently selected from hydroxy, $C_{1-6}$alkyl, $C_{1-6}$alkoxy, carboxyphenyl, carboxypyrrolidinyl and pyrimidinyloxy; oxothiazolidinyl; and trioxotetrahydropyrrolo[2,1-d][1,2,5]thiadiazinyl;
$R^2$ is H;
$R^3$ is $C_{1-6}$alkyl;
$R^4$ is selected from the group consisting of: benzothiazolyl; phenyl$C_{1-6}$alkyl; phenyl, once, twice or three times substituted by substituents independently selected from halogen, cyano, $C_{1-6}$alkyl and halo$C_{1-6}$alkyl; pyridinyl, substituted by halogen or halo$C_{1-6}$alkyl; thienyl; and thienyl$C_{1-6}$alkyl; and
Q is CH or N;
or a pharmaceutically acceptable salt, enantiomer or diastereomer thereof.

3. A compound according to claim 2, wherein:
$R^1$ is dioxooxathiazinanyl, dioxotetrahydro[1,2,5]thiadiazolo[3,2-c][1,4]oxazinyl, dioxothiadiazinanyl, hydroxydioxothiadiazinanyl, acetyldioxothiadiazinanyl, benzyloxycarbonyldioxothiadiazinanyl, dioxothiadiazolidinyl, methyldioxothiadiazolidinyl, dimehtyldioxothiadiazolidinyl, dioxothiazetidinyl, methyldioxothiazetidinyl, dioxothiazolidinyl, hydroxy-

91 dioxothiazolidinyl, hydroxy(methyl)dioxothiazolidinyl, methoxy(methyl)dioxothiazolidinyl, methyldioxothiazolidinyl, carboxyphenyldioxothiazolidinyl, carboxypyrrolidinyldioxothiazolidinyl, pyrimidinyloxy(methyl)dioxothiazolidinyl, oxothiazolidinyl or 1,1-dioxo-3a,4,6,7-tetrahydro-3H-[1,2,5]thiadiazolo[3,2-c][1,4]oxazin-2-yl;

$R^2$ is H;

$R^3$ is methyl;

$R^4$ is benzothiazolyl, benzyl, fluorophenyl, fluorochlorophenyl, fluorocyanophenyl, fluoro(methyl)phenyl, fluoro(trifluoromethyl)phenyl, trifluorophenyl, chloropyridinyl, difluoromethylpyridinyl, thienyl or thienylmethyl; and Q is CH or N;

or a pharmaceutically acceptable salt, enantiomer or diastereomer thereof.

4. A compound according to claim 3, wherein Q is CH.

5. A compound according to claim 4, wherein $R^1$ is dioxothiazolidinyl, and is unsubstituted or substituted once or twice by substituents independently selected from hydroxy, $C_{1-6}$alkyl, $C_{1-6}$ alkoxy, carboxyphenyl, carboxypyrrolidinyl, and pyrimidinyloxy.

6. A compound according to claim 5, wherein $R^1$ is dioxothiazolidinyl, hydroxydioxothiazolidinyl, hydroxy(methyl)dioxothiazolidinyl, methoxy(methyl)dioxothiazolidinyl, methyldioxothiazolidinyl, carboxyphenyldioxothiazolidinyl, carboxypyrrolidinyldioxothiazolidinyl or pyrimidinyloxy(methyl)dioxothiazolidinyl.

7. A compound selected from the group consisting of:
- (6S)-3-(1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;
- (6S)—N-(2-chloro-4-pyridyl)-3-(1,1-dioxo-1,2-thiazolidin-2-yl)-6-methyl-6,7-dihydro-4H-pyrazolo[1,5-a]pyrazine-5-carboxamide;
- (6S)—N-(4-chloro-3-fluoro-phenyl)-3-(1,1-dioxo-1,2-thiazolidin-2-yl)-6-methyl-6,7-dihydro-4H-pyrazolo[1,5-a]pyrazine-5-carboxamide;
- (6S)-3-(1,1-dioxo-1,2-thiazolidin-2-yl)-N-(4-fluoro-3-methyl-phenyl)-6-methyl-6,7-dihydro-4H-pyrazolo[1,5-a]pyrazine-5-carboxamide;
- (6S)—N-(3-cyano-4-fluoro-phenyl)-3-(1,1-dioxo-1,2-thiazolidin-2-yl)-6-methyl-6,7-dihydro-4H-pyrazolo[1,5-a]pyrazine-5-carboxamide;
- (6S)—N-[2-(difluoromethyl)-4-pyridyl]-3-(1,1-dioxo-1,2-thiazolidin-2-yl)-6-methyl-6,7-dihydro-4H-pyrazolo[1,5-a]pyrazine-5-carboxamide;
- (6S)-3-(1,1-dioxo-1,2-thiazolidin-2-yl)-N-[4-fluoro-3-(trifluoromethyl)phenyl]-6-methyl-6,7-dihydro-4H-pyrazolo[1,5-a]pyrazine-5-carboxamide;
- (6S)-3-(1,1-dioxo-1,2-thiazolidin-2-yl)-N-(2-fluorophenyl)-6-methyl-6,7-dihydro-4H-pyrazolo[1,5-a]pyrazine-5-carboxamide;
- (6S)—N-(1,3-benzothiazol-6-yl)-3-(1,1-dioxo-1,2-thiazolidin-2-yl)-6-methyl-6,7-dihydro-4H-pyrazolo[1,5-a]pyrazine-5-carboxamide;
- (6S)-3-(1,1-dioxo-1,2-thiazolidin-2-yl)-6-methyl-N-(3-thienyl)-6,7-dihydro-4H-pyrazolo[1,5-a]pyrazine-5-carboxamide;
- 6S)—N-benzyl-3-(1,1-dioxo-1,2-thiazolidin-2-yl)-6-methyl-6,7-dihydro-4H-pyrazolo[1,5-a]pyrazine-5-carboxamide;
- (6S)-3-(1,1-dioxo-3a,4,6,7-tetrahydro-3H-[1,2,5]thiadiazolo[3,2-c][1,4]oxazin-2-yl)-6-methyl-N-(3,4,5-trifluorophenyl)-6,7-dihydro-4H-pyrazolo[1,5-a]pyrazine-5-carboxamide;

92

- benzyl-2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2,5-thiadiazinane-5-carboxylate;
- (6S)-6-methyl-N-(3,4,5-trifluorophenyl)-3-(3,3,6-trioxo-4,7,8,8a-tetrahydro-1H-pyrrolo[2,1-d][1,2,5]thiadiazin-2-yl)-6,7-dihydro-4H-pyrazolo[1,5-a]pyrazine-5-carboxamide;
- (6S)-3-(5-acetyl-1,1-dioxo-1,2,5-thiadiazinan-2-yl)-6-methyl-N-(3,4,5-trifluorophenyl)-6,7-dihydro-4H-pyrazolo[1,5-a]pyrazine-5-carboxamide;
- (6S)-6-methyl-3-(3-methyl-1,1-dioxo-1,2-thiazolidin-2-yl)-N-(3,4,5-trifluorophenyl)-6,7-dihydro-4H-pyrazolo[1,5-a]pyrazine-5-carboxamide;
- (6S)-6-methyl-3-(1-oxo-1,2-thiazolidin-2-yl)-N-(3,4,5-trifluorophenyl)-6,7-dihydro-4H-pyrazolo[1,5-a]pyrazine-5-carboxamide;
- (6S)-3-(4-hydroxy-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;
- (6S)-3-(1,1-dioxo-1,2,5-thiadiazolidin-2-yl)-6-methyl-N-(3,4,5-trifluorophenyl)-6,7-dihydro-4H-pyrazolo[1,5-a]pyrazine-5-carboxamide;
- (6S)-6-methyl-3-(5-methyl-1,1-dioxo-1,2,5-thiadiazolidin-2-yl)-N-(3,4,5-trifluorophenyl)-6,7-dihydro-4H-pyrazolo[1,5-a]pyrazine-5-carboxamide;
- (6S)-6-methyl-3-[(3S)-3-methyl-1,1-dioxo-thiazetidin-2-yl]-N-(3,4,5-trifluorophenyl)-6,7-dihydro-4H-pyrazolo[1,5-a]pyrazine-5-carboxamide;
- (6S)-6-methyl-3-[(3S)-3-methyl-1,1-dioxo-1,2,5-thiadiazolidin-2-yl]-N-(3,4,5-trifluorophenyl)-6,7-dihydro-4H-pyrazolo[1,5-a]pyrazine-5-carboxamide;
- (6S)-3-[(3S)-3,4-dimethyl-1,1-dioxo-1,2,5-thiadiazolidin-2-yl]-6-methyl-N-(3,4,5-trifluorophenyl)-6,7-dihydro-4H-pyrazolo[1,5-a]pyrazine-5-carboxamide;
- (6S)-3-(3,3-dioxo-1,3,4-oxathiazinan-4-yl)-6-methyl-N-(3,4,5-trifluorophenyl)-6,7-dihydro-4H-pyrazolo[1,5-a]pyrazine-5-carboxamide;
- (6S)-3-(1,1-dioxothiazetidin-2-yl)-6-methyl-N-(3,4,5-trifluorophenyl)-6,7-dihydro-4H-pyrazolo[1,5-a]pyrazine-5-carboxamide;
- (6S)-3-(4-hydroxy-1,1-dioxo-1,2,6-thiadiazinan-2-yl)-6-methyl-N-(3,4,5-trifluorophenyl)-6,7-dihydro-4H-pyrazolo[1,5-a]pyrazine-5-carboxamide;
- (6S)-3-(1,1-dioxo-1,2,6-thiadiazinan-2-yl)-6-methyl-N-(3,4,5-trifluorophenyl)-6,7-dihydro-4H-pyrazolo[1,5-a]pyrazine-5-carboxamide;
- (6S)-3-(4-hydroxy-3-methyl-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;
- (6S)-3-(4-hydroxy-3-methyl-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;
- (6S)—N-[2-(difluoromethyl)-4-pyridyl]-3-(4-hydroxy-3-methyl-1,1-dioxo-1,2-thiazolidin-2-yl)-6-methyl-6,7-dihydro-4H-pyrazolo[1,5-a]pyrazine-5-carboxamide;
- (6S)-6-methyl-3-(3-methyl-1,1-dioxo-4-pyrimidin-2-yloxy-1,2-thiazolidin-2-yl)-N-(3,4,5-trifluorophenyl)-6,7-dihydro-4H-pyrazolo[1,5-a]pyrazine-5-carboxamide;
- (6S)-3-(4-methoxy-3-methyl-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;
- (6S)—N-[2-(difluoromethyl)-4-pyridyl]-3-(4-methoxy-3-methyl-1,1-dioxo-1,2-thiazolidin-2-yl)-6-methyl-6,7-dihydro-4H-pyrazolo[1,5-a]pyrazine-5-carboxamide;

(6S)—N-[2-(difluoromethyl)-4-pyridyl]-3-(4-methoxy-3-methyl-1,1-dioxo-1,2-thiazolidin-2-yl)-6-methyl-6,7-dihydro-4H-pyrazolo[1,5-a]pyrazine-5-carboxamide;

3-(1,1-dioxo-1,2-thiazolidin-2-yl)-6-methyl-N-(3,4,5-trifluorophenyl)-6,7-dihydro-4H-triazolo[1,5-a]pyrazine-5-carboxamide;

3-(1,1-dioxo-1,2-thiazolidin-2-yl)-6-methyl-N-(3,4,5-trifluorophenyl)-6,7-dihydro-4H-triazolo[1,5-a]pyrazine-5-carboxamide;

(6S)-3-(1,1-dioxo-1,2-thiazolidin-2-yl)-6-methyl-N-(3-thienylmethyl)-6,7-dihydro-4H-pyrazolo[1,5-a]pyrazine-5-carboxamide;

(2S)-1-[2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2-thiazolidin-4-yl]pyrrolidine-2-carboxylic acid; and 2-[2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2-thiazolidin-4-yl]benzoic acid, or a pharmaceutically acceptable salt thereof.

8. A compound selected from the group consisting of:
(6S)-3-(1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;

(6S)-3-(1,1-dioxo-1,2-thiazolidin-2-yl)-N-(4-fluoro-3-methyl-phenyl)-6-methyl-6,7-dihydro-4H-pyrazolo[1,5-a]pyrazine-5-carboxamide;

(6S)-6-methyl-3-(3-methyl-1,1-dioxo-1,2-thiazolidin-2-yl)-N-(3,4,5-trifluorophenyl)-6,7-dihydro-4H-pyrazolo[1,5-a]pyrazine-5-carboxamide;

(6S)-3-(4-hydroxy-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide;

(6S)-3-(1,1-dioxo-1,2,5-thiadiazolidin-2-yl)-6-methyl-N-(3,4,5-trifluorophenyl)-6,7-dihydro-4H-pyrazolo[1,5-a]pyrazine-5-carboxamide;

(6S)-3-(3,3-dioxo-1,3,4-oxathiazinan-4-yl)-6-methyl-N-(3,4,5-trifluorophenyl)-6,7-dihydro-4H-pyrazolo[1,5-a]pyrazine-5-carboxamide;

(6S)-6-methyl-3-(3-methyl-1,1-dioxo-4-pyrimidin-2-yloxy-1,2-thiazolidin-2-yl)-N-(3,4,5-trifluorophenyl)-6,7-dihydro-4H-pyrazolo[1,5-a]pyrazine-5-carboxamide;

(6S)-3-(4-methoxy-3-methyl-1,1-dioxo-1,2-thiazolidin-2-yl)-6-methyl-N-(3,4,5-trifluorophenyl)-6,7-dihydro-4H-pyrazolo[1,5-a]pyrazine-5-carboxamide; and (2S)-1-[2-[(6S)-6-methyl-5-[(3,4,5-trifluorophenyl)carbamoyl]-6,7-dihydro-4H-pyrazolo[1,5-a]pyrazin-3-yl]-1,1-dioxo-1,2-thiazolidin-4-yl]pyrrolidine-2-carboxylic acid, or a pharmaceutically acceptable salt thereof.

9. A method for preparing a compound of formula (VII), the method comprising:

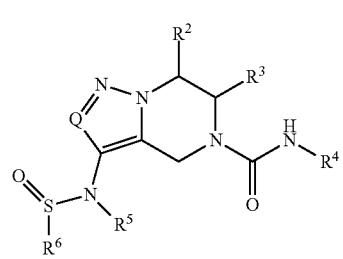

VII a) reacting a compound of formula (V)

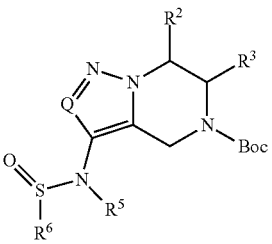

(V)

with an acid followed by reaction with phenyl carbamate (VI);

wherein:
R² is H or C₁₋₆alkyl;
and R³ is C₁₋₆alkyl;
R⁵ and R⁶ together with the nitrogen and sulfur atom to which they are attached form a 4-10 membered heterocyclyl,
Q is CH or N; and
R⁴ is benzothiazolyl, phenylC₁₋₆alkyl, phenyl, pyridinyl, thienyl or thienylC₁₋₆alkyl wherein R⁴ is unsubstituted or once, twice or three times substituted by substituents independently selected from halogen, cyano, C₁₋₆alkyl and haloC₁₋₆alkyl.

10. A pharmaceutical composition comprising a compound in accordance with claim 1, or a pharmaceutically acceptable salt, enantiomer or diastereomer thereof, and a therapeutically inert carrier.

11. A method for treating a hepatitis B virus infection, which method comprises administering a therapeutically effective amount of a compound as defined in claim 1, or a pharmaceutically acceptable salt thereof, to a subject in need thereof.

12. A method for preparing a compound of formula (X), the method comprising:

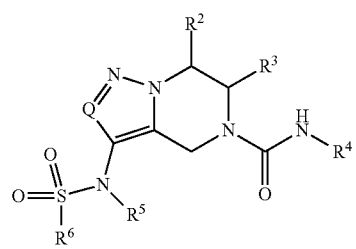

X reacting a compound of formula (IX),

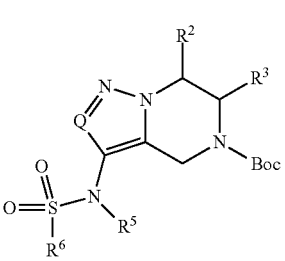

(IX)

with an acid followed by reaction with phenyl carbamate (VI);

wherein:
$R^2$ is H or $C_{1-6}$alkyl;
and $R^3$ is $C_{1-6}$alkyl;
$R^5$ and $R^6$ together with the nitrogen and sulfur atom to which they are attached form a 4-10 membered heterocyclyl;
Q is CH or N; and
$R^4$ is benzothiazolyl, phenyl$C_{1-6}$alkyl, phenyl, pyridinyl, thienyl or thienyl$C_{1-6}$alkyl wherein $R^4$ is unsubstituted or once, twice or three times substituted by substituents independently selected from halogen, cyano, $C_{1-6}$alkyl and halo$C_{1-6}$alkyl.

* * * * *